US006326372B1

(12) United States Patent
Evans et al.

(10) Patent No.: US 6,326,372 B1
(45) Date of Patent: Dec. 4, 2001

(54) LACTAM AND CYCLIC UREA DERIVATIVES USEFUL AS ALPHA 1A ADRENOCEPTOR ANTAGONISTS

(75) Inventors: Ben E. Evans, Lansdale; Kevin F. Gilbert, Barto, both of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/671,407

(22) Filed: Sep. 27, 2000

Related U.S. Application Data

(60) Provisional application No. 60/156,755, filed on Sep. 30, 1999.

(51) Int. Cl.[7] ....................... C07D 239/82; C07D 487/22; C07D 487/14; A61K 31/517; A61K 31/519
(52) U.S. Cl. .................. 514/258; 514/269; 514/278; 514/307; 514/317; 514/319; 514/320; 514/326; 514/327; 514/333; 514/336; 544/253; 544/286; 544/316; 546/141; 546/183; 546/186; 546/187; 546/188; 546/192; 546/196; 546/207; 546/208; 546/222; 546/226
(58) Field of Search ..................... 544/253, 286, 544/316; 546/141, 183, 186, 187, 188, 192, 196, 207, 208, 222, 226; 514/258, 269, 278, 307, 317, 319, 320, 326, 327, 333, 336

(56) References Cited

U.S. PATENT DOCUMENTS

| | | | |
|---|---|---|---|
| 5,403,847 | 4/1995 | Gluchowski et al. | 514/318 |
| 5,578,611 | 11/1996 | Gluchowski et al. | 514/318 |
| 5,610,174 | 3/1997 | Craig et al. | 514/401 |
| 5,620,993 | 4/1997 | Patane et al. | 514/321 |
| 5,661,163 | 8/1997 | Patane et al. | 514/331 |
| 5,760,054 | 6/1998 | Huff et al. | 514/302 |

FOREIGN PATENT DOCUMENTS

| | | |
|---|---|---|
| 0204597 | 12/1986 | (EP) . |
| 0748800 | 12/1996 | (EP) . |
| WO 92/00073 | 1/1992 | (WO) . |
| WO 92/16213 | 10/1992 | (WO) . |
| WO 94/08040 | 4/1994 | (WO) . |
| WO 94/10989 | 5/1994 | (WO) . |
| WO 94/22829 | 10/1994 | (WO) . |
| WO 95/28397 | 10/1995 | (WO) . |
| WO 96/14846 | 5/1996 | (WO) . |
| WO 96/25934 | 8/1996 | (WO) . |
| WO 96/39140 | 12/1996 | (WO) . |
| WO 96/40135 | 12/1996 | (WO) . |
| WO 97/17969 | 5/1997 | (WO) . |
| WO 97/42956 | 11/1997 | (WO) . |
| WO 98/51311 | 11/1998 | (WO) . |
| WO 98/57632 | 12/1998 | (WO) . |
| WO 98/57638 | 12/1998 | (WO) . |
| WO 98/57639 | 12/1998 | (WO) . |
| WO 98/57640 | 12/1998 | (WO) . |
| WO 98/57641 | 12/1998 | (WO) . |
| WO 98/57642 | 12/1998 | (WO) . |
| WO 98/57940 | 12/1998 | (WO) . |
| WO 00/43374 | 7/2000 | (WO) . |

OTHER PUBLICATIONS

Zara–Kaczian et al. (Acta Chim. Hung. (1990, 127(4), 607–27).*

Watson & Girdlestone, "Receptor & Ion Channel Nomenclature Supplement", 1995.

Michel, et al., "Classification of alpha 1– adrenoceptor subtypes", Naunyn–Schmiedeberg', Arch. Pharmacol., 352:1–10; 1995.

O'Malley, et al., "Characterization of specific binding of [125+–] L–762, 459, a selective alpha 1 A adrenoreceptor vadioligand" European Journal of Pharmacology, 348: 287–295 (1998).

Patane, et al. "4–amino–2–[4–]1–(benzyloxycarbony)–2(s)– . . . ", J. Med. Chem.: 41: 1205–1208: 1998.

Nerenberg, et al. "Design & Synthesis of N–Alkylated Saccharines as selective Alpha–1a Adrenergic Receptor Antagonists.": Bio Org Med. Chem L & H, vol. 8: 2467–2472, 1998.

Michelet al. Molec Pharm., "Selective Irreversible Binding of Chlorethylclonidne. . . "; 44: 1165–1170; 1993.

Wetzel, et al. "Structure function studies on the Human alpha 1a Adrenoceptor"; IBC Conference on Structure and Functions of G. Protein Coupled Receptors and Opportunities for Commercial Development, Dec. 11–13, 1995, Philadelphia, PA (1995) (Abstract,.

Chiu et al. "Synthesis of Indoramin Analogs: Pharmacological Evaluation at Cloned Human alpha–Adrenergic Receptors", 206th ACS Meeting, Chicago, IL, Aug. 22–27, 1993 (Abstract).

Chiu, et al. "Synthesis & Pharmacological Evaluation of BE2254 Analogs", 206th ACS Meeting, Chicago, IL, Aug. 22–27, 1993 (Abstract).

(List continued on next page.)

Primary Examiner—Bruck Kifle
(74) Attorney, Agent, or Firm—Baerbel R. Brown; Kenneth R. Walton; Melvin Winokur

(57) ABSTRACT

Lactam and cyclic urea derivatives and their pharmaceutically acceptable salts are disclosed. The synthesis of these compounds and their use as alpha 1*a* adrenergic receptor antagonists is also described. One application of these compounds is in the treatment of benign prostatic hyperplasia. These compounds are typically selective in their ability to relax smooth muscle tissue enriched in the alpha 1*a* receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia can be achieved.

28 Claims, No Drawings

OTHER PUBLICATIONS

Forray, C., et al. "Pharmacological Characterization of the Cloned Human & Rat Alpha–1–Adrenergic Receptors", 11th International Congress of Pharmacology, Montreal, Canada; Jul. 24–29, 1994 (Abstract).

Forray, C., et al. "Structure–function studies of the Human Alpha–1a Adrenoceptor Using Site Directed Mutagenesis."; Gordon Conference, Lucca, Italy; 1995 (Abstract).

Nagarathnam, D., et al. "Design & Synthesis of Dihydropyridines As Selective Antagonists At The Cloned Human alpha 1a Adrenoceptor", Gordon Conference, Lucca, Italy; 1995 (Abstract).

Gluchowski, C, et al. "The Discovery of Selective alpha 1a Antagonists Using recombinant Human a–Adrenoceptors", IBC Conference on Structure & Function of G–Protein Coupled Receptors and Opportunities for Commercial Development, Dec. 11–13, Philadelphia, PA (1995) (Abstract).

Nagarathnam, D., et al. "Design & Synthesis & Evaluation of Dihydropyrimidinones as aplha–1a selective antagonists: 1. identification of snap 5582 as a novel lead", 1997 Gordon Conference, (Abstract).

Nagarathnam, D., et al. "Design & Synthesis & Evaluation of Dihydropyrimidinones as alpha–1a selective antagonists: 2. Structure Activity Relationship of Snap 5582 Analogs", 1997 Gordon Conference, (Abstract).

Nagarathnam, D., et al. "Design & Synthesis & Evaluation of Dihydroprimidinones as alpha–1a selective antagonists: 3. Modification of the Piperidine Moiety", 1997 Gordon Conference, (Abstract).

Wawood, J.M., et al. "Intrinsic Profiles of 4–Aminquinazolines. . . " ACS National Meeting, Chicago, Il, Aug. 22–27, 1993 (Abstract).

Wong, W.C., et al. "Design & Synthesis of Dihydropyrimidines As Alpha 1a Adrenoceptor Selective Antagonists" 215th ACS Conference 1993 (Abstract).

Forray, C., et al. "The a–1–Adrenerigic Receptor that Mediates Smooth Muscle Contraction in Human Prostate Has the Pharmacological Properties of the Cloned Human alpha 1c Subtype" Molecular Pharmacology, 45:703–708, 1994.

Laz, T.M., et al. "The Rat Homologue of the Bovine alpha 1c–Adrenergic Receptor Shows the Pharmacological Properties of the Classical alpha 1a Subtype", Molecular Pharmacology, 46:414–422, 1994.

Wong, WC, et al. "A convenient synthesis of 2–amino–2–oxazolines and Their Pharmacological Evaluation At Cloned Human alpha Adrenergic Receptrors", Bioorganic & Medicinal Chemistry Letters, vol. 4, No. 19, pp. 2317–2322, 1994.

Wetzel, J.M. et al. "Discovery of alpha 1a–Adrenergic Receptor Antagonists Based on the L–Type Ca 2+ Channel Antagonist Niguldipine" Journal of Medicinal Chemistry, 38 1995.

Lepor, H., et al. "Localization of the alpha 1a–Adrenoceptor in the Human Prostate" The Journal of Urology, vol. 154, 2096–2099, Dec. 1995.

Wetzel, JM, et al. "Modeling and Mutagenesis of the Human alpha 1a–Adrenoceptor: Orientation and Function of Transmembrane Helix V . Sidechains" Receptors and Channels, vol. 4: pp. 165–177, 1996.

Gluckowski, C., et al. "The Discovery of Selective alpha 1 a–Antagonists Using Recombinant Human alpha Adrenoceptors" IBC BioMedical Library Series (Abstract) (1995).

Gluckowski, C., et al. "The Discovery of Selective alpha 1 a–Antagonists Using Recombinant Human alpha Adrenoceptors" 25th National Medical Chem. Symposium , University of Michigan, Ann Arbor, Michigan, Jun. 18–22, 1996(Abstract).

Chang et al. Potencies of alpha 1A (Snap 6201 and Snap 5399) alpha B (L–765,314) and alpha 1D (BMY 7378) subtype selective antagonists in isolated rat, dog, monkey, and human tissues. XIIIth int'l congress of Pharma. Jul. 26–31, 1998, Munchen, Germany, Nauyn–Schmiedberg's Arch. of Pharm 358, suppl. 2. R593.

Wetzel, J.M. "Discovery of alpha 1a–Adrenergic Receptor Antagonists Based on the L–Type Ca2 Channel Antagonist Niguldipine", Journal of Medicinal Chemistry, vol. 38, #10: May 12, 1995.

Gluckowski, C., et al. "Synthesis of Indoramin Analogs: Pharmacological Evaluation at Cloned Human g–Adrenergic Receptors" 206th ACS Meeting, Chicago, IL, Aug. 22–27, 1993 (Abstract).

Marzabadi, M., et al. "A double Protection Strategy for the Synthesis of 3.5 Disubstitution Dihydropyridines," Medicianl Chemistry.

Forray, C., et al. "Activation of Intracellular Signaling Pathways by Cloned Human Alpha–1b receptors" Experimental Biology Meeting, 1993 (Abstract).

Salon, J.A., et al. "Distribution of G. Protein and Subunits and Their Coupling to Cloned Adrenergic a–1 Receptors in Commonly Used Transfection Hosts", Society for Neuroscience 1993 meeting (Abstract).

Wetzel, J.M., et al. "Structural & Functional Studies of the Human alpha 1c Adrenergic Receptor: The Orientation of Transmembrane Helix 5" Experimental Biology 1994 (Abstract).

Forray, C., et al. "Comparison of the Pharmacological Properties of the Cloned Bovine, Human and Rat alpha 1c Adrenergic Receptors " Experimental Biology 1994 (Abstract).

Forray, C., et al. "Effects of Novel Alpha 1C Adrendergic Receptor Antagonists on the Contraction of the Human Prostate Smooth Muscle", American Urological Association Meeting in San Francisco, California 1994 (Abstract).

Wetzel, J.M. "Site Diretced Mutagenesis studies on the Human alpha 1a Adrenergic Receptor: The Orientation of Transmembrane Helix V" 210th ACS National Meeting 1995.

Wetzel, J.M. "Binding and Intrinsic Activity Profiles of 4–Aminoquinazolines and 4–Aminoquinolines at Cloned Human Alpha Adrenergic Receptors" 206th ACS National Meeting (1993) Abstract.

Marzabadi, M.M. "A Double Protection Strategy fo the Synthesis of 3,5 Distributed Dihydropyridines" Papers of the American Chemical Society, 1995 (Abstract).

Chiu, G. "Synthesis of Indoramin Analogs: Pharmacological Evaluation At Cloned Human a–Adrenergic Receptors" Presented at the 206th ACS Meeting Chicago, Il, Aug. 22–27, 1993 (Abstract).

Cui, W., "A Molecular Docking Study of the Binding of the Dihydropyridine alpha 1a Antagonist Snap 5089 to the Human alpha 1a–Adrenergic Receptor " 214th ACS Meeting, Chicago 1991 Medicinal Chemistry (Poster).

Nagaratham, D. "Design, Synthesis and Evaluation of Dihydropyrimininones as Alpha 1A Selective Antagonists: 2. Structure –Activity Relationship of Snap 5582 Analogs." 214th ACS Meeting, Chicago 1991 Medicinal Chemistry (Abstract).

Lagu, B. "Design, Synthesis, and Evaluation of Dihydropyrimidinones As Alpha 1A Selective Antagonists: 4. Dihydropyrimidin–Fused Lactones" 214th ACS 1997 (Abstract).

Wong, W.C. "Design and Synthesis of Dihydropyrimidines as alpha 1a Adrenoceptor Selective Antagonists" 215th ACS–1993 (Abstract).

Nagarathnam, D. "Design, Synthesis and Evaluation Of Dihydropyrimidinoes as Alpha–1A Selective Antagonists: 3. Modification of the Piperidine Moiety" 1997 Gordon Conference (Abstract).

Nagarathnam, D. "Design, Synthesis and Evaluation of Dihydropyrimidinoes as Alpha–1A Selective Antagonists: 3. Modification of the Piperidine Moiety" 1997 Gordon Conference (Abstract).

Nagaratham, D. "Design, Synthesis and Evaluation of Dihydropyrimininones as Alpha 1A Selective Antagonists: 5. Aryl–Piperazine Side Chains" 215th ACS Meeting, 1990 Medicinal Chemistry (Abstract).

Marzabaidi, et al. "Design and Synthesis and Evaluation of Novel Dihydropyridine Alpha –1A Antagonists" Biorganic & Medicinal Chemistry Letters 9 : pp. 2843–2848 1999.

Marzabadi, et al. "Design, Synthesis & Pharmacological Evaluation of Alpha 1A Receptor Antagonists, Effects of Pharmacophore Regio Chemistry on Potency and Selectivity" 215th ACS National Meeting, Dallas, Texas (1998) (Abstract).

Salon, J.A. "Distribution of G. Protein alpha Subunits and Their Coupling t6o Cloned Adrenergic alpha 1 Receptors in Commonly Used Transfection Hosts" Society For Neuroscience Abstracts, vol. 19, 1993. (Abstract).

Nagarathnam, D. "Design and Synthesis of Dihydropyridines as Selective Antagonists At the Cloned Human alpha 1a Adrenoceptor" Gordon Conference–1995 (Abstract).

Gluchowski, Charlos. "The Design of Subtype Selective Alpha 1 Adrenoceptor Antagonists as a Therapeutic Approach to Benign Prostatic Hyperplasia" Medicinal Chemistry Gordon Conference, Aug. 9, 1994 (Abstract).

Nagarathnam, D. "Design, Synthesis and Evaluation of Dihydropyrimidinoes as Alpha–1A selective antagonists. 2. Structure–activity relationship of Snap 5582 analogs." The American Chemical Society, V .214 1997 (Abstract).

Marzabaidi, et al. "Design and Synthesis of Novel Dihydropyridine Alpha –1A Antagonists" Biorganic & Medicinal Chemistry Letters 9 : pp. 2843–2848 1999.

* cited by examiner

LACTAM AND CYCLIC UREA DERIVATIVES USEFUL AS ALPHA 1A ADRENOCEPTOR ANTAGONISTS

This application claims the benefit of U.S. Provisional Application No. 60/156,755 filed Sept. 30, 1999, the disclosure of which is hereby incorporated by reference in its entirety.

FIELD OF THE INVENTION

This invention relates to lactam compounds, cyclic urea compounds and pharmaceutically acceptable salts thereof, their synthesis, and their use as alpha 1a adrenoceptor antagonists. More particularly, the compounds of the present invention are useful for treating benign prostatic hyperplasia (BPH).

References are made throughout this application to various publications, the disclosures of which are hereby incorporated by reference in their entireties, in order to more fully describe the state of the art to which this invention pertains.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, $\beta_1$, and $\beta_2$ subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., α-*Adrenoreceptors: Molecular Biology, Biochemistry and Pharmacology*, (*Progress in Basic and Clinical Pharmacology* series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its its own pharmacologic and tissue specificities. The designation "alpha 1a" is the appellation recently approved by the FUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Michel et al., *Naunyn-Schmiedeberg's Arch. Pharmacol.* (1995), 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concomitantly, the increased noradrenergic innervation of the enlarged prostate leads to an increased adrenergic tone of the bladder neck and urethra, further restricting the flow of urine through the urethra.

In benign prostatic hyperplasia, the male hormone 5alpha-dihydrotestosterone has been identified as the principal culprit. The continual production of 5α-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.'s product PROSCAR® (finasteride). The effect of this compound is to inhibit the enzyme testosterone 5-α reductase, which converts testosterone into 5α-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/00073, the selective ability of the R(+) enantiomer of terazosin to bind to adrenergic receptors of the alpha 1 subtype was reported. In addition, in WO 92/16213, combinations of 5α-reductase inhibitory compounds and alpha-adrenergic receptor blockers (terazosin, doxazosin, prazosin, bunazosin, indoramin, alfuzosin) were disclosed. However, no information as to the alpha 1d, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The relatively recent cloning of the human alpha 1a adrenergic receptor ATCC CRL 11140) and the use of a screening assay utilizing the cloned human alpha 1a receptor has enabled identification of compounds which specifically interact with the human alpha 1a adrenergic receptor. For further description, see WO 94/08040 and WO 94/10989. As disclosed in the instant patent disclosure, a cloned human alpha 1a adrenergic receptor and a method for identifying compounds which bind the human alpha 1a receptor have made possible the identification of selective human alpha 1a adrenergic receptor antagonists useful for treating BPH.

Several classes of compounds have been disclosed to be selective alpha 1a adrenergic receptor antagonists useful for treating BPH. WO 94/22829 discloses, for example, certain 4-(un)substituted phenyl-1,4-dihydropyridine derivatives which are described as potent, selective alpha 1a antagonists with weak calcium channel antagonistic activity and which are further described to be anticipated as useful for treating BPH. As another example, WO 96/14846, WO 97/17969 and WO 97/42956 each disclose certain dihydropyrimidine derivatives (e.g., certain 1,2,3,6-tetrahydro-2-oxo-pyrimidine derivatives) which are selective antagonists for the human alpha 1a receptor and useful for treatment of BPH, impotency, cardiac arrhythmia, and other diseases where antagonism of the alpha 1a receptor may be useful. As still another example, WO 96/40135 discloses, inter alia, certain phenylpiperidinyl alkyl saccharin derivatives and their use as selective alpha 1a antagonists. Yet another example is EP 748800, which discloses, inter alia, certain arylpiperazinylpropyl substituted pyrimidinediones useful as alpha 1 adrenoceptor antagonists. Still other alpha 1a selective antagonist compounds are disclosed in WO 98/57632, WO 98/57638, WO 98/57639, WO 98/57640, WO 98/57641, WO 98/57642, and WO 98/57940. WO 98/57940 principally discloses oxazolidinone compounds, but it also provides a generic description of certain lactam and cyclic urea compounds having, inter alia, (azacycloalkyl)-alkylaminocarbonyl side chains.

The instant patent disclosure discloses novel lactam and cyclic urea compounds which bind to the human alpha 1a receptor. These compounds are further tested for binding to other human alpha 1 receptor subtypes, as well as counter-screened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still another object of the invention is to identify alpha 1a adrenergic receptor antagonists which are useful for relaxing lower urinary tract tissue in animals, preferably mammals, especially humans.

The compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The present invention provides lactam and cyclic urea compounds and pharmaceutically acceptable salts thereof for the treatment of urinary obstruction caused by benign prostatic hyperplasia (BPH). The compounds antagonize the human alpha 1a adrenergic receptor at nanomolar and sub-nanomolar concentrations, while typically exhibiting lower affinity for the alpha 1d and alpha 1b human adrenergic receptors and many other G-protein coupled receptors. This invention can have the advantage over non-selective alpha 1 adrenoceptor antagonists of reduced side effects related to peripheral adrenergic blockade. Such side effects include hypotension, syncope, lethargy, etc.

More particularly, the present invention is a compound of formula (I):

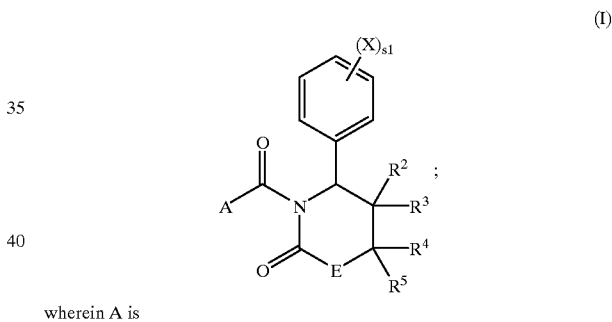

wherein A is

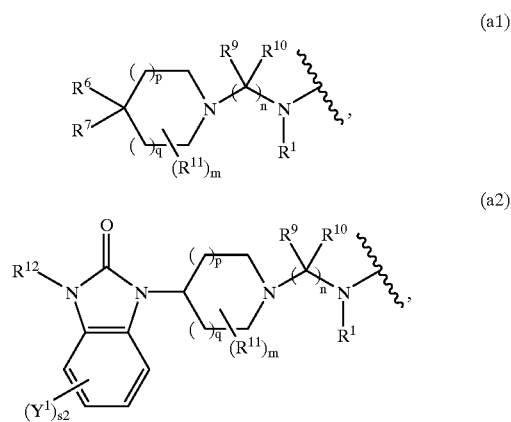

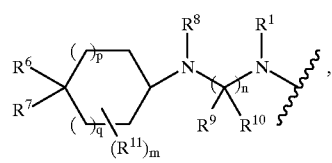

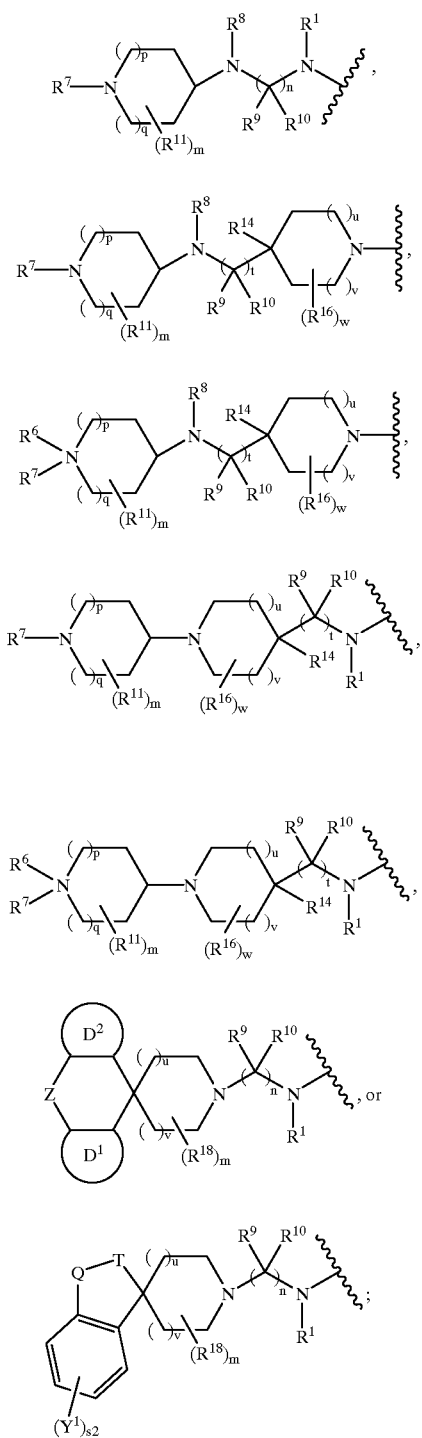

E is $CR^aR^b$ or $NR^c$;

$R^1$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, or $C_4$–$C_{20}$ cycloalkylalkyl;

$R^2$, $R^3$, $R^4$ and $R^5$ are as follows:

(i) $R^2$ and $R^3$ are each independently selected from hydrogen, cyano, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, $C_4$–$C_{20}$ cycloalkylalkyl, fluorinate $C_4$–$C_{20}$ alkylcycloalkyl, fluorinated $C_4$–$C_{20}$ cycloalkylalkyl, $(CH_2)_{0-4}CO_2R^d$, $(CH2)0$-$4OR^d$, and $(CH_2)_{0-4}CON(R^d)_2$; and $R^4$ and $R^5$ are each independently selected from hydrogen, $C_1$–$C_6$ alkyl, fluorinated $C_1 \geqq C6$ alkyl, $C_3$–$C_8$ cycloalkyl, fluorinated $C_3$–$C_8$ cycloalkyl, $C_4$–$C_{20}$ alkylcycloalkyl, $C_4$–$C_{20}$ cycloalkylalkyl, and $(CH2)_{0-4}OR^d$;

(ii) $R^2$ and $R^3$ together with the carbon atom to which they are attached form $C_4$–$C_6$ cycloalkyl or substituted $C_4$–$C_6$ cycloalkyl, wherein the each of the substituents on substituted cycloalkyl is hydrogen, halogen, cyano, $C_1$–$C_6$ alkyl, fluorinated $C_1$–$C_6$ alkyl, $C_1$–$C_6$ alkoxy, fluorinated $C_1$–$C_6$ alkoxy, $CO_2R^d$, $C_2$–$C_8$ alkoxyalkyl, or fluorinated $C_2$–$C_8$ alkoxyalkyl; and $R^4$ and $R^5$ are as defined in (i); or (iii) $R^2$ and $R^4$ together with the carbon atoms to which each is attached form $C_4$–$C_6$ cycloalkyl or substituted $C_4$–$C_6$ cycloalkyl, wherein the each of the substituents on the substituted cycloalkyl is hydrogen, halogen, cyano, $C_1$–$C_6$ alkyl, fluorinated $C_1$–$C_6$ alkyl, $C_1$–$C_6$ alkoxy, fluorinated $C_1$–$C_6$ alkoxy, $CO_2R^d$, $C_2$–$C_8$ alkoxyalkyl, or fluorinated $C_2$–$C_8$ alkoxyalkyl; and $R^3$ and $R^5$ are as defined in (i);

$R^6$ is hydrogen, cyano, hydroxy, $CO_2R^e$, $CON(R^e)_2$, aryl, or substituted aryl;

$R^7$ is aryl, substituted aryl, heterocyclic, or substituted heterocyclic;

$R^8$ is hydrogen or $C_1$–$C_4$ alkyl;

$R^9$ and $R^{10}$ are each independently selected from hydrogen, $C_1$–$C_6$ alkyl, and $C_3$–$C_8$ cycloalkyl;

each $R^{11}$ is a substituent connected to a ring atom other than $CR^6R^7$ or N and is independently hydrogen or $C_1$–$C_4$ alkyl;

$R^{12}$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, or $C_4$–$C_{20}$ cycloalkylalkyl;

$R^{14}$ is hydrogen or $OR^e$;

each $R^{16}$ is a substituent connected to a ring atom other than N or the carbon to which $R^{14}$ is attached and is independently hydrogen or $C_1$–$C_4$ alkyl;

each $R^{18}$ is a substituent connected to a ring atom other than N or spiro subsituted carbon and is independently hydrogen or $C_1$–$C_4$ alkyl;

$D^1$ is a benzene ring, substituted benzene, heterocyclic or substituted heterocyclic, wherein each of the substituents on substituted benzene or substituted heterocyclic is independently halogen, cyano, $C_1$–$C_8$ alkyl, $C_3$–$C_8$ cycloalkyl, fluorinated $C_1$–$C_8$ alkyl, fluorinated $C_3$–$C_8$ cycloalkyl, $C_1$–$C_6$ alkoxy, fluorinated $C_1$–$C_6$ alkoxy, $C_2$–$C_8$ alkoxyalkyl, or fluorinated $C_2$–$C_8$ alkoxyalky;

$D^2$ independently has the same definition as set forth for $D^1$;

Q is absent, $[C(R^{a'}R^{b'})]_{1-4}$, $O[C(R^{a'}R^{b'})]_{1-2}$, $[C(R^{a'}R^{b'})]_{1-2}]$, $C(R^{a'})=C(R^{b'})$, $C(R^{a'}R^{b'})—C(R^{a'})=C(R^{b'})$, or $C(R^{a'})=C(R^{b'})—C(R^{a'}R^{b'})$;

T is absent, $C(=O)$, $C(=O)O$, $N(SO_2R^{c'})C(R^{a'}R^{b'})$, $N(R^{c'})C=O$, or $N(R^{c'})$ $C(=O)O$, provided that (i) when T is absent, Q is $[C(R^{a'}R^{b'})]_{2-4}$, $O[C(R^{a'}R^{b'})]_{1-2}$, $[C(R^{a'}R^{b'})]_{1-20}$, $C(R^{a'})—C(R^{b'})$, $C(R^{a'}R^{b'})—C(R^{a'})—C(R^{b'})$, or $C(R^{a'})—C(R^{b'})—C(R^{a'}R^{b'})$; (ii) when T is $C(=O)$ or $C(=O)O$, Q is $C(R^{a'}R^{b'})$ or $C(R^{a'}R^{b'})C(R^{a'}R^{b'})$; and (iii) when T is $N(SO_2R^{c'})C(R^{a'}R^{b'})$, $N(R^{c'})C=O$, or $N(R^{c'})C(=O)O$, Q is absent or $C(R^{a'}R^{b'})$; each X is independently hydrogen, halogen, cyano, $C_1$–$C_6$ alkyl, fluorinated $C_1$–$C_6$ alkyl, $C_1$–$C_6$ alkoxy, fluorinated $C_1$–C6 alkoxy, $(CH_2)_{0-4}CO_2R^d$ $C_2$–$C_8$ alkoxyalkyl, or fluorinated $C_2$–$C_8$ alkoxyalkyl; each yl is independently hydrogen, halogen, cyano, $C_1$–$C_6$ alkyl, fluorinated $C_1$–$C_6$ alkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl; Z is absent, O, S, SO, $SO_2$, NRh, C=O, NRhC(=O), C(=O)NRh, $NRhSO_2$, $SO_2NR^h$, $C(R^fR^g)$, $C(R^fR^g)$, $C(R^fR^g)$, $C(R^f)$, $C(R^g)$, $C(R^fR^g)S$, $SC(R^fR^g)$, $C(R^fR^g)SO$, $SOC(R^fR^g)$, $C(R^fR^g)NR^h$, $NRh^c$ $(R^fR^g)$, $C(R^fR^g)C(=O)$, or C(=O), $C(R^fR^g)$;

$R^a$ and $R^b$ are each independently selected from hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl and $C_4$–$C_{20}$ cycloalkylalkyl;

$R^c$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, $C_4$–$C_{20}$ cycloalkylalkyl, or $CHR^{k1}R^{k2}$;

$R^{a'}$, $R^{b'}$ and $R^{c'}$ are each independently selected from hydrogen, $C_1$–$C_4$ alkyl, and fluorinated $C_1$–$C_4$ alkyl;

$R^d$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, or $C_4$–$C_{20}$ cycloalkylalkyl;

$R^e$ is hydrogen, $C_1$–$C_6$ alkyl, $C_3$–$C_6$ cycloalkyl, or fluorinated $C_1$–$C_6$ alkyl;

$R^f$ and $R^g$ are each independently selected from hydrogen, $C_1$–$C_6$ alkyl, $C_3$–$C_6$ cycloalkyl, fluorinated $C_1$–$C_6$ alkyl, phenyl, and substituted phenyl, wherein each of the substituents on substituted phenyl is independently halo, $C_1$–$C_6$ alkyl, fluorinated $C_1$–$C_6$ alkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

$R^h$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, or $C_4$–$C_{20}$ cycloalkylalkyl;

$R^{k1}$ is hydrogen or $C_1$–$C_6$ alkyl;

$R^{k2}$ is phenyl or substituted phenyl, wherein each of the substituents on substituted phenyl is halogen, cyano, $C_1$–$C_6$ alkyl, fluorinated $C_1$–$C_6$ alkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

m is an integer from 0 to 4;

n is an integer from 2 to 6;

p, q, u, and v are each independently integers from 0 to 3;

s1 is an integer from 0 to 5;

s2 is an integer from 0 to 4;

t is an integer from 0 to 3, provided that when t is zero, $R^{14}$ is hydrogen;

w is an integer from 0 to 4; and provided that when A is of formula (a1), then $R^1$ is hydrogen;

$R^2$ and $R^3$ are each independently selected from hydrogen, methyl, ethyl, and cyclopropyl; or $R^2$ and $R^3$ together with the carbon atom to which they are attached form $C_4$–$C_6$ cycloalkyl;

$R^4$ and $R^5$ are each independently selected from hydrogen, methyl, and ethyl;

$R^6$ is hydrogen or cyano;

$R^7$ is phenyl, substituted phenyl, or pyridyl; wherein each of the substituents on substituted phenyl is independently halogen or cyano;

$R^9$ and $R^{10}$ are both hydrogen;

each X is independently hydrogen or fluorine;

$R^a$ and $R^b$ are each independently selected from hydrogen, methyl, and ethyl;

$R^c$ is hydrogen, methyl, ethyl, benzyl, or α-methylbenzyl;

m is zero;

n is 3;

p and q are each 1; and s1 is an integer from 0 to 2;

or a pharmaceutically acceptable salt thereof.

The present invention also includes pharmaceutical compositions, methods of preparing pharmaceutical compositions, and methods of treatment.

These and other embodiments, aspects and features of the present invention are either further described in or will be apparent from the ensuing description, examples and appended claims.

DETAILED DESCRIPTION OF THE INVENTION

The present invention includes lactam and cyclic urea compounds of Formula (I) above. These compounds and their pharmaceutically acceptable salts are useful as alpha 1a antagonists.

In a first embodiment, the present invention is a compound of Formula (I), wherein $R^6$ is hydrogen, cyano, hydroxy, $CO_2R^e$, $CON(R^e)_2$, phenyl, or substituted phenyl; wherein each of the substituents on substituted phenyl is independently halo, cyano, hydroxy, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

$R^7$ is phenyl, substituted phenyl, naphthyl, or substituted naphthyl, wherein each of the substituents on substituted phenyl or substituted naphthyl is independently halo, cyano, hydroxy, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl; or pyridyl, pyrazinyl, thienyl, or furanyl; or substituted pyridyl, pyrazinyl, thienyl, or furanyl, wherein each of the substitutents on substituted pyridyl, pyrazinyl, thienyl, or furanyl is independently halogen, cyano, $N(R^d)_2$, $(CH_2)_{0-4}C(=O)N(R^d)_2$, $(CH_2)_{0-4}SO_2N(R^d)_2$, $(CH_2)_{0-4}SO_2R^d$, phenyl, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

one of $R^9$ and $R^{10}$ is hydrogen, and the other of $R^9$ and $R^{10}$ is hydrogen or $C_1$–$C_6$ alkyl;

$D^1$ is a benzene ring, substituted benzene ring, heteroaryl, or substituted heteroaryl;

$D^2$ independently has the same definition as set forth for $D^1$;

p and q are integers from 0 to 3, wherein the sum of p+q is an integer equal to or less than 3;

u and v are integers from 0 to 3, wherein the sum of u+v is an integer equal to or less than 3; and provided that when A is of formula (a1), then $R^1$ is hydrogen;

$R^2$ and $R^3$ are each independently selected from hydrogen, methyl, ethyl, and cyclopropyl; or $R^2$ and $R^3$ together with the carbon atom to which they are attached form $C_4$–$C_6$ cycloalkyl;

$R^4$ and $R^5$ are each independently selected from hydrogen, methyl, and ethyl;

$R^6$ is hydrogen or cyano;

$R^7$ is phenyl, substituted phenyl, or pyridyl; wherein each of the substituents on substituted phenyl is independently halogen or cyano;

$R^9$ and $R^{10}$ are both hydrogen;

each X is independently hydrogen or fluorine;

$R^a$ and $R^b$ are each independently selected from hydrogen, methyl, and ethyl;

$R^c$ is hydrogen, methyl, ethyl, benzyl, or (α-methylbenzyl;

m is zero;

n is 3;

p and q are each 1;

s1 is an integer from 0 to 2;

and all other variables are as originally defined above;

or a pharmaceutically acceptable salt thereof.

A second embodiment of the present invention is a compound of Formula (I), wherein $R^1$ is hydrogen, $C_1$–$C_4$ alkyl, or fluorinated $C_1$–$C_4$ alkyl;

$R^6$ is hydrogen, cyano, hydroxy, $CO_2R^e$, $CON(R^e)2$, phenyl, or mono- or di- or tri- substituted phenyl;

$R^7$ is phenyl, mono- or di- or tri-substituted phenyl, pyridyl, pyrazinyl, substituted pyridyl, or substituted pyrazinyl;

$R^9$ and $R^{10}$ are both hydrogen;

$R^{14}$ is hydrogen;

m and w are each zero; and provided that when A is of formula (a1), then $R^1$ is hydrogen;

$R^2$ and $R^3$ are each independently selected from hydrogen, methyl, ethyl, and cyclopropyl; or $R^2$ and $R^3$ together with the carbon atom to which they are attached form $C_4$–$C_6$ cycloalkyl;

$R^4$ and $R^5$ are each independently selected from hydrogen, methyl, and ethyl;

$R^6$ is hydrogen or cyano;

$R^7$ is phenyl, substituted phenyl, or pyridyl; wherein each of the substituents on substituted phenyl is independently halogen or cyano;

each X is independently hydrogen or fluorine;

$R^a$ and $R^b$ are each independently selected from hydrogen, methyl, and ethyl;

$R^c$ is hydrogen, methyl, ethyl, benzyl, or α-methylbenzyl;

n is 3;

and q are each 1;

s1 is an integer from 0 to 2;

and all other variables are as previously defined in the first embodiment;

or a pharmaceutically acceptable salt thereof.

A first class of the present invention is a compound of Formula (II):

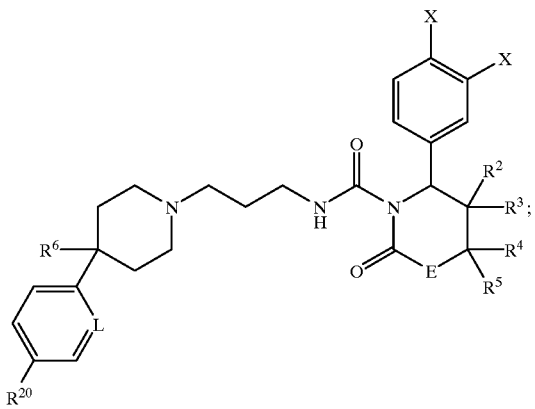

(II)

wherein E is $CR^aR^b$ or $NR^c$;

L is N or $CR^{20}$;

$R^2$ and $R^3$ are each independently selected from hydrogen, methyl, and cyclopropyl; or $R^2$ and $R^3$ together with the carbon atom to which they are attached form cyclohexyl;

$R^4$ and $R^5$ are each independently selected from hydrogen and methyl;

$R^6$ is hydrogen or cyano;

each $R^{20}$ is independently hydrogen, halogen, or cyano;

each X is independently hydrogen or fluorine;

$R^a$ and $R^b$ are each independently selected from hydrogen and methyl; and $R^c$ is hydrogen, methyl, ethyl, benzyl, or α-methylbenzyl;

or a pharmaceutically acceptable salt thereof.

An aspect of the preceding class is a compound of Formula (II), wherein E is $CR^aR^b$;

and all other variables are as defined in the first class;

or a pharmaceutically acceptable salt thereof.

Exemplary of compounds of the second embodiment are compounds selected from the group consisting of:

(6R)-1-[3-[4-(4-fluorophenyl)piperidin-1-yl] propylamino-carbonyl]-6-(3,4-difluorophenyl)-3,3-dimethylpiperidin-2-one;

(6S)-1-[3-[4-(4-fluorophenyl)piperidin-1-yl] propylamino-carbonyl]-6-(3,4-difluorophenyl)-3,3-dimethylpiperidin-2-one;

(6R)-1-[3-[4-(4-fluorophenyl)piperidin-1-yl] propylamino-carbonyl]-6-(3,4-difluorophenyl)-4,4-dimethylpiperidin-2-one;

(6S)-1-[3-[4-(4-fluorophenyl)piperidin-1-yl] propylamino-carbonyl]-6-(3,4-difluorophenyl)-4,4-dimethylpiperidin-2-one;

(4R,6R)-1-[3-[4-(4-fluorophenyl)piperidin-1-yl] propylaminocarbonyl]-6-(3,4-difluorophenyl)-4-methylpiperidin-2-one;

(4S,6R)-1-[3-[4-(4-fluorophenyl)piperidin-1-yl] propylaminocarbonyl]-6-(3,4-difluorophenyl)-4-methylpiperidin-2-one;

(4R,6S)-1-[3-[4-(4-fluorophenyl)piperidin-1-yl] propylaminocarbonyl]-6-(3,4-difluorophenyl)-4-methylpiperidin-2-one;

(4S,6S)-1-[3-[4-(4-fluorophenyl)piperidin-1-yl] propylaminocarbonyl]-6-(3,4-difluorophenyl)-4-methylpiperidin-2-one;

6(S)-1-[3-[4-(4-fluorophenyl)piperidin-1-yl]-propylaminocarbonyl]-6-(3,4-difluorophenyl) piperidin-2-one;

(6RS)-1-[3-[4-(4-fluorophenyl)piperidin-1-yl]-propylaminocarbonyl]-6-(3,4-difluorophenyl) piperidin-2-one;

6(R)-1-[3-[4-(4-fluorophenyl)piperidin-1-yl]-propylaminocarbonyl]-6-(3,4-difluorophenyl) piperidin-2-one;

(6RS)-1-[3-[4-(2-cyanophenyl)-4-cyanopiperidin-1-yl]-propylaminocarbonyl]-6-(3,4-difluorophenyl) piperidin-2-one;

6(R)-1-[3-[4-(2-cyanophenyl)-4-cyanopiperidin-1-yl]-propylaminocarbonyl]-6-(3,4-difluorophenyl) piperidin-2-one;

6(S)-1-[3-[4-(2-cyanophenyl)-4-cyanopiperidin-1-yl]-propylaminocarbonyl]-6-(3,4-difluorophenyl) piperidin-2-one;

6(R)-1-[3-[4-(4-fluorophenyl)-4-cyanopiperidin-1-yl] propyl-aminocarbonyl]-6-(3,4-difluorophenyl) piperidin-2-one;

6(S)-1-[3-[4-(4-fluorophenyl)-4-cyanopiperidin-1-yl] propyl-aminocarbonyl]-6-(3,4-difluorophenyl) piperidin-2-one;

6(R)-1-[3-[4-(2-pyridyl)piperidin-1-yl] propylaminocarbonyl]-6-(3,4-difluorophenyl) piperidin-2-one;

6(S)-1-[3-[4-(2-pyridyl)piperidin-1-yl] propylaminocarbonyl]-6-(3,4-difluorophenyl) piperidin-2-one;

6(R)-1-[3-[4-(2-cyano-4-fluorophenyl)piperidin-1-yl] propylaminocarbonyl]-6-(3,4-difluorophenyl) piperidin-2-one;

6(S)-1-[3-[4-(2-cyano-4-fluorophenyl)piperidin-1-yl] propylaminocarbonyl]-6-(3,4-difluorophenyl) piperidin-2-one;

1-[3-[4-(4-fluorophenyl)piperidin-1-yl] propylaminocarbonyl]-6-phenylpiperidin-2-one;

1-[3-(4-cyano-4-phenylpiperidin-1-yl) propylaminocarbonyl]-6-phenylpiperidin-2-one;

and pharmaceutically acceptable salts thereof.

Another aspect of the preceding class is a compound of Formula (II), wherein E is NR$^c$;

and all other variables are as defined in the first class;

or a pharmaceutically acceptable salt thereof.

Also exemplary of compounds of the second embodiment are compounds selected from the group consisting of:

(4R)-4-(3,4-difluorophenyl)-3-[(4'-(4-fluorophenyl) piperidin-1'-yl)propyl]aminocarbonyltetrahydro-pyrimidin-2-one;

(4S)-4-(3,4-difluorophenyl)-3-[(4'-(4-fluorophenyl) piperidin-1'-yl)propyl]aminocarbonyltetrahydro-pyrimidin-2-one;

(4R)-4-(3,4-difluorophenyl)-1-((R)-α-methylbenzyl)-3-[(4'-(4-fluorophenyl) piperidin-1'-yl)propyl] aminocarbonyltetrahydro-pyrimidin-2-one;

(4S)-4-(3,4-difluorophenyl)-1-((R)-α-methylbenzyl)-3-[(4'-(4-fluorophenyl) piperidin-1'-yl)propyl] aminocarbonyltetrahydro-pyrimidin-2-one;

4-(3,4-difluorophenyl)-1-((R)-α-methylbenzyl)-3-[(4'-(2-pyridyl)piperidin-1'-yl)propyl] aminocarbonyltetrahydropyrimidin-2-one;

4-(3,4-difluorophenyl)-1-((R)-α-methylbenzyl)-3-[(4'-(4-fluoro-2-cyanophenyl) piperidin-1'-yl)propyl] aminocarbonyltetrahydro-pyrimidin-2-one;

4-(3,4-difluorophenyl)-1-((R)-α-methylbenzyl)-3-[(4'-(2-cyanophenyl) piperidin-1'-yl)propyl] aminocarbonyltetrahydro-pyrimidin-2-one;

4-(3,4-difluorophenyl)-3-[(4'-cyano-4'-(2-chlorophenyl) piperidin-1'-yl)propyl]aminocarbonyltetrahydro-pyrimidin-2-one;

4-(3,4-difluorophenyl)-3-[(4'-(2-pyridyl)piperidin-1'-yl) propyl]aminocarbonyltetrahydro-pyrimidin-2-one;

4-(3,4-difluorophenyl)-3-[(4'-(2-cyanophenyl)piperidin-1'-yl)propyl]aminocarbonyltetrahydropyrimidin-2-one;

4-(3,4-difluorophenyl)-3-[(4'-cyano-4'-(2-cyanophenyl) piperidin-1'-yl)propyl] aminocarbonyltetrahydropyrimidin-2-one;

4-(3,4-difluorophenyl)-3-[4'-(2-cyano-4-fluorophenyl) piperidin-1'-yl)propyl] aminocarbonyltetrahydropyrimidin-2-one;

4-(3,4-difluorophenyl)-1-methyl-3-[(4'-(4-fluorophenyl) piperidin-1'-yl)-propyl] aminocarbonyltetrahydropyrimidin-2-one;

(4R)-4-(3,4-difluorophenyl)-5,5-dimethyl-1-((R)-α-methylbenzyl)-3-[(4'-(4-fluorophenyl)piperidin-1'-yl) propyl]amino-carbonyltetrahydropyrimidin-2-one;

(4S)-4-(3,4-difluorophenyl)-5,5-dimethyl-1-((R)-α-methylbenzyl)-3-[(4'-(4-fluorophenyl)piperidin-1'-yl) propyl]amino-carbonyltetrahydropyrimidin-2-one;

(4R)-4-(3,4-difluorophenyl)-5,5-dimethyl-3-[(4'-(4-fluorophenyl)-piperidin-1'-yl)propyl] aminocarbonyltetrahydropyrimidin-2-one;

(4R)-4-(3,4-difluorophenyl)-5,5-dimethyl-3-[(4'-(4-fluorophenyl)-piperidin-1'-yl)propyl] aminocarbonyltetrahydopyrimidin-2-one (4R)-4-(3,4-difluorophenyl)-5,5-dimethyl-1-benzyl-3-[(4'-(4-fluorophenyl) piperidin-1'-yl)propyl] aminocarbonyltetrahydropyrimidin-2-one;

(4S)-4-(3,4-difluorophenyl)-5,5-dimethyl-1-benzyl-3-[(4'-(4-fluorophenyl) pipefidin-1'-yl)propyl] aminocarbonyltetrahydropyrimidin-2-one;

(4'R)-spirocyclohexane-[1,5']-{4-(3,4-difluoropbenyl)-3-[(4'-(4-fluorophenyl) piperidin-1'-yl)propyl] aminocarbonyl}-tetrahydropyimidin-2-one;

(4'S)-spirocyclohexane-[1,5']-{4-(3,4-difluorophenyl)-3-[(4'-(4-fluorophenyl)piperidin-1'-yl)propyl] aminocarbonyl}-tetrahydropyrimidin-2-one;

(4R,5S)-5-cyclopropyl-4-(3,4-difluorophenyl)-3-[(4'-(4-fluorophenyl)-piperidin-1'-yl) propyl]aminocarbonyl-tetrahydropyrimidin-2-one;

(4S,5S)-5-cyclopropyl-4-(3,4-difluorophenyl)-3-[(4'-(4-fluorophenyl)-piperidin-1'-yl) propyl]aminocarbonyl-tetrahydropyrimidin-2-one;

(4R,5R)-5-cyclopropyl-4-(3,4-difluorophenyl)-3-[(4'-(4-fluorophenyl)-piperidin-1'-yl) propyl]aminocarbonyl-tetrahydropyrimidin-2-one;

(4S,5R)-5-cyclopropyl-4-(3,4-difluorophenyl)-3-[(4'-(4-fluorophenyl)-piperidin-1'-yl) propyl]aminocarbonyl-tetrahydropyrimidin-2-one;

(4R,5S)-5-methyl-4-(3,4-difluorophenyl)-3-[(4'-(4-fluorophenyl)piperidin-1'-yl) propyl]aminocarbonyl-tetrahydropyrimidin-2-one;

(4S,5S)-5-methyl-4-(3,4-difluorophenyl)-3-[(4'-(4-fluorophenyl)piperidin-1'-yl) propyl]aminocarbonyl-tetrahydropyrimidin-2-one;

(4R,5R)-5-methyl-4-(3,4-difluorophenyl)-3-[(4'-(4-fluorophenyl)piperidin-1'-yl) propyl]aminocarbonyl-tetrahydropyrimidin-2-one;

(4S,5R)-5-methyl-4-(3,4-difluorophenyl)-3-[(4'-(4-fluorophenyl)piperidin-1'-yl) propyl]aminocarbonyl-tetrahydropyrimidin-2-one;

and pharmaceutically acceptable salts thereof.

A preferred aspect of the invention is Isomer D of Example 21 (see below); or a pharmaceutically acceptable salt thereof.

A third embodiment of the present invention is a compound of Formula (I) wherein A is of formula (a10);

Q is absent, $[C(R^{a'}R^{b}40)]_{1-4}$, $O[C(R^{a'}R^{b'})]_{1-2}$, $[C(R^{a'}R^{b'})]_{1-2}O$, or $C(R^{a'})=C(R^{b'})$; and T is absent, $C(=O)$, $C(=O)O$, $N(SO_2R^{c'})C(R^{a'}R^{b'})$, $N(R^{c'})C=O$, or $N(R^{c'})C(=O)O$, provided that (i) when T is absent, Q is $[C(R^{a'}R^{b'})]_{2-4}$, $O[C(R^{a'}R^{b'})]_{1-2}$, $[C(R^{a'}R^{b'})]_{1-2O}$, or $C(R^{a'})=C(R^{b'})$; (ii) when T is $C(=O)$ or $C(=O)O$, Q is $C(R^{a'}R^{b'})$ or $C(R^{a'}R^{b'})C(R^{a'}R^{b'})$; and (iii) when T is $N(SO_2R^{c'})C(R^{a'}R^{b'})$, $N(R^{c'})C=O$, or $N(R^{c'})C(=O)O$, Q is absent or $C(R^{a'}R^{b'})$;

and all other variables are as defined in the first embodiment;

or a pharmaceutically acceptable salt thereof.

A second class of the present invention is a compound of Formula (III):

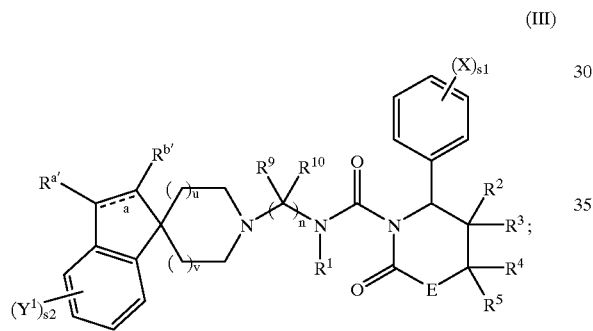

(III)

wherein

E is $CR^aR^b$ or $NR^c$;

$R^1$ is hydrogen, $C_1$–$C_4$ alkyl, or $(CH_2)_{0-4}CF_3$;

$R^2$ and $R^3$ are each independently selected from hydrogen, cyano, $C_1$–$C_4$ alkyl, $(CH_2)_{0-4}CF_3$, $C_3$–$C_6$ cycloalkyl, fluorinated $C_3$–$C_6$ cycloalkyl, $(CH_2)_{0-4}CO_2R^d$, $(CH_2)_{0-4}OR^d$, and $(CH_2)_{0-4}CON(R^d)_2$;

$R^4$ and $R^5$ are each independently selected from hydrogen, $C_1$–$C_4$ alkyl, $(CH_2)_{0-4}CF_3$, $C_3$–$C_6$ cycloalkyl, fluorinated $C_3$–$C_6$ cycloalkyl, and $(CH_2)_{0-4}OR^d$;

$R^9$ and $R^{10}$ are each independently selected from hydrogen, $C_1$–$C_6$ alkyl, and $C_3$–$C_8$ cycloalkyl;

each X is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $Y^1$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

$R^a$ and $R^b$ are each independently selected from hydrogen, $C_1$–$C_4$ alkyl, $(CH_2)_{0-4}CF_3$, $C_3$–$C_6$ cycloalkyl, and fluorinated $C_3$–$C_6$ cycloalkyl;

$R^c$ is hydrogen, $C_1$–$C_4$ alkyl, $(CH_2)_{0-4}CF_3$, $C_3$–$C_6$ cycloalkyl, fluorinated $C_3$–$C_6$ cycloalkyl, or $CHR^{k1}R^{k2}$;

$R^d$ is hydrogen, $C_1$–$C_4$ alkyl, or $(CH_2)_{0-4}CF_3$;

$R^{k1}$ is hydrogen or $C_1$–$C_4$ alkyl;

$R^{k2}$ is phenyl or substituted phenyl, wherein each of the substituents on substituted phenyl is halogen, cyano, $C_1$–$C_4$ alkyl, fluorinated $C_1$–$C_4$ alkyl, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

$R^{a'}$ and $R^{b'}$ are each independently selected from hydrogen, $C_1$–$C_4$ alkyl, and $(CH_2)_{0-4}CF_3$;

"a" represents a single bond or a double bond between the carbon atom to which $R^{a'}$ is attached and the carbon atom to which $R^{b'}$ is attached;

n is an integer from 3 to 5;

s1 is an integer from 0 to 4;

s2 is an integer from 0 to 3; and u and v are integers from 0 to 3, wherein the sum of u+v is an integer equal to or less than 3;

or a pharmaceutically acceptable salt thereof.

An aspect of the second class is a compound of Formula (IV):

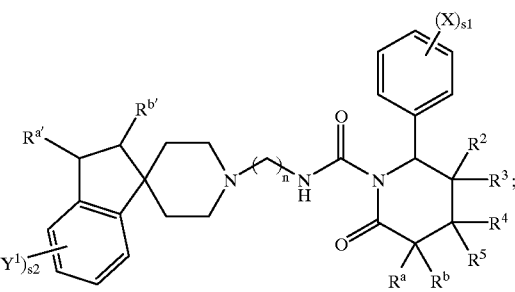

(IV)

wherein $R^2$ and $R^3$ are each independently selected from hydrogen, cyano, methyl, ethyl, $CF_3$, $CH_2CF_3$, $C_3$–$C_6$ cycloalkyl, $CO_2CH_3$, $CH_2CO_2CH_3$, $OCH_3$, $CH_2OCH_3$, $CONH_2OCH_3$, $CONH_2$, and $CH_2CONH_2$;

$R^4$ and $R^5$ are each independently selected from hydrogen, methyl, ethyl, $CF_3$, $CH_2CF_3$, $C_3$–$C_6$ cycloalkyl, $OCH_3$, $CH_2OCH_3$, $OCF_3$, $CH_2OCF_3$;

each X is independently hydrogen, fluorine, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$; p1 each $Y^2$ is independently hydrogen, halogen, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$;

s1 is an integer from 0 to 3;

s2 is an integer from 0 to 2;

and all other variables are as previously defined in the second class;

or a pharmaceutically acceptable salt thereof.

Exemplary of compounds of the third embodiment are compounds selected from the group consisting of:

6(R)-1-[3-[spiro-indane-(1,4')-piperidin-1-yl]propyl-aminocarbonyl]-6-(3,4-difluorophenyl)piperidin-2-one;

6(S)-1-[3-[spiro-indane-(1,4')-piperidin-1-yl]propyl-aminocarbonyl]-6-(3,4-difluorophenyl)piperidin-2-one;

and pharmaceutically acceptable salts thereof.

A fourth embodiment of the present invention is a compound of Formula (V):

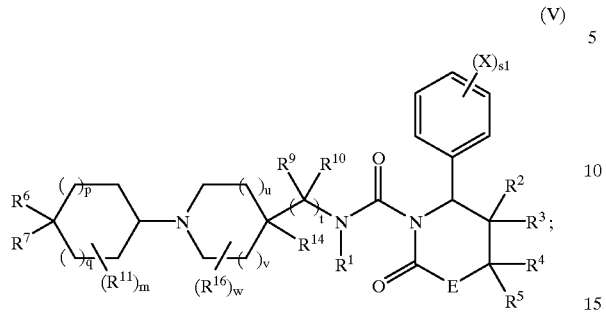

(V)

wherein $R^1$ is hydrogen, $C_1$–$C_4$ alkyl, or $(CH_2)_{0-4}CF_3$;

$R^2$ and $R^3$ are each independently selected from hydrogen, cyano, $C_1$–$C_4$ alkyl, $(CH_2)_{0-4}CF_3$, $C_3$–$C_6$ cycloalkyl, fluorinated $C_3$–$C_6$ cycloalkyl, $(CH_2)_{0-4}CO_2R^d$, $(CH_2)_{0-4}OR^d$, and $(CH_2)_{0-4}CON(R^d)_2$;

$R^4$ and $R^5$ are each independently selected from hydrogen, $C_1$–$C_4$ alkyl, $(CH_2)_{0-4}CF_3$, $C_3$–$C_6$ cycloalkyl, fluorinated $C_3$–$C_6$ cycloalkyl, and $(CH_2)_{0-4}OR^d$;

each X is independently hydrogen, halogen, cyano, $C_1$–$C_4$ alkyl, $(CH_2)_{0-4}CF_3$; $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

$R^a$ and $R^b$ are each independently selected from hydrogen, $C_1$–$C_4$ alkyl, $(CH_2)_{0-4}CF_3$, $C_3$–$C_6$ cycloalkyl, and fluorinated $C_3$–$C_6$ cycloalkyl;

$R^c$ is hydrogen, $C_1$–$C_4$ alkyl, $(CH_2)_{0-4}CF_3$, $C_3$–$C_6$ cycloalkyl, fluorinated $C_3$–$C_6$ cycloalkyl, or $CHR^{k1}R^{k2}$;

$R^d$ is hydrogen, $C_1$–$C_4$ alkyl, or $(CH_2)_{0-4}CF_3$;

$R^{k1}$ is hydrogen or $C_1$–$C_4$ alkyl;

$R^{k2}$ is phenyl or substituted phenyl, wherein each of the substituents on substituted phenyl is independently halogen, cyano, $C_1$–$C_4$ alkyl, fluorinated $C_1$–$C_4$ alkyl, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

s1 is an integer from 0 to 4;

and all other variables are as defined in the first embodiment;

or a pharmaceutically acceptable salt thereof.

A third class of the present invention is a compound of Formula (VI):

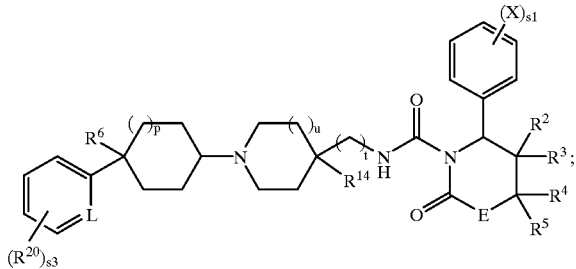

(VI)

wherein

E is $CR^aR^b$ or $NR^c$;

L is N or $CR^{20}$;

$R^2$ and $R^3$ are each independently selected from hydrogen, cyano, methyl, ethyl, $CF_3$, $CH_2CF_3$, $C_3$–$C_6$ cycloalkyl, $CO_2CH_3$, $CH_2CO_2CH_3$, $OCH_3$, $CH_2OCH_3$, $CONH_2$, and $CH_2CONH_2$;

$R^4$ and $R^5$ are each independently selected from hydrogen, methyl, ethyl, $CF_3$, $CH_2CF_3$, $C_3$–$C_6$ cycloalkyl, $OCH_3$, $CH_2OCH_3$, $OCF_3$, $CH_2OCF_3$;

$R^6$ is hydrogen, cyano, hydroxy, $CO_2CH_3$, $CO_2H$, $CONH_2$, phenyl, or substituted phenyl; wherein each of the substituents on substituted phenyl is independently fluorine, chlorine, cyano, hydroxy, methyl, ethyl, $CF_3$, $OCH_3$, $(CH_2)_{1-2}OCH_3$, or $(CH_2)_{1-2}OCF_3$, $CO_2CH_3$, or $CH_2CO_2CH_3$;

$R^{14}$ is hydrogen or hydroxy;

each $R^{20}$ is independently hydrogen, halogen, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$;

each X is independently hydrogen, fluorine, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$;

$R^a$ and $R^b$ are each independently selected from hydrogen, $C_1$–$C_4$ alkyl, $(CH_2)_{0-4}CF_3$, $C_3$–$C_6$ cycloalkyl, and fluorinated $C_3$–$C_6$ cycloalkyl;

$R^c$ is hydrogen, $C_1$–$C_4$ alkyl, $(CH_2)_{0-4}CF_3$, $C_3$–$C_6$ cycloalkyl, fluorinated $C_3$–$C_6$ cycloalkyl, or $CHR^{k1}R^{k2}$;

$R^{k1}$ is hydrogen or $C_1$–$C_4$ alkyl;

$R^{k2}$ is phenyl or substituted phenyl, wherein each of the substituents on substituted phenyl is independently halogen, cyano, $C_1$–$C_4$ alkyl, fluorinated $C_1$–$C_4$ alkyl, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

p is zero or 1;

s1 is an integer from 0 to 3;

s3 is an integer from 0 to 2;

t is an integer from 0 to 2, provided that when t is 0, $R^{14}$ is hydrogen; and u is an integer from 0 to 3;

or a pharmaceutically acceptable salt thereof.

An aspect of the preceding class is a compound of formula (VI), wherein

E is $CR^aR^b$;

and all other variables are as defined in the third class;

or a pharmaceutically acceptable salt thereof.

Exemplary of compounds of the fourth embodiment are compounds selected from the group consisting of:

6(R)-1-[[3(R)-1-[trans-4-(2-pyridyl)cyclohexyl]pyrrolidin-3-yl]-aminocarbonyl]-6-(3,4-difluorophenyl)piperidin-2-one;

6(S)-1-[[3(R)-1-[trans-4-(2-pyridyl)cyclohexyl]pyrrolidin-3-yl]-aminocarbonyl]-6-(3,4-difluorophenyl)piperidin-2-one;

and pharmaceutically acceptable salts thereof.

Another aspect of the preceding class is a compound of formula (VI), wherein

E is $NR^c$;

and all other variables are as defined in the third class;

or a pharmaceutically acceptable salt thereof.

Also exemplary of compounds of the fourth embodiment are compounds selected from the group consisting of:

3-[[3(R)-1-[trans-4-(2-pyridyl)cyclohexyl]pyrrolidin-3-yl]-aminocarbonyl]-1-((R)-α-methylbenzyl)-4-(3,4-difluorophenyl)pyrimidin-2-one;

3-[[3(R)-1-[trans-4-(2-pyridyl)cyclohexyl]pyrrolidin-3-yl]-aminocarbonyl]-4-(3,4-difluorophenyl)pyrimidin-2-one;

3-[[3(R)-1-[trans-4-(2-methoxy-4-fluorophenyl)cyclohexyl]pyrrolidin-3-yl]-aminocarbonyl]-1-((R)-α-methylbenzyl)-4-(3,4-difluorophenyl)pyrimidin-2-one;

and pharmaceutically acceptable salts thereof.

A fifth embodiment of the present invention is a compound of Formula (VII):

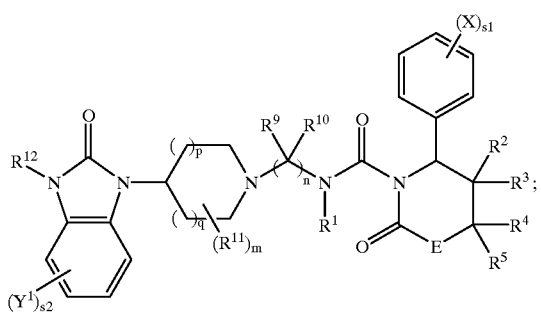

(VII)

wherein $R^1$ is hydrogen, $C_1$–$C_4$ alkyl, or $(CH_2)_{0-4}CF_3$;

$R^2$ and $R^3$ are each independently selected from hydrogen, cyano, $C_1$–$C_4$ alkyl, $(CH_2)_{0-4}CF_3$, $C_3$–$C_6$ cycloalkyl, fluorinated $C_3$–$C_6$ cycloalkyl, $(CH_2)_{0-4}CO_2R^d$, $(CH_2)_{0-4}OR^d$ and $(CH_2)_{0-4}CON(R^d)_2$;

$R^4$ and $R^5$ are each independently selected from hydrogen, $C_1$–$C_4$ alkyl, $(CH_2)_{0-4}CF_3$, $C_3$–$C_6$ cycloalkyl, fluorinated $C_3$–$C_6$ cycloalkyl, and $(CH_2)_{0-4}OR^d$;

$R^{12}$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl;

each X is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $Y^1$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

$R^a$ and $R^b$ are each independently selected from hydrogen, $C_1$–$C_4$ alkyl, $(CH_2)_{0-4}CF_3$, $C_3$–$C_6$ cycloalkyl, and fluorinated $C_3$–$C_6$ cycloalkyl;

$R^c$ is hydrogen, $C_1$–$C_4$ alkyl, $(CH_2)_{0-4}CF_3$, $C_3$–$C_6$ cycloalkyl, fluorinated $C_3$–$C_6$ cycloalkyl, or $CHR^{k1}R^{k2}$;

$R^d$ is hydrogen, $C_1$–$C_4$ alkyl, or $(CH_2)_{0-4}CF_3$;

$R^{k1}$ is hydrogen or $C_1$–$C_4$ alkyl;

$R^{k2}$ is phenyl or substituted phenyl, wherein each of the substituents on substituted phenyl is independently halogen, cyano, $C_1$–$C_4$ alkyl, fluorinated $C_1$–$C_4$ alkyl, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

n is an integer from 3 to 5;

s1 is an integer from 0 to 4;

s2 is an integer from 0 to 3;

and all other varaibles are as defined in the first embodiment;

or a pharmaceutically acceptable salt thereof.

A fourth class of the present invention is a compound of Formula (VIII):

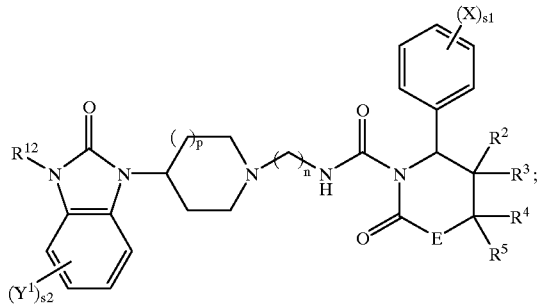

(VIII)

wherein

E is $CR^aR^b$ or $NR^c$;

$R^2$ and $R^3$ are each independently selected from hydrogen, cyano, methyl, ethyl, $CF_3$, $CH_2CF_3$, $C_3$–$C_6$ cycloalkyl, $CO_2CH_3$, $CH_2CO_2CH_3$, $OCH_3$, $CH_2OCH_3$, $CONH_2$, and $CH_2CONH_2$;

$R^4$ and $R^5$ are each independently selected from hydrogen, methyl, ethyl, $CF_3$, $CH_2CF_3$, $C_3$–$C_6$ cycloalkyl, $OCH_3$, $CH_2OCH_3$, $OCF_3$, $CH_2OCF_3$;

$R^{12}$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl;

$R^a$ and $R^b$ are each independently selected from hydrogen, $C_1$–$C_4$ alkyl, $(CH_2)_{0-4}CF_3$, $C_3$–$C_6$ cycloalkyl, and fluorinated $C_3$–$C_6$ cycloalkyl;

$R^c$ is hydrogen, $C_1$–$C_4$ alkyl, $(CH_2)_{0-4}CF_3$, $C_3$–$C_6$ cycloalkyl, fluorinated $C_3$–$C_6$ cycloalkyl, or $CHR^{k1}R^{k2}$;

$R^{k1}$ is hydrogen or $C_1$–$C_4$ alkyl;

$R^{k2}$ is phenyl or substituted phenyl, wherein each of the substituents on substituted phenyl is independently halogen, cyano, $C_1$–$C_4$ alkyl, fluorinated $C_1$–$C_4$ alkyl, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each X is independently hydrogen, fluorine, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$;

each Y1 is independently hydrogen, fluorine, cyano, methyl, ethyl, $CF_3$, methoxy, ethoxy, $OCF_3$, $CO_2CH_{13}$, $CH_2CO_2CH_3$, $(CH_2)_{1-4}OCH_3$, or $(CH_2)_{1-4}OCF_3$;

n is an integer from 3 to 5;

is 0 or 1;

s1 is an integer from 0 to 3; and s2 is an integer from 0 to 2;

or a pharmaceutically acceptable salt thereof.

An aspect of the preceding class is a compound of formula (VIII), wherein

E is $CR^aR^b$;

and all other variables are as defined in the fourth class;

or a pharmaceutically acceptable salt thereof.

Exemplary of compounds of the fifth embodiment is 1-[4-[4-(2-keto-1-benzimidazolinyl)piperidin-1-yl]butylaminocarbonyl]-6-phenylpiperidin-2-one, or a pharmaceutically acceptable salts thereof.

The present invention also includes a pharmaceutical composition comprising a therapeutically effective amount of any of the compounds described above and a pharmaceutically acceptable carrier. In one embodiment is a pharmaceutical composition made by combining any of the compounds described above and a pharmaceutically acceptable carrier. The present invention further includes a process for making a pharmaceutical composition comprising combining any of the compounds described above and a pharmaceutically acceptable carrier.

The present invention further includes a pharmaceutical composition as described in the preceding paragraph further comprising a therapeutically effective amount of a testosterone 5-alpha reductase inhibitor. In one embodiment, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor), or a dual type 1 and type 2 testosterone 5-alpha reductase inhibitor. In another embodiment, the testosterone 5-alpha reductase inhibitor is a type 2 testosterone 5-alpha reductase inhibitor. The testosterone 5-alpha reductase inhibitor is suitably finasteride.

The present invention also includes a method of treating benign prostatic hyperplasia in a subject in need thereof which comprises administering to the subject a therapeutically effective amount of any of the compounds (or any of the compositions) described above. In one embodiment of the method of treating BPH, the compound (or composition) does not cause a fall in blood pressure at dosages effective to alleviate BPH. In another embodiment of the method of treating BPH, the compound is administered in combination with a testosterone 5-alpha reductase inhibitor. A suitable testosterone 5-alpha reductase inhibitor for use in the method is finasteride.

The present invention also includes a method of inhibiting contraction of prostate tissue or relaxing lower urinary tract tissue in a subject in need thereof which comprises administering to the subject a therapeutically effective amount of any of the compounds (or any of the compositions) described above. In one embodiment of the method of inhibiting contraction of prostate tissue or relaxing lower urinary tract tissue, the compound (or composition) additionally does not cause a fall in blood pressure at dosages effective to inhibit contraction of prostate tissue. In another embodiment, the compound is administered in combination with a therapeutically effective amount of a testosterone 5-alpha reductase inhibitor; the testosterone 5-alpha reductase inhibitor is suitably finasteride.

The present invention also includes a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see Vatz, *Headache* (1997), 37: 107–108) and cardiac arrhythmia.

The present invention also includes a method of preventing or treating prostatic cancer which comprises administering to a subject in need of prevention or treatment thereof a therapeutically effective amount of a combination comprising any of the compounds (or compositions) described above and a testosterone 5-alpha-reductase inhibitor. The testosterone 5-alpha reductase inhibitor is suitably finasteride.

The present invention also includes the use of any of the compounds described above in the preparation of a medicament for: a) treating benign prostatic hyperplasia; b) relaxing lower urinary tract tissue; or c) inhibiting contraction of prostate tissue; in a subject in need thereof.

The present invention further includes the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

As used herein, the term "$C_1$–$C_6$ alkyl" means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" mea ns n-, iso-, sec- and t-butyl, n- and isopropyl, ethyl and methyl.

The term "$C_1$–$C_6$ alkoxy" means an —O-alkyl group wherein alkyl is $C_1$ to $C_6$ alkyl. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy.

The term "$C_2$–$C_8$ alkoxyalkyl" means a linear or branched $C_1$–$C_6$ alkyl group as defined above having as a substituent a $C_1$–$C_6$ alkoxy group as defined above, wherein the alkoxyalkyl group has a total of from 2 to 8 carbon atoms. Representative examples of suitable alkoxyalkyl groups include, but are not limited to, the $C_1$–$C_6$ alkoxy-substituted methyl groups (methoxymethyl, ethoxymethyl, n-propoxymethyl, isopropoxymethyl, and the butyloxymethyl, pentyloxymethyl, and hexyloxymethyl isomers), and the $C_1$–$C_6$ alkoxy-substituted ethyl groups. Other suitable alkoxyalkyl groups include the series $(CH_2)_{1-6}OCH_3$, $(CH_2)_{1-4}OCH_3$, $(CH_2)_{1-6}OCH_2CH_3$, and $(CH_2)_{1-4}OCH_2CH_3$.

The term "$C_3$–$C_8$ cycloalkyl" means a cyclic ring of an alkane having three to eight total carbon atoms (i.e., cyclopropyl, cyclobutyl, cyclopentyl, cyclohexyl, cycloheptyl or cyclooctyl). The term "$C_3$–$C_6$ cycloalkyl" refers to a cyclic ring selected from cyclopropyl, cyclobutyl, cyclopentyl, and cyclohexyl. "$C_4$–$C_6$ cycloalkyl" has an analogous meaning.

The term "$C_4$–$C_{20}$ alkylcycloalkyl" means a $C_3$–$C_8$ cycloalkyl as defined above substituted with one or more $C_1$–$C_8$ alkyl groups as defined above, wherein the total number of carbon atoms in the alkylcycloalkyl group is in the range of from 4 to 20. "$C_6$–$C_{14}$ alkylcycloalkyl" means a $C_3$–$C_6$ cycloalkyl as defined above substituted with one or more $C_1$–$C_4$ alkyl groups as defined above, wherein the total number of carbon atoms in the alkylcycloalkyl group is in the range of from 6 to 14. Representative examples include methylcyclohexyl (i.e., 2-, 3- and 4-methylcyclohexyl), ethylcyclohexyl, methylcyclopentyl, dimethylcyclohexyl (i.e., 2,3-, 2,4-, 2,5-, 2,6-, 3,4-, and 3,5-dimethylcyclohexyl), methylcyclobutyl, and so forth.

The term "$C_4$–$C_{20}$ cycloalkylalkyl" means a $C_1$–$C_8$ alkyl group as defined above substituted with one or more $C_3$–$C_8$ cycloalkyls as defined above, wherein the total number of carbon atoms in the cycloalkyl alkyl group is in the range of from 4 to 20. "$C_6$–$C_{14}$ cycloalkyl-alkyl" means a $C_1$–$C_4$ alkyl group as defined above substituted with one or more $C_3$–$C_6$ cycloalkyl groups as defined above, wherein the total number of carbon atoms in the alkylcycloalkyl group is in the range of from 5 to 14. Representative examples include cyclohexylmethyl, 1- and 2-cyclohexylethyl, cyclohexylisopropyl, 1- and 3-cyclohexyl-n-propyl, dicyclohexylmethyl, and so forth.

The term "halogen" (which may alternatively be referred to as "halo") refers to fluorine, chlorine, bromine and iodine (alternatively, fluoro, chloro, bromo, and iodo).

The term "fluorinated $C_1$–$C_6$ alkyl" (which may alternatively be referred to as "$C_1$–$C_6$ fluoroalkyl") means a $C_1$ to $C_6$ linear or branched alkyl group as defined above with one or more fluorine substituents. The term "fluorinated $C_1$–$C_4$ alkyl" has an analogous meaning. Representative examples of suitable fluoroalkyls include the series $(CH_2)_{0-4}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "fluorinated $C_3$–$C_8$ cycloalkyl" (which may alternatively be referred to as "$C_3$–$C_8$ fluorocycloalkyl") means a cycloalkyl group as defined above with one or more fluorine substituents. The terms "fluorinated $C_3$–$C_7$ cycloalkyl" and "fluorinated $C_3$–$C_6$ cycloalkyl" have analogous meanings. Representative examples of suitable fluorocycloalkyls include all isomers of fluorocyclohexyl (i.e., 1-, 2-, 3-, and 4-fluorocyclohexyl), difluorocyclohexyl (e.g., 2,4-difluorocyclohexyl, 3,4-difluorocyclohexyl, etc.), fluorocyclopentyl, and so forth.

The term "fluorinated $C_1$–$C_6$ alkoxy" (which may alternatively be referred to as "$C_1$–$C_6$ fluoroalkoxy") means a $C_1$–$C_6$ alkoxy group as defined above wherein the alkyl moiety has one or more fluorine substituents. The term "fluorinated $C_1$–$C_4$ alkoxy" has an analogous meaning. Representative examples include the series $O(CH_2)_{0-4}CF_3$ (i.e., trifluoromethoxy, 2,2,2-trifluoroethoxy, 3,3,3-trifluoro-n-propoxy, etc.), 1,1,1,3,3,3-hexafluoroisopropoxy, and so forth.

The term "fluorinated $C_2$–$C_8$ alkoxyalkyl" means $C_2$–$C_8$ alkoxyalkyl as defined above, wherein either or both the alkoxy moiety and the alkyl moiety has one or more fluorine substituents. Representative examples of suitable fluorinated alkoxyalkyl groups include, but are not limited to, the $C_1$–$C_6$ fluoroalkoxy-substituted methyl groups (e.g., fluoromethoxymethyl, 2-fluoroethoxymethyl, and 3-fluoro-n-propoxymethyl), $C_1$–$C_6$ difluoroalkoxymethyl groups (e.g., difluoromethoxymethyl and 2,2-difluoroethoxymethyl), $C_1$–$C_6$ trifluoroalkoxy-substituted methyl groups (e.g., trifluoromethoxymethyl and 2,2,2-trifluoroethoxymethyl), $C_1$–$C_6$ alkoxy-substituted fluoromethyl groups (e.g., methoxy- or ethoxy-fluoromethyl), and $C_1$–$C_6$ alkoxy-substituted difluoromethyl groups (e.g., methoxy- or ethoxy-difluoromethyl). Other suitable fluorinated alkoxyalkyl groups include the series $(CH_2)_{1-6}OCF_3$, $(CH_2)_{1-4}OCF_3$, $(CH_2)_{1-6}OCH_2CF_3$, and $(CH_2)_{1-4}OCH_2CF_3$.

The term "fluorinated $C_4$–$C_{20}$ alkylcycloalkyl" means a $C_4$–$C_{20}$ alkylcycloalkyl group as defined above having one or more fluorine substituents on either the $C_3$–$C_8$ cycloalkyl moiety or on the $C_1$–$C_6$ alkyl moiety (or on at least one $C_1$–$C_6$ alkyl if more than one are present) or on both cycloalkyl and alkyl moieties. Suitable groups include, but are not limited to, trifluoromethylcyclopropyl, trifluoromethylcyclohexyl (e.g., 4-trifluoromethylcyclohexyl), (2,2,2-trifluoroethyl)cyclopentyl, trifluoromethylfluorocyclohexyl (e.g., 4-trifluoromethyl-2-fluorocyclohexyl), and the like.

The term "fluorinated $C_4$–$C_{20}$ cycloalkylalkyl" means a $C_4$–$C_{20}$ cycloalkylalkyl group as defined above having one or more fluorine substituents on either the $C_1$–$C_6$ alkyl moiety or on the $C_3$–$C_8$ cycloalkyl moiety (or on at least one $C_3$–$C_8$ cycloalkyl if more than one are present) or on both alkyl and cycloalkyl moieties. Suitable groups include, but are not limited to, fluorocyclopropylmethyl, cyclopropyldifluoromethyl, difluorocyclohexylethyl (e.g.,2-(2,4-difluorocyclohexyl)ethyl), and the like.

The term "heterocyclic" (which may alternatively be referred to as "heterocycle") refers to a stable 5- to 7-membered monocyclic ring system which may be saturated or unsaturated; which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any single heteroatom or carbon atom, or with respect to the definitions of $D^1$ and $D^2$ may be fused to another ring system by two adjacent ring carbon atoms, provided that attachment or fusion results in the creation of a stable structure. Suitable heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxadiazolyl, triazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. Morpholino is the same as morpholinyl.

The term "thienyl," as used herein, refers to the group

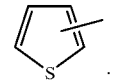

"Fused thienyl" refers to

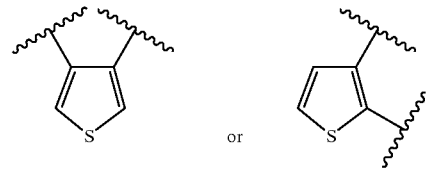

wherein the "open" bonds represent another ring system.

The term "substituted heterocyclic" refers to a heterocyclic group as defined above having one or more subsituents independently selected from halogen, cyano, $C_1$–$C_6$ alkyl, fluorinated $C_1$–$C_6$ alkyl, $C_1$–$C_6$ alkoxy, fluorinated $C_1$–$C_6$ alkoxy, $C_2$–$C_8$ alkoxyalkyl, fluorinated $C_2$–$C_8$ alkoxyalkyl, $C_3$–$C_8$ cycloalkyl, fluorinated $C_3$–$C_8$ cycloalkyl, amino, N-($C_1$–$C_6$ alkyl)amino, N,N-di-($C_1$–$C_6$ alkyl)amino, aryl (defined below), carboxy, $C_1$–$C_6$ alkoxycarbonyl, sulfonamido,sulfonyl, and the like.

The term "aryl" refers herein to aromatic mono- and poly-carbocyclic ring systems, wherein the carbocyclic rings in the polyring systems may be fused or attached via a single ring carbon. Suitable aryl groups include, but are not limited to, phenyl, naphthyl, and biphenylenyl.

"Substituted aryl" refers to aryl groups as defined above having one or more substituents independently selected from halogen, cyano, $C_1$–$C_6$ alkyl, fluorinated $C_1$–$C_6$ alkyl, $C_1$–$C_6$ alkoxy, fluorinated $C_1$–$C_6$ alkoxy, $C_2$–$C_8$ alkoxyalkyl, fluorinated $C_2$–$C_8$ alkoxyalkyl, $C_3$–$C_8$ cycloalkyl, fluorinated $C_3$–$C_8$ cycloalkyl, amino, N—$C_1$–$C_6$ alkylamino, N,N-di-($C_1$–$C_6$)alkylamino, aryl, carboxy, $C_1$–$C_6$ alkoxycarbonyl, sulfonamido, sulfonyl, and the like.

The term "heteroaryl" refers to the subset of heterocycles as heretofore defined which are aromatic heterocyclic ring systems, including, but not limited to, pyridyl, pyrazinyl, thienyl, thiazolyl, furanyl, imidazolyl, pyrazolyl, triazolyl, oxazolyl, oxadiazolyl, thiazolyl, and thiadiazolyl.

"Substituted heteroaryl" refers to heteroaryl groups as defined above having one or more substituents as defined above.

The term "substituted" includes mono- and poly-substitution by a named substituent to the extent such single and multiple substitution is chemically allowed.

The expression "Z is absent" means that Z is replaced by a bond; i.e., ring $D^1$ is fused to a cyclopentyl moiety in groups (a9) and (a10) of Formula (I).

It is understood that the definition of a substituent (e.g., $CO_2R^d$) or variable (e.g., $R^d$) at a particular location in a molecule is independent of its definitions at other locations in that molecule. Thus, for example, when $R^2$ is $CO_2R^d$=$CO_2H$, and $R^4$ is also $CO_2R^d$, it is understood that $R^4$ can be any one of $CO_2H$, $CO_2Me$, $CO_2Et$, $CO_2Pr$, etc. As another example, the moiety

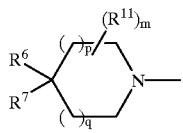

wherein $R^{11}$ is hydrogen or $C_1$-$C_4$ alkyl, p=1, q=1, and m=2, represents moieties such as

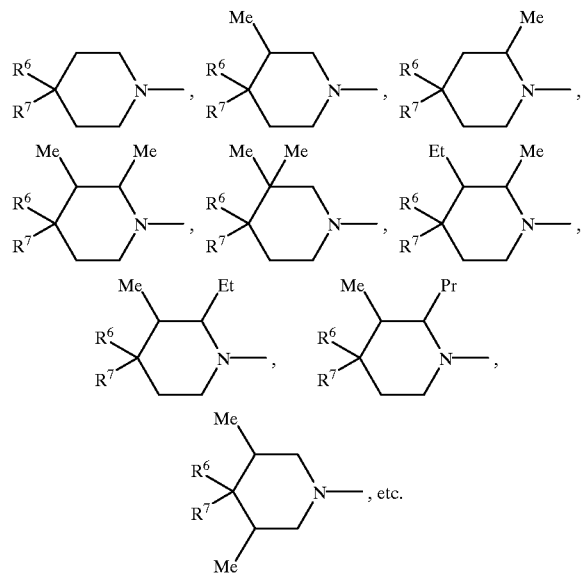

It is also understood that the definition of a substituent or variable at a particular location in a molecule is independent of the definition of another occurrence of the same substituent or variable at the same location. Thus, $C(=O)N(R^e)_2$ represents groups such as —$C(=O)NH_2$, —$C(=O)NHCH_3$, —$C(=O)NHC_2H_5$, —$C(=O)N(CH_3)C_2H_5$, etc.

It is understood that substituents and substitution patterns on the compounds of the instant invention can be selected by one of ordinary skill in the art to provide compounds that are chemically stable and that can be readily synthesized by the methods set forth below and, when viewed in the light of this disclosure, by techniques known in the art. Where multiple substituent moieties are disclosed or claimed, the substituted compound can be independently substituted by one or more of the disclosed or claimed substituent moieties, singly or plurally.

Representative embodiments for the variables and substituents set forth in Formula (I) include the following:

$R^1$ is hydrogen, $C_1$-$C_4$ alkyl, or fluorinated $C_1$-$C_4$ alkyl; or is hydrogen, $C_1$-$C_4$ alkyl, or $(CH_2)_{0-4}CF_3$; or is hydrogen.

$R^2$ and $R^3$ are each independently selected from hydrogen, cyano, $C_1$-$C_4$ alkyl, $(CH_2)_{0-4}CF_3$, $C_3$-$C_6$ cycloalkyl, fluorinated $C_3$-$C_6$ cycloalkyl, $(CH_2)_{0-4}CO_2R^d$, $(CH_2)_{0-4}OR^d$, and $(CH_2)_{0-4}CON(R^d)_2$; or are each independently selected from hydrogen, cyano, methyl, ethyl, $CF_3$, $CH_2CF_3$, $C_3$-$C_6$ cycloalkyl, $CO_2CH_3$, $CH_2CO_2CH_3$, $OCH_3$, $CH_2OCH_3$, $CONH_2$, and $CH_2CONH_2$. In another embodiment, $R^2$ and $R^3$ are each independently selected from hydrogen, methyl, ethyl, and cyclopropyl; or $R^2$ and $R^3$ together with the carbon atom to which they are attached form $C_4$-$C_6$ cycloalkyl (e.g., cyclohexyl).

$R^4$ and $R^5$ are each independently selected from hydrogen, $C_1$-$C_4$ alkyl, $(CH_2)_{0-4}CF_3$, $C_3$-$C_6$ cycloalkyl, fluorinated $C_3$-$C_6$ cycloalkyl, and $(CH_2)_{0-4}OR^d$; or are each independently selected from hydrogen, methyl, ethyl, $CF_3$, $CH_2CF_3$, $C_3$-$C_6$ cycloalkyl, $OCH_3$, $CH_2OCH_3$, $OCF_3$, $CH_2OCF_3$; or are each independently selected from hydrogen, methyl, and ethyl.

$R^6$ is hydrogen, cyano, hydroxy, $CO_2R^e$, $CON(R^e)_2$, phenyl, or substituted phenyl; or is hydrogen, cyano, hydroxy, $CO_2R^e$, $CON(R^e)_2$, phenyl, or mono- or di- or tri-substituted phenyl; or is hydrogen or cyano.

When $R^6$ is substituted phenyl, each of the substituents on substituted phenyl is independently halo, cyano, hydroxy, $C_1$-$C_6$ alkyl, fluorinated $C_1$-$C_6$ alkyl, $C_3$-$C_8$ cycloalkyl, fluorinated $C_3$-$C_8$ cycloalkyl, $C_1$-$C_6$ alkoxy, fluorinated $C_1$-$C_6$ alkoxy, $(CH_2)_{0-4}CO_2R^d$, $C_2$-$C_8$ alkoxyalkyl, or fluorinated $C_2$-$C_8$ alkoxyalkyl; or each is independently fluorine, chlorine, cyano, hydroxy, methyl, ethyl, $CF_3$, $OCH_3$, $(CH_2)_{1-2}OCH_3$, or $(CH_2)_{1-2}OCF_3$, $CO_2CH_3$, or $CH_2CO_2CH_3$.

$R^7$ is phenyl, substituted phenyl, naphthyl, or substituted naphthyl; or pyridyl, pyrazinyl, thienyl, or furanyl; or substituted pyridyl, pyrazinyl, thienyl, or furanyl. In embodiments, $R^7$ is phenyl, mono- or di- or tri-substituted phenyl, pyridyl, pyrazinyl, substituted pyridyl, or substituted pyrazinyl; or is phenyl, substituted phenyl, or pyridyl.

When $R^7$ is substituted aryl (e.g., substituted phenyl or substituted naphthyl), each of the substituents is independently halo, cyano, hydroxy, $C_1$-$C_6$ alkyl, fluorinated $C_1$-$C_6$ alkyl, $C_3$-$C_8$ cycloalkyl, fluorinated $C_3$-$C_8$ cycloalkyl, $C_1$-$C_6$ alkoxy, fluorinated $C_1$-$C_6$ alkoxy, $(CH_2)_{0-4}CO_2R^d$, $C_2$-$C_8$ alkoxyalkyl, or fluorinated $C_2$-$C_8$ alkoxyalkyl; or is independently chlorine, fluorine, $C_1$-$C_4$ alkyl, $(CH_2)_{0-3}CF_3$, $C_1$-$C_4$ alkoxy, $OCF_3$, $(CH_2)_{0-4}CO_2CH_3$, $(CH_2)_{1-3}OCH_3$, or $(CH_2)_{1-3}OCF_3$; or is independently hydrogen, halogen, or cyano.

When $R^7$ is substituted heterocyclic (e.g., substituted pyridyl, pyrazinyl, thienyl, or furanyl), each of the substituents is independently halogen, cyano, $N(R^d)_2$, $(CH_2)_{0-4}C(=O)N(R^d)2$, $(CH_2)_{0-4}SO_2N(R^d)_2$, $(CH_2)_{0-4}SO_2R^d$, phenyl, $C_1$-$C_6$ alkyl, fluorinated $C_1$-$C_6$ alkyl, $C_3$-$C_8$ cycloalkyl, fluorinated $C_3$-$C_8$ cycloalkyl, $C_1$-$C_6$ alkoxy, fluorinated $C_1$-$C_6$ alkoxy, $(CH_2)_{04}CO_2R^d$, $C_2$-$C_8$ alkoxyalkyl, or fluorinated $C_2$-$C_8$ alkoxyalkyl; or is independently chlorine, fluorine, $C_1$-$C_4$ alkyl, $(CH_2)_{0-3}CF_3$, $C_1$-$C_4$ alkoxy, $OCF_3$, $(CH_2)_{0-4}CO_2CH_3$, $(CH_2)_{1-3}OCH_3$, or $(CH_2)_{1-3}OCF_3$; or is independently halogen or cyano.

$R^8$ is hydrogen, methyl or ethyl; or is hydrogen.

One of $R^9$ and $R^{10}$ is hydrogen, and the other of $R^9$ and $R^{10}$ is hydrogen or $C_1$-$C_6$ alkyl (e.g., hydrogen, methyl, or ethyl). In another embodiment, $R^9$ and $R^{10}$ are both hydrogen.

Each $R^{11}$ is a substituent connected to a ring atom other than $CR^6R^7$ or N and is independently hydrogen, methyl or ethyl.

$R^{12}$ is hydrogen, $C_1$-$C_4$ alkyl, $(CH_2)_{0-4}CF_3$, $C_3$-$C_6$ cycloalkyl, or fluorinated $C_3$-$C_6$ cycloalkyl; or is hydrogen, methyl, ethyl, $CF_3$, $CH_2CF_3$, or $C_3$-$C_6$ cycloalkyl.

$R^{14}$ is hydrogen or hydroxy; or is hydrogen.

Each $R^{16}$ is a substituent connected to a ring atom other than $CR^6R^7$ or N and is independently hydrogen, methyl or ethyl.

Each $R^{18}$ is a substituent connected to a ring atom other than $CR^6R^7$ or N and is independently hydrogen, methyl or ethyl.

$D^1$ is a benzene ring, substituted benzene ring, heteroaryl, or substituted heteroaryl;

$D^1$ is a benzene ring (i.e., benzo), substituted benzene ring (i.e., substituted benzo), heteroaryl, or substituted heteroaryl, wherein the heteroaryl has from 1 to 2 heteroatoms selected from N, O and S; or $D^1$ is benzo or mono- or di- or tri-substituted benzo, wherein each of the substituents on substituted benzo is independently halogen, cyano, $C_1$–$C_8$ alkyl, $C_3$–$C_8$ cycloalkyl, fluorinated $C_1$–$C_8$ alkyl, fluorinated $C_3$–$C_8$ cycloalkyl, $C_1$–$C_6$ alkoxy, fluorinated $C_1$–$C_6$ alkoxy, $C_2$–$C_8$ alkoxyalkyl, or fluorinated $C_2$–$C_8$ alkoxyalkyl; or $D^1$ is heteroaryl or substituted heteroaryl, wherein the heteroaryl has 1 to 2 N atoms and the remaining atoms in the heteroaryl ring are carbon atoms, and each of the substituents on substituted heteroaryl is as previously set forth in this paragraph for substituted benzo; or $D^1$ is 6-membered heteroaryl or substituted 6-membered heteroaryl, wherein each of the substituents on substituted heteroaryl is as set forth earlier in this paragraph for substituted benzo.

$D^2$ independently has the same definition as set forth for $D^1$. In one embodiment, one of $D^1$ and $D^2$ is benzo or substituted benzo, and the other of $D^1$ and $D^2$ is heteroaryl or substituted heteroaryl. In another embodiment, each of $D^1$ and $D^2$ is independently benzo or substituted benzo. In an aspect of the preceding embodiment, $D^1$ is

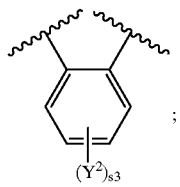

and $D^2$ is

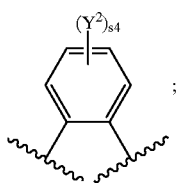

wherein each $Y^2$ is independently hydrogen, halogen, cyano, nitro, $C_1$–$C_8$ alkyl, $C_3$–$C_8$ cycloalkyl, fluorinated $C_1$–$C_8$ alkyl, fluorinated $C_3$–$C_8$ cycloalkyl, $C_2$–$C_8$ alkoxyalkyl, or fluorinated $C_2$–$C_8$ alkoxyalkyl; and s3 and s4 are each independently integers from 0 to 4. In one aspect of this embodiment, each $Y^2$ is independently hydrogen, halogen, $C_1$–$C_4$ alkyl, $(CH_2)_{0-4}CF_3$, $C_1$–$C_4$ alkoxy, $OCF_3$, $CO_2R^d$, $(CH_2)_{1-4}OCH_3$, or $(CH_2)_{1-4}OCF_3$. In other aspects, s3 and s4 are each independently integers from 0 to 3; or from 0 to 2.

Z is absent, O, S, SO, $SO_2$, $NR^h$, $C(R^fR^g)$, or $C(R^fR^g)C(R^fR^g)$; or is absent, O, S, SO, $SO_2$, $CH_2$, or $CH_2CH_2$.

Q is absent, $[C(R^{a\prime}R^{b\prime})]_{1-4}$, $O[C(R^{a\prime}R^{b\prime})]_{1-2}$, $[C(R^{a\prime}R^{b\prime})]_{1-2}O$, or $C(R^{a\prime})$=$C(R^{b\prime})$; or Q is absent, $[C(R^{a\prime}R^{b\prime})]_{1-4}$, or $[C(R^{a\prime}R^{b\prime})]_{1-2}O$; or Q is absent or $(CH_2)_{1-4}$.

T is absent, C(=O), C(=O)O, $N(SO_2R^{c\prime})C(R^{a\prime}R^{b\prime})$, $N(R^{c\prime})C$=O, or $N(R^{c\prime})C$(=O)O, provided that (i) when T is absent, Q is $[C(R^{a\prime}R^{b\prime})]_{2-4}$, $O[C(R^{a\prime}R^{b\prime})]_{1-2}$, $[C(R^{a\prime}R^{b\prime})]_{1-2}O$, or $C(R^{a\prime})$=$C(R^{b\prime})$; (ii) when T is C(=O) or C(=O)O, Q is $C(R^{a\prime}R^{b\prime})$ or $C(R^{a\prime}R^{b\prime})C(R^{a\prime}R^{b\prime})$; and (iii) when T is $N(SO_2R^{c\prime})C(R^{a\prime}R^{b\prime})$, $N(R^{c\prime})C$=O, or $N(R^{c\prime})C$(=O)O, Q is absent or $C(R^{a\prime}R^{b\prime})$.

Spirobicyclic groups representing particular combinations of Q and T include the following:

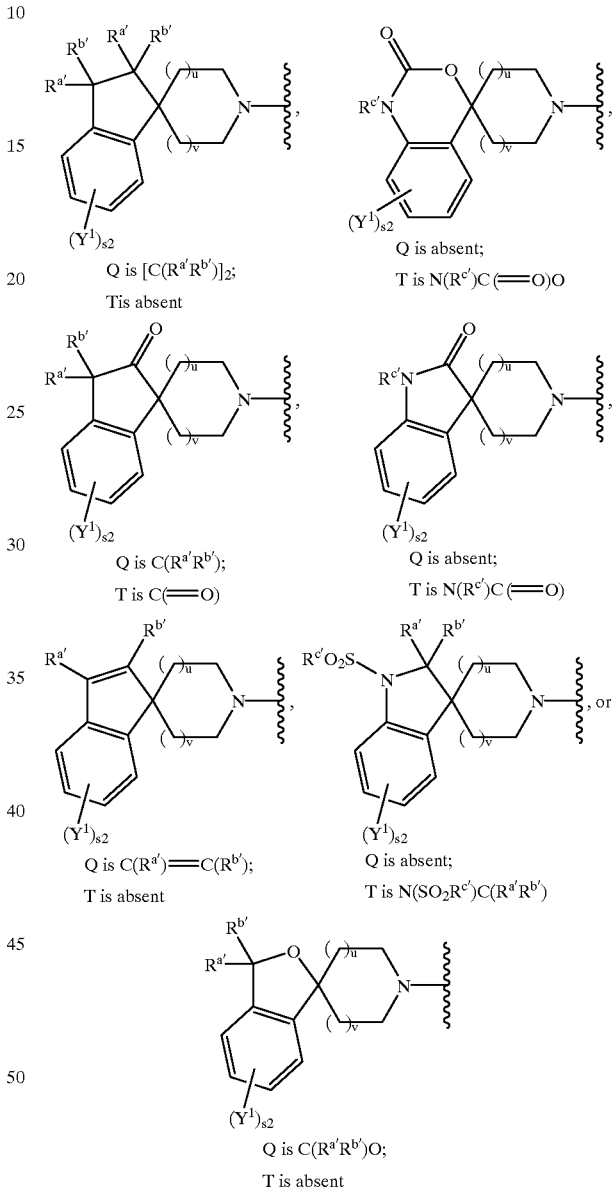

Each X is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$; or is independently hydrogen, fluorine, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$; or is independently hydrogen or fluorine.

Each $Y^1$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$; or is independently hydrogen, fluorine, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$; or is independently hydrogen, fluorine, or cyano.

$R^a$ and $R^b$ are each independently selected from hydrogen, $C_1$–$C_4$ alkyl, $(CH_2)_{0-4}CF_3$, $C_3$–$C_6$ cycloalkyl, and fluorinated $C_3$–$C_6$ cycloalkyl; or are each independently selected from hydrogen, methyl, and ethyl; or are each independently selected from hydrogen and methyl.

$R^c$ is hydrogen, $C_1$–$C_4$ alkyl, $(CH_2)_{0-4}CF_3$, $C_3$–$C_6$ cycloalkyl, fluorinated $C_3$–$C_6$ cycloalkyl, or $CHR^{k1}R^{k2}$; or is hydrogen, methyl, ethyl, benzyl, or α-methylbenzyl.

$R^{a'}$, $R^{b'}$ and $R^{c'}$ are each independently selected from hydrogen, $C_1$–$C_4$ alkyl, and $(CH_2)_{0-4}CF_3$; or are each independently selected from hydrogen, methyl, ethyl, or $CF_3$; or are each independently selected from hydrogen and methyl. In another embodiment, each of $R^{a'}$ and $R^{b'}$ is hydrogen, and $R^{c'}$ is hydrogen or methyl.

$R^d$ is hydrogen, $C_1$–$C_4$ alkyl, or $(CH_2)_{0-4}CF_3$; or is hydrogen, methyl, ethyl, or $CF_3$.

One of $R^f$ and $R^g$ is hydrogen, and the other of $R^f$ and $R^g$ is hydrogen, $C_1$–$C_4$ alkyl, $C_3$–$C_6$ cycloalkyl, fluorinated $C_1$–$C_4$ alkyl, phenyl, or substituted phenyl, wherein each of the substituents on the substituted phenyl is independently halogen, $C_1$–$C_4$ alkyl, fluorinated $C_1$–$C_4$ alkyl, $C_1$–$C_4$ alkoxy, fluorinated $C_1$–$C_4$ alkoxy, $CO_2R^d$, $C_2$–$C_8$ alkoxyalkyl, or fluorinated $C_2$–$C_8$ alkoxyalkyl. In another embodiment, $R^f$ and $R^g$ are both hydrogen.

$R^e$ is hydrogen, $C_1$–$C_4$ alkyl, $C_3$–$C_6$ cycloalkyl, or fluorinated $C_1$–$C_4$ alkyl; or is hydrogen, $C_1$–$C_4$ alkyl, or $(CH_2)_{0-4}CF$; or is hydrogen, methyl, or ethyl; or is hydrogen.

$R^h$ is hydrogen, $C_1$–$C_4$ alkyl, fluorinated $C_1$–$C_4$ alkyl, $C_3$–$C_6$ cycloalkyl, fluorinated $C_3$–$C_6$ cycloalkyl, $C_6$–$C_{14}$ alkylcycloalkyl, or $C_6$–$C_{14}$ cycloalkylalkyl; or is hydrogen, $C_1$–$C_4$ alkyl, or $(CH_2)_{0-4}CF_3$; or is hydrogen, methyl, ethyl, or $CF_3$; or is hydrogen.

$R^{k1}$ is hydrogen or $C_1$–$C_4$ alkyl; or is hydrogen, methyl, or ethyl.

$R^{k2}$ is phenyl or substituted phenyl, wherein each of the substituents on substituted phenyl is halogen, cyano, $C_1$–$C_4$ alkyl, fluorinated $C_1$–$C_4$ alkyl, $C_1$–$C_4$ alkoxy, $OCF_3$, $(CH_2)_{0-4}CO_2R^d$, $(CH_2)_{1-4}OCH_3$, or $(CH_2)_{1-4}OCF_3$.

m is an integer from 0 to 2; or is 1; or is 0.

n is an integer from 2 to 5; or from 3 to 5; or is 3; or is 4.

p and q are each integers from 0 to 3. provided that the sum of p+q is an integer less than or equal to 3. In another embodiment p and q are each independently integers from 0 to 1. In still another embodiment p and q are both 1.

s1 is an integer from 0 to 3; or from 0 to 2; or is 0 or 1.

s2 is an integer from 0 to 3; or from 0 to 2; or is 0 or 1.

t is an integer from 0 to 2, provided that when t is zero, $R^{14}$ is hydrogen. In another embodiment, t is zero and $R^{14}$ is hydrogen.

u and v are each integers from 0 to 3. provided that the sum of p+q is an integer less than or equal to 3. In another embodiment u and v are each independently integers from 0 to 1. In still another embodiment one of p and q is 1, and the other is 0.

w is an integer from 0 to 2; or is 1; or is 0.

The compounds of the present invention typically exhibit selectivity for the human alpha 1a adrenergic receptor. One implication of this selectivity is that these compounds display selectivity for lowering intraurethral pressure without substantially affecting diastolic blood pressure.

Representative compounds of this invention display submicromolar affinity for the human alpha 1a adrenergic receptor subtype while displaying lower affinity for the human alpha 1d and alpha 1b adrenergic receptor subtypes, and many other G-protein coupled human receptors. A class of the compounds of this invention exhibit nanomolar and subnanomolar affinity for the human alpha 1a adrenergic receptor subtype while displaying at least about 10 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors). In a subclass of the preceding class, the compounds of this invention exhibit nanomolar and subnanomolar affinity for the human alpha 1a adrenergic receptor subtype while displaying at least about 100-fold lower affinity for the human alpha 1d and alpha 1b adrenergic receptor subtypes, in addition to exhibiting selectivity over other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed; e.g., treatment of BPH. For use in medicine, the salts of the compounds of this invention refer to non-toxic "pharmaceutically acceptable salts." Other salts may, however, be useful in the preparation of the compounds according to the invention or in the prepartion of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, n-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Compounds of this invention are used to reduce the acute symptoms of BPH. Thus, compounds of this invention may be used alone or in combination with more long-term anti-BPH therapeutics, such as testosterone 5-a reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intraocular pressure, control of cardiac arrhythmias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "selective alpha 1a adrenergic receptor antagonist," as used herein, refers to an alpha 1a antagonist compound which exhibits selectivity (e.g., at least about ten fold selectivity) for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention includes pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" encompasses a product comprising the specified ingredients in the specified amounts, as well as any product which results, directly or indirectly, from combination of the specified ingredients in the specified amounts.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

The specificity of binding of compounds showing affinity for the alpha 1a receptor is shown by comparing affinity to membranes obtained from transfected cell lines that express the alpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. W094/08040, published Apr. 14, 1994 and WO 94/21660, published Sep. 29, 1994. The cloned human alpha 1a receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g., PCT International Application Publication No. W094/10989, published May 26, 1994; U.S. Pat. No. 5403847, issued Apr. 4, 1995]. Compounds which are both selective amongst the various human alpha adrenergic receptor subtypes and which have low affinity for other receptors, such as the alpha 2 adrenergic receptors, the β-adrenergic receptors, the muscarinic receptors, the serotonin receptors, the histamine receptors, and others are particularly preferred. The absence of these non-specific activities may be confirmed by using cloned and expressed receptors in an analogous fashion to the method disclosed herein for identifying compounds which have high affinity for the various human alpha adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in which the novel compositions of the present invention may be incorporated for administration orally or by injection include aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin. Other dispersing agents which may be employed include glycerin and the like.

For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range; e.g., from about 0.01 to about 1000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to about 10 mg/kg of body weight per day, and especially from about 0.001 mg/kg to about 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this invention is administration of compounds of this invention and a human testosterone 5-a reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. No. 4,377,584 and U.S. Pat. No. 4,760,071, for example). In addition to PROSCAR®, which is principally active in prostatic tissue due to its selectivity for human 5-a reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5a-reductase inhibitors have been described in WO93/23420, EP 0572166; WO 93/23050; WO93/23038; WO93/23048; WO93/23041; WO93/23040; WO93/23039; WO93/23376; WO93/23419, EP 0572165; WO93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one embodiment of the present invention, a method of treating BPH is provided which comprises administering to a subject in need of treatment any of the compounds of the present invention in combination with finasteride effective to treat BPH. The dosage of finasteride administered to the subject is from about 0.01 mg per subject per day to about 50 mg per subject per day in combination with an alpha 1a antagonist. In one aspect, the dosage of finasteride in the combination is from about 0.2 mg per subject per day to about 10 mg per subject per day, and, in another aspect, from about 1 to about 7 mg per subject to day (e.g., about 5 mg per subject per day).

For the treatment of benign prostatic hyperplasia, compounds of this invention exhibiting alpha 1a adrenergic receptor blockade can be combined with a therapeutically effective amount of a 5a-reductase 2 inhibitor, such as finasteride, in addition to a 5a-reductase 1 inhibitor, such as 4,7β-dimethyl-4-aza-5a-cholestan-3-one, in a single oral, systemic, or parenteral pharmaceutical dosage formulation. Alternatively, a combined therapy can be employed wherein the alpha 1a adrenergic receptor antagonist and the 5a-reductase 1 or 2 inhibitor are administered in separate oral, systemic, or parenteral dosage formulations. See, e.g., U.S. Pat. No. 4,377,584 and U.S. Pat. No. 4,760,071 which describe dosages and formulations for 5a-reductase inhibitors.

Abbreviations used in the instant specification, particularly the Schemes and Examples, are as follows:

CDI=1,1-carbonyldiimidazole
DEA=diethylamine
DEAD=diethyl azodicarboxylate
DIBAH=diisobutyl aluminum hydride
DIEA=diisopropylethylamine
DMF=N,N-dimethylformamide
DPPA=diphenylphosphorylazide
EDC=1-(3-dimethylaminopropyl)-3-ethyl carbodiimide hydrochloride
EDTA=ethylenediamine tetraacetic acid
Et$_3$N=triethylamine
EtOAc=ethyl acetate
EtOH=ethanol
FAB MS=fast atom bombardment mass spectroscopy
HOBT=1-hydroxy benzotriazole hydrate
HPLC=high performance liquid chromatography
LAH=lithium aluminum hydride
LDA 32 lithium diisopropylamide
mCPBA=m-chloroperbenzoic acid
MeOH=methanol
m.p.=melting point
NCS=N-chlorosuccinimide NMR=nuclear magnetic resonance
Ph=phenyl
(p-NO$_2$Ph)OCOCl=p-nitrophenylchloroformate
Pr=propyl
TFA=trifluoroacetic acid
THF=tetrahydrofuran The compounds of the present invention can be readily prepared according to the following reaction schemes and examples, or modifications thereof, using readily available starting materials, reagents and conventional synthetic procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Many of the compounds claimed within this invention can be prepared via Schemes 1–9 shown below. Lactams (E=CR$^a$R$^b$) are prepared using procedures such as those outlined in Schemes 1 and 2. Thus, in Scheme 1, a 5-aryl-5-ketopentanoic acid is converted to the 5-oxime with hydroxylamine or a hydroxylamine derivative, then reduced, preferably by catalytic hydrogenation, to the 5-amino compound. The latter compound is cyclodehydrated by heating, either neat or in an inert medium, to give the lactam. Representative procedures for the overall transformation are given by Williams, *Biochem. Pharmacol.* 1974, 23: 616–617, and by Desaubry, Wermuth, and Bourguignon, *Tet. Lett.* 1995, 36: 4249–4252. The lactam is activated by treating with base followed by phosgene or a phosgene equivalent such as, for example, p-nitrophenylchloroformate. The resulting N-acyl lactam is converted to the final product by treatment with a nucleophilic group, AH.

Alternatively, as shown in Scheme 2, the lactam can be constructed from a 5-aryl-5-ketopentanoic acid ester. Thus, a substituted or unsubstituted glutaric anhydride is opened with an alcohol to the corresponding monoacid-monoester substituted alpha to the free acid group using the procedure described by Birch and Robinson, *J. Chem. Soc.* 1942, 488–497. Alternatively, the procedure of Hutchinson et al., *J. Med. Chem.* 1993, 36: 2771–2787, which involves opening to the diester followed by selective cleavage of one ester group, may be employed to obtain the monoacid-monoester substituted alpha to the ester group. Treatment of either acid-ester with a chlorinating reagent such as thionyl chloride, followed by N,O-dimethylhydroxylamine converts the free acid group to the N,O-dimethylhydroxyamide, also known as a Weinreb amide (Nahm and Weinreb, *Tet. Lett.* 1981, 22: 3815–3818). Treatment of the Weinreb amide with an arylmetal compound, such as an arylmagnesium halide or an aryllithium, using a procedure such as that described in the above-cited Nahm and Weinreb reference, provides the 5-aryl-5-ketopentanoic ester which, when reductively aminated with, for example, ammonium acetate and sodium cyanoborohydride, gives the amino ester which cyclizes spontaneously, or upon heating as above if necessary, to the lactam. This lactam is elaborated to the final product as described above.

Cyclic urea compounds (E=NR$^c$) are prepared as illustrated in Schemes 3–6. Thus, in Scheme 3, an aryl aldehyde is condensed with ammonium acetate and a substituted malonic acid by heating in, for example, refluxing ethanol, as described by Rault, Dallemagne, and Rooba, *Bull. Soc. Chim. Fr.* 1987, 1079–1083, and by Soloshonok et al., *Tetrahedron: Asymmetry* 1995, 6: 1601–1610. The resulting 3-aryl-3-aminoacid is protected with, for example, the Boc protecting group, then coupled with, for example, one enantiomer of alpha-methylbenzylamine using procedures known in the art. The resulting amides may be separated into their individual diastereomers by any of several techniques, such as crystallization or column chromatography. The individual diasteromers can be deprotected in an acid medium such as cold HCl/ethyl acteate or trifluoroacetic acid in dichloromethane, and the resulting amino amides can be reduced to the diamines with, for example, borane or a borane derivative (e.g., BH$_3$.THF in THF). With phosgene or a phosgene equivalent such as carbonyldiimidazole, the diamines can be cyclized to the cyclic ureas which can be activated and coupled with nucleophiles AH using the procedures described above and illustrated in Schemes 1 and 2 for lactams. The α-methylbenzyl group can be removed to give the final products by treatment with strong acid, such as trifluoroacteic acid (see, for example, Gramain, Mavel, Troin, and Vallee-Goyet, *Tet.* 1991, 35: 7287–7300), or by catalytic hydrogenation.

The cyclic ureas can also be constructed as shown in Scheme 4. Thus, condensation of an aryl aldehyde with an alkyl aldehyde and a substituted or unsubstituted urea by heating with formic acid according to the procedure of ten Hoeve and Wynberg (*Syn. Comm.* 1994, 24: 2215–2221) produces the cyclic urea directly. This is activated and coupled, and deprotected where necessary, as described above.

Alternatively, the cyclic ureas may be prepared as shown in Scheme 5 by condensing an aryl aldehyde with an alkyl carboxylic acid or its derivative (ester, dialkyl amide, etc.) using strong base such as LDA or lithium hexamethyldisilazide. See Black, DuBay, and Tully, *J. Org. Chem.* 1988, 53: 5922–5927 for a representative procedure. The resulting hydroxy acid or acid derivative may be converted to the amide using procedures known in the art, e.g., carbodiimide coupling of the hydroxyacid to the appropriate amine. The resulting hydroxyamide may be converted to the diamine by, for example, Mitsunobu conversion of the hydroxy group to azide followed by reduction of both the azide and the amide with borane or a borane derivative, catalytic hydrogenation, etc. Cyclization of the resulting diamine to the cyclic urea and elaboration to the final products by coupling to nucleophiles AH and deprotection, where necessary, are carried out as described above.

Alternatively, the cyclic ureas may be prepared as shown in Scheme 6. Aldol condensation of an alkyl aldehyde with an aryl aldehyde using procedures known in the art provides 3-hydroxyketones. These can by reduced with hydride reagents such as LAH or NABH$_4$, or combined with organometallic reagents to give 1,3-diols. These diols can be heated with substituted or unsubstituted ureas to give cyclic ureas. Alternatively, the 1,3-diols can be converted to 1,3-diazides using the Mitsunobu procedure cited above, and these 1,3-diazides can be reduced to 1,3-diamines which can then be cyclized with phosgene or a phosgene equivalent to provide the cyclic ureas. Alternatively, the 3-hydroxyketones can be reductively aminated with, for example, ammonium acetate and sodium cyanoborohydride to give 3-hydroxyamines. These can be protected as amide, carbamate, etc., converted to 3-azido-protected amines by the Mitsunobu procedure, then deprotected and reduced to the 1,3-diamine which can be cyclized as described above. The cyclic ureas are activated, coupled, and, where necessary, deprotected to give the final products using the procedures described above.

Schemes 7–9 provide the procedures employed to prepare the compounds of Examples 14, 18, and 21 respectively.
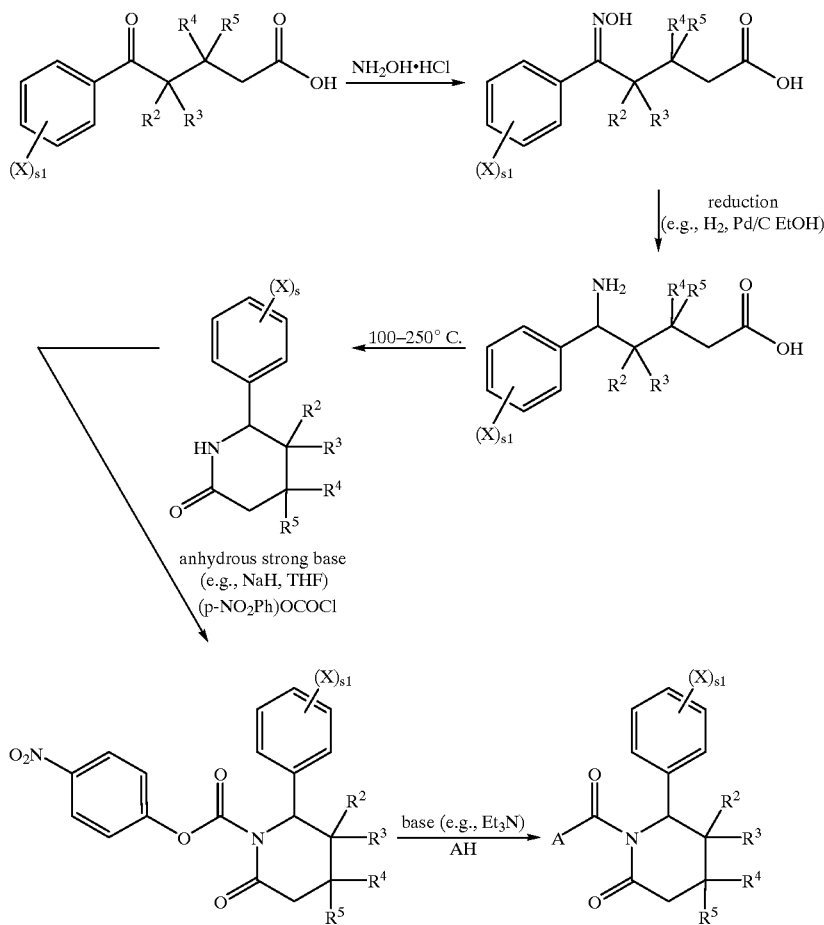
SCHEME 1
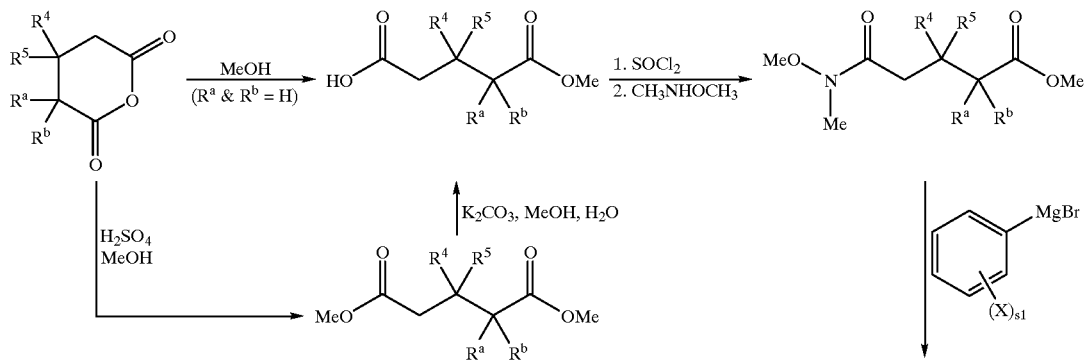
SCHEME 2

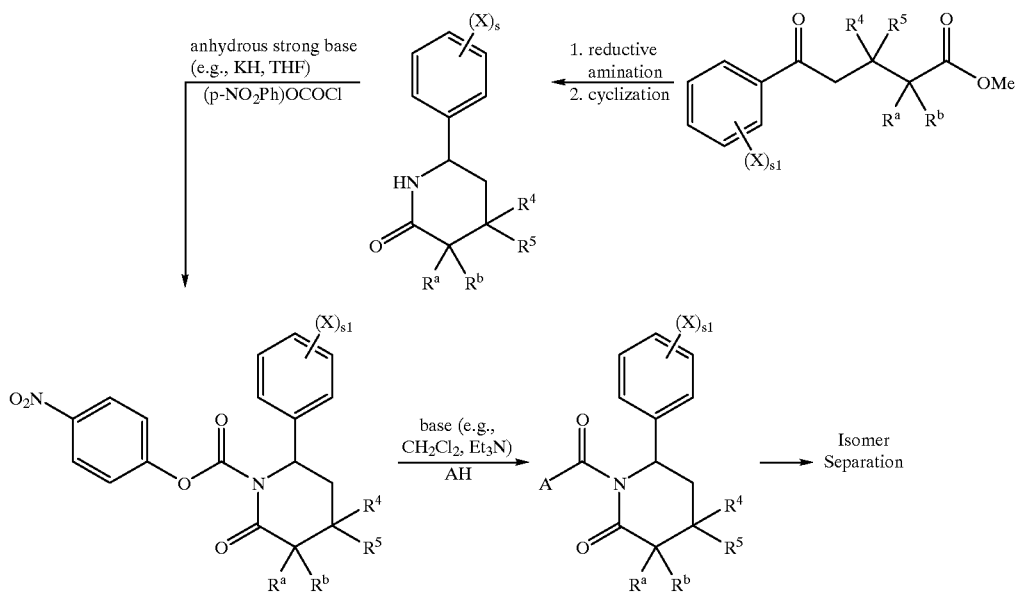
SCHEME 3
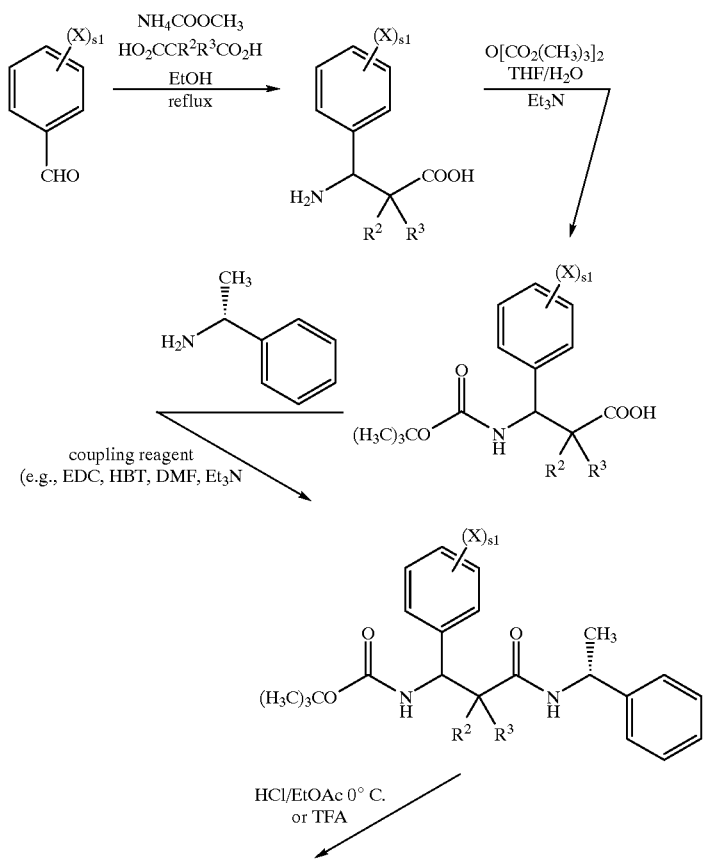

-continued
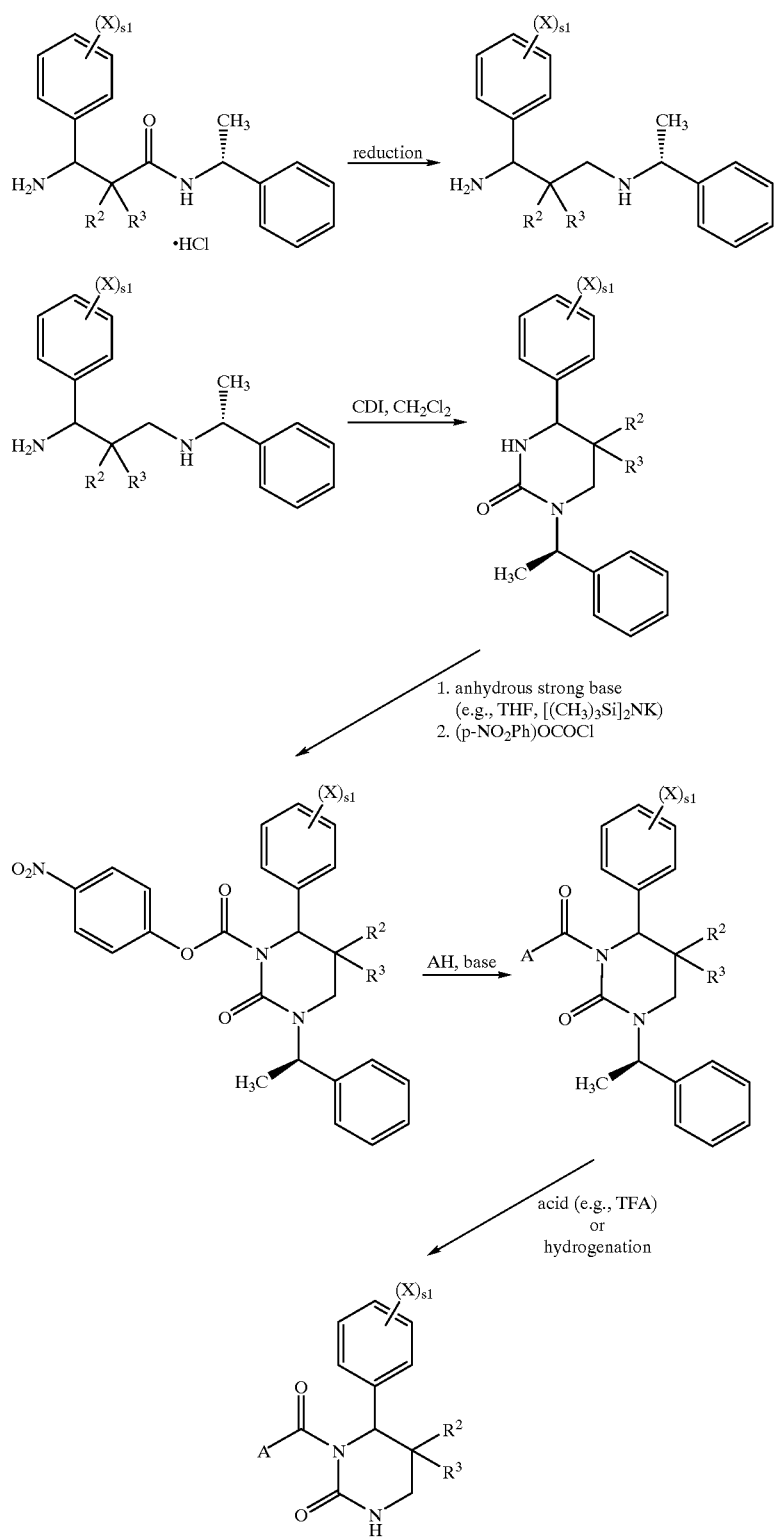

SCHEME 4
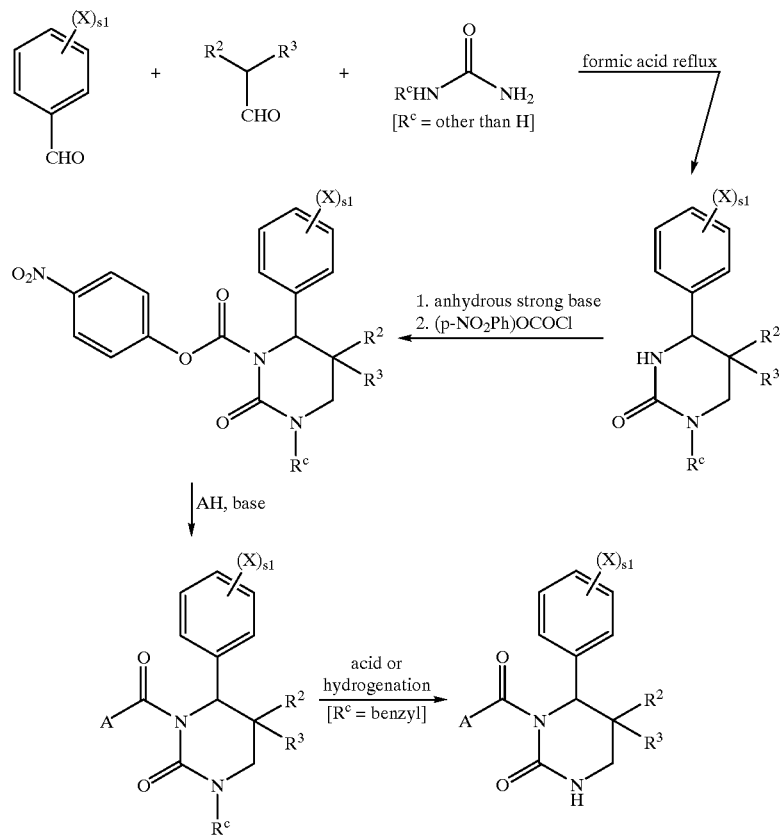
SCHEME 5
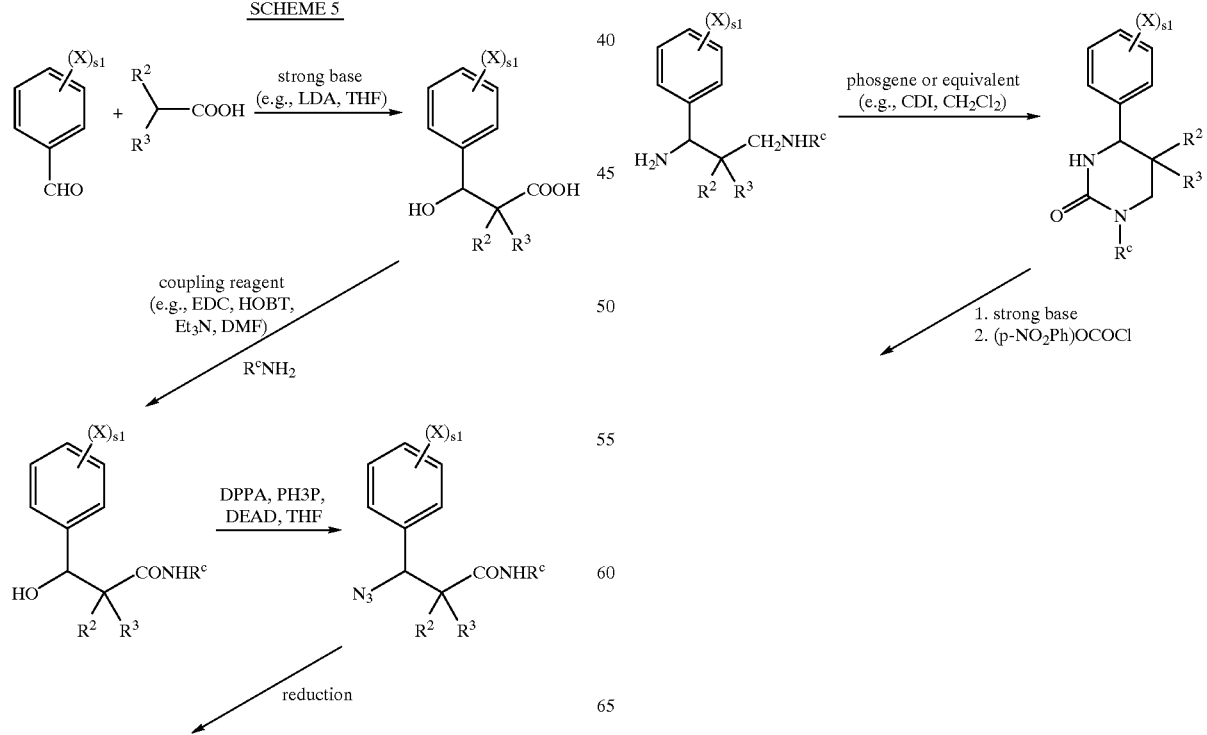

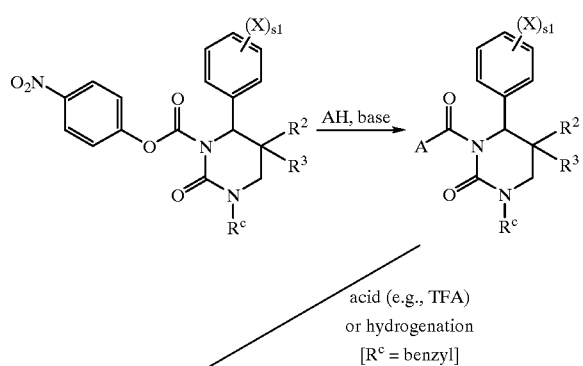
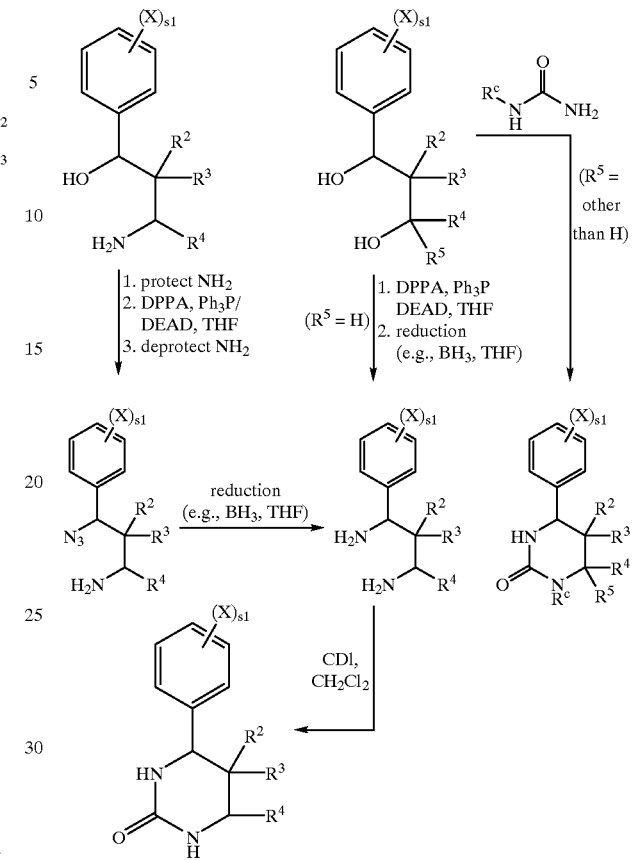
SCHEME 6
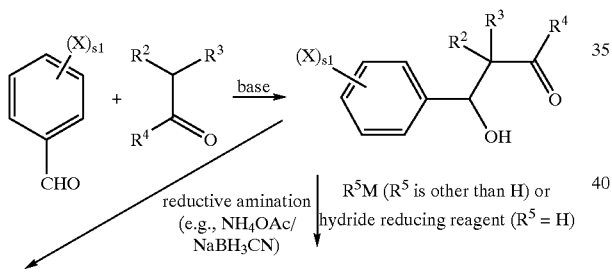
SCHEME 7
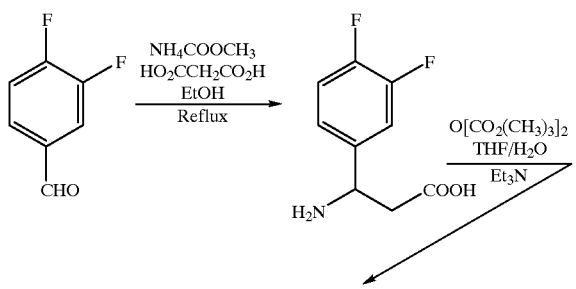

-continued
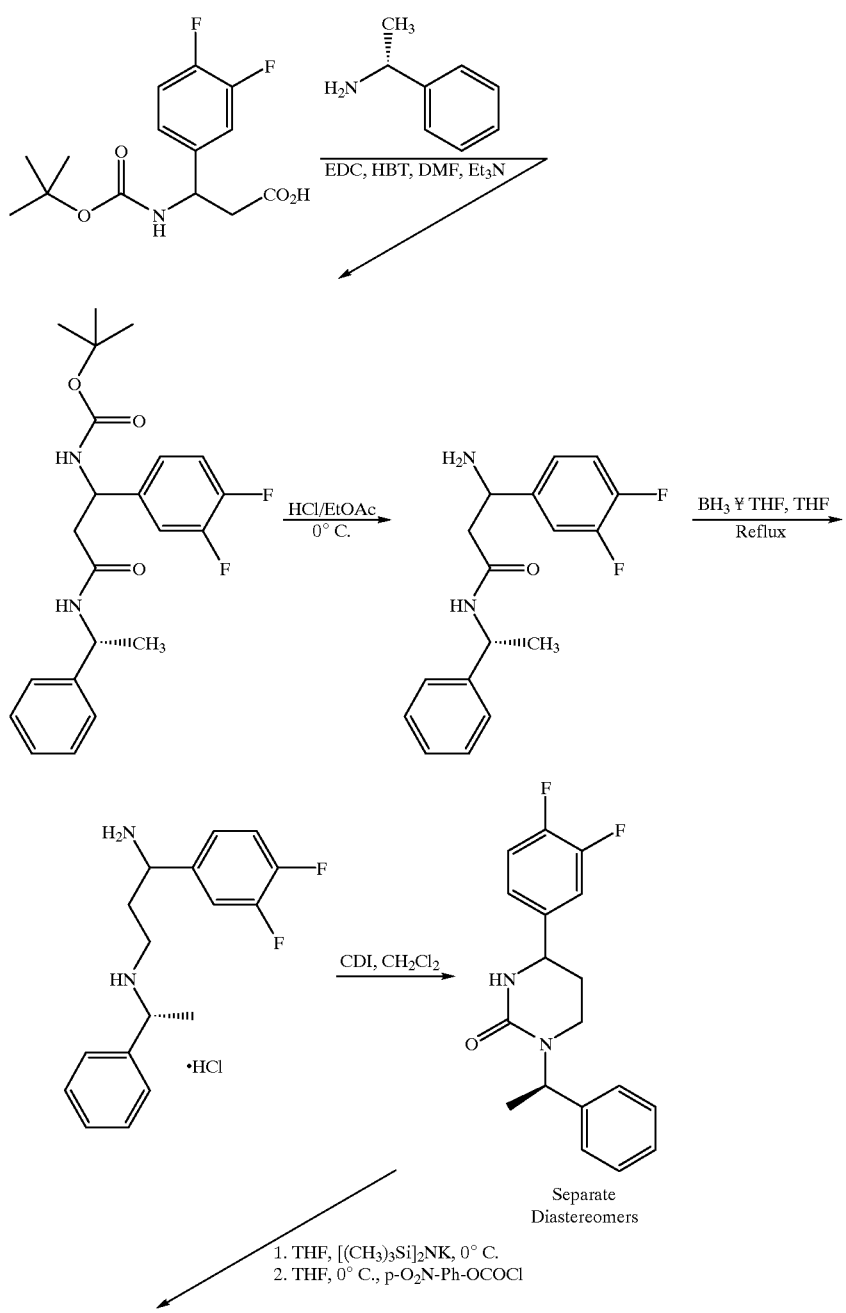
Separate Diastereomers
1. THF, [(CH₃)₃Si]₂NK, 0° C.
2. THF, 0° C., p-O₂N-Ph-OCOCl -continued
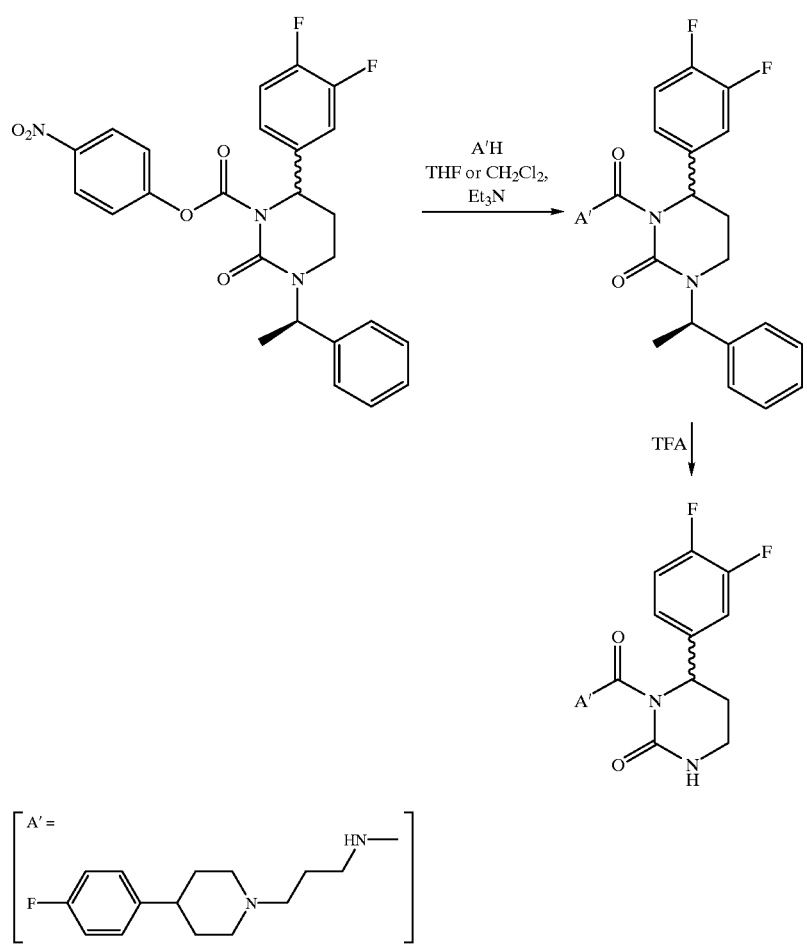
SCHEME 8
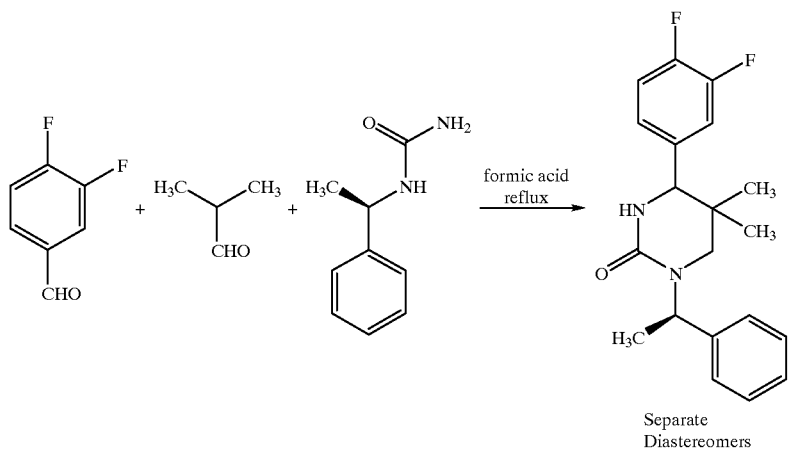
Separate Diastereomers

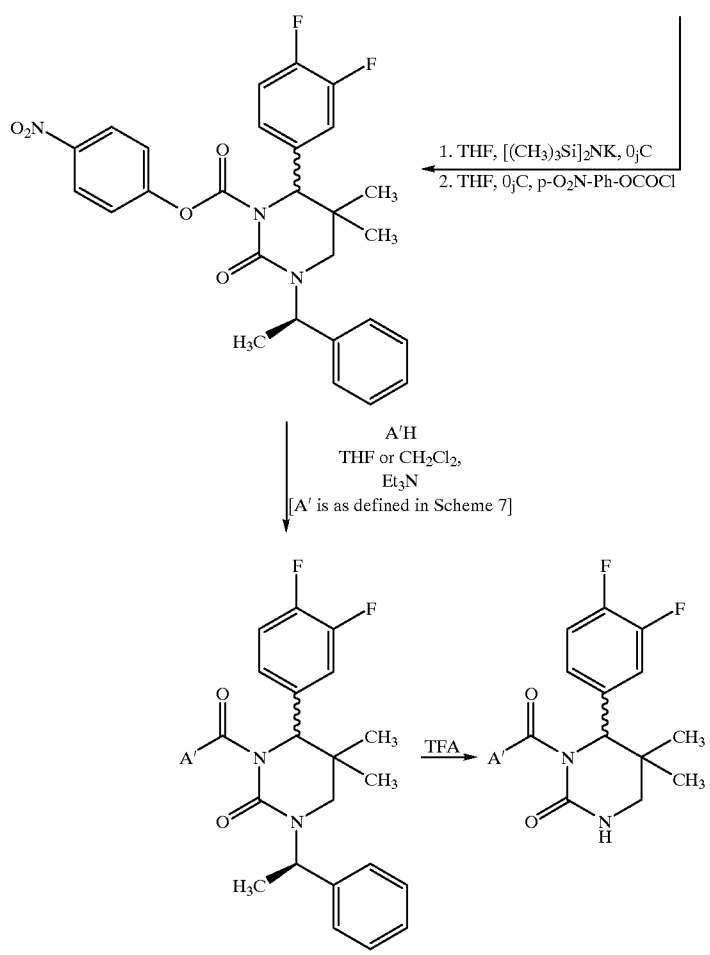
SCHEME 9
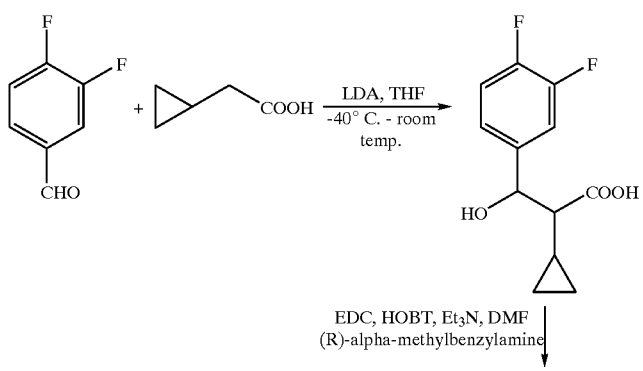

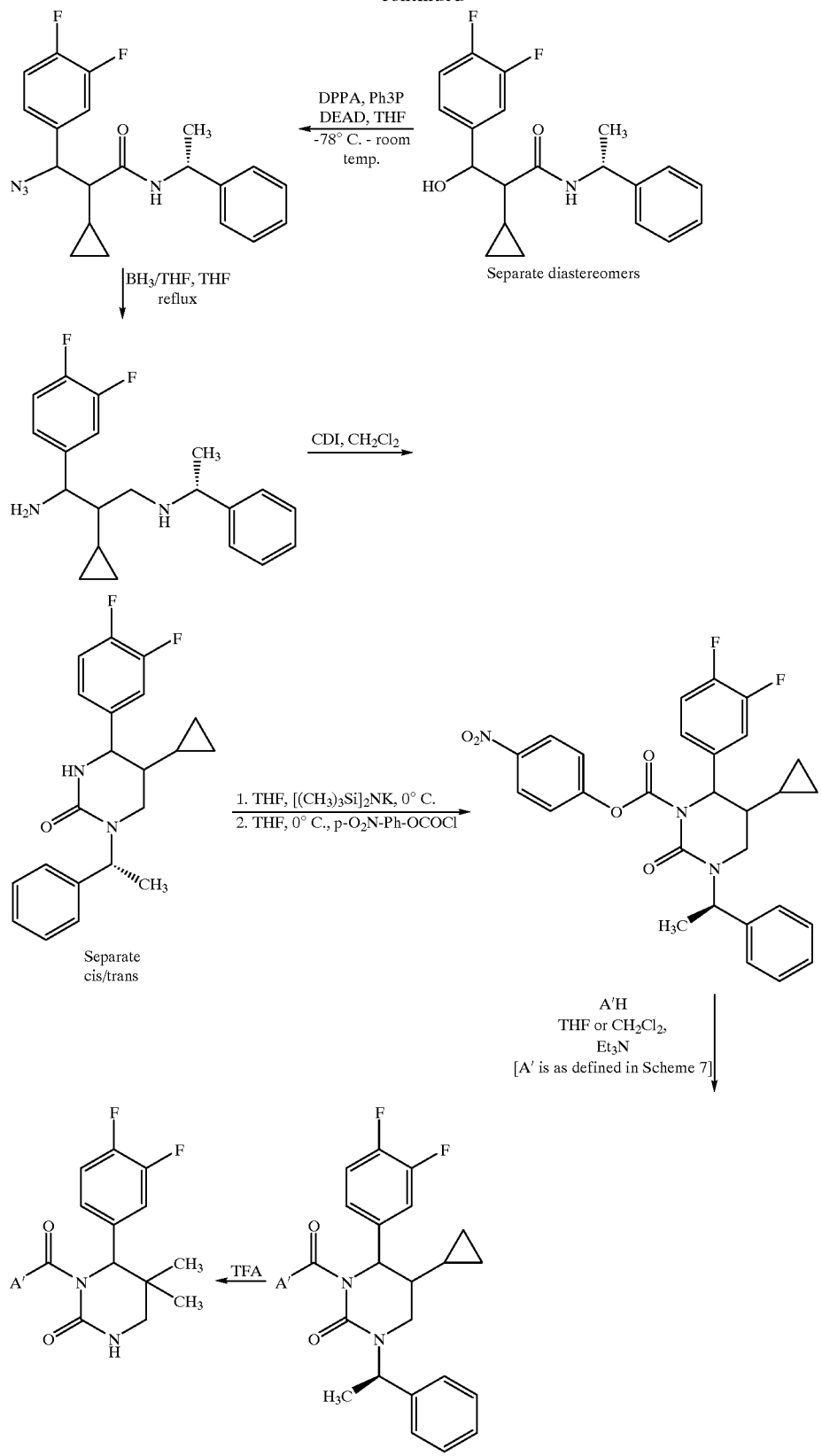

Many of the nucleophiles which are acylated with the activated lactam and cyclic urea intermediates to obtain compounds of the invention can be prepared using procedures the same or similar to those known in the art. Thus, for example, amines of structure A–H can be prepared using procedures, or variations thereof, described in U.S. Pat. No. 5,661,163 and WO 96/14846, wherein A is a1; WO 96/25934, wherein A is a2; WO 98/57632, wherein A is a3; WO 98/57638, wherein A is a4; WO 98/57642, wherein A is a5; WO 98/57639, wherein A is a6; WO 98/57640, wherein A is a7; and WO 98/57641, wherein A is a8.

Schemes 10–14 exemplify procedures for preparing the spirotnrcyclic nucleophiles of formula AH wherein A is formula (a9).

Spirofluorene-based nucleophiles can be prepared in accordance with Scheme 10, wherein fluorene G1 is treated with a strong base (e.g., LHMDA, LDA, or sodium or potassium hydride) and then with N-Boc-bis-(2-chloroethyl) amine to form the Boc-protected spirofluorene piperidine G2, which is treated with acid (e.g., TFA in CH$_2$Cl$_2$ or HCl in cold EtOAc) to obtain spiroflruoene piperidine G3. Other N-Boc-bis-(haloalkyl)amines can be used in place of N-Boc-bis(2-chloroethyl)amine to provide a wide range of other spirofluorene azacycloalkanes suitable for preparing compounds of the invention; i.e., Boc-protected amines of formula:

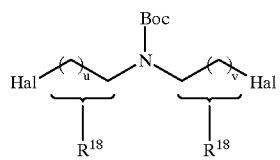

can be used to obtain spirofluorenes of formula:

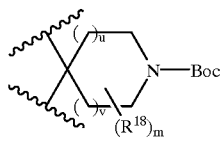

G3 can then be alkylated with a Boc-protected haloalkylamine to afford G4, which can then be deprotected to obtain G5 (=AH, wherein A is of formula (a9)).

Scheme 11 provides a procedure for preparing spirothioxanthene, 1-oxospirothioxanthene, and 1,1-dioxospiro-thioxanthen-based nucleophiles, wherein thioxanthone H1 is reduced to thioxanthene H2 which is spiroalkylated with N-methyl bis-(chloroethyl)amine to form H3 which is dealkylated using ethyl chloroformate to form H4. N-Methyl bis-(chloroethyl)amine can be replaced with amines of formula:

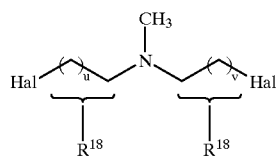

to obtain a wide range of spirothioxanthenes suitable for preparing compounds of the invention. H4 can be oxidized by treatment with 1 or with 2 equivalents of m-chloroperbenzoic acid to give the oxo or dioxo derivatives H5 or H6 respectively. The dioxo derivative H6 can alternatively be prepared from H4 by oxidizing H4 with, for example, H$_2$O$_2$-acetic acid, spiroalkylating the resulting dioxo compound with N-methyl bis-(chloroethyl)amine, and then dealkylating using ethyl chloroformate. Treatment of H4, H5, or H6 with base provides the free amine H7, which can be alkylated with a Boc-protected haloalkylamine to afford H8, which can be deprotected to obtain nucleophile H9.

Examples of spirothioxanthenepiperidines and their S-oxides and S,S-dioxides suitable for use as nucleophiles in preparing compounds of the invention are described in U.S. Pat. No. 4,001,418.

Spiroxanthene, spiroazafluorene, and spirodibenzocycloheptane nucleophiles can be prepared in accordance with Schemes 12–14 respectively. Spiroxanthene, spiroazafluorene, and spirodibenzo-cycloheptane compounds of the invention can be prepared via in accordance with the procedures set forth in Schemes 12–14 respectively. Reduction of a xanthone derivative, as illustrated in Scheme 12, provides the xanthene which may be spiroalkylated and elaborated to final products as described in preceding schemes and illustrated in Scheme 12. The xanthone may be obtained as described by Granoth and Pownall, *J. Org. Chem.* 1975, 40: 2088–2091. N-methyl-spiroxanthenepiperidine obtained as described by Galt et al., *J. Med. Chem.* 1989, 32: 2357–2362, may be converted to the 4-chloro- or 4,7-dichloro derivative by successive treatment with a chlorinating reagent, such as, for example, N-chlorosuccinimide.

Spiropiperidine derivatives of azafluorenes may be prepared from the corresponding fluorenones as illustrated in Scheme 13. Thus, reduction of the azafluorenones by, for example, the Wolff-Kishner procedure known in the art, provides the azafluorenes. Azafluorenes and azafluorenones are prepared by procedures known in the art such as, for example, those described by Kloc et al., *J. Prakt. Chem.* 1977, 319: 959–967; DuPriest et al., J. Org. Chem. 1986, 51: 2021–2023; Mayor and Wentrup, *J. Am. Chem. Soc.* 1975, 97: 7467–7480; Fuson and Miller, *J. Am. Chem. Soc.* 1957, 79: 3477–3480; Urbina, *Syn. Comm.* 9: 245–250; Wentrup et al., *J. Org. Chem.* 1978, 43: 2037–2041; Jutz et al., *Liebigs Ann. Chem.* 1975, 874–900; Braven et al., *J. Het. Chem.* 1995, 32: 1051–1055; and Hobson et al., *J. Chem. Soc.*, 1924, 2365–2370; and references cited therein.

Spirodibenzocycloheptanepiperidine derivatives may be prepared as shown in Scheme 14. Thus, 5-cyano-5H-dibenzocycloheptanes may be alkylated with, for example, N,N-dimethyl-2-chloroethane and strong base, such as lithium hexamethyldisilazide. The products may be reduced to aldehydes with, for example, DIBAH. Examples of the alkylation of 5-cyano-5H-dibenzocycloheptanes and reduction to aldehydes are described by Ting et al., *Bioorg. Med. Chem. Lett.* 1995, 5: 2749–2754. The aldehydes may be condensed with 2-TMS-1,3-dithiane in the presence of base. With refluxing HCl/methanol, the thiane products are converted to thioate esters which, upon reduction with, for example, LAH, afford hydroxyethyl derivatives. Conversion of the hydroxy group to halo by, for example, treatment with triphenylphosphine/carbon tetrachloride, and subsequent intramolecular alkylation to effect ring closure provides spirocyclic quaternary ammonium salts. Heating results in demethylation to tertiary amines, which may be again demethylated to the spiropiperidine.

Scheme 10
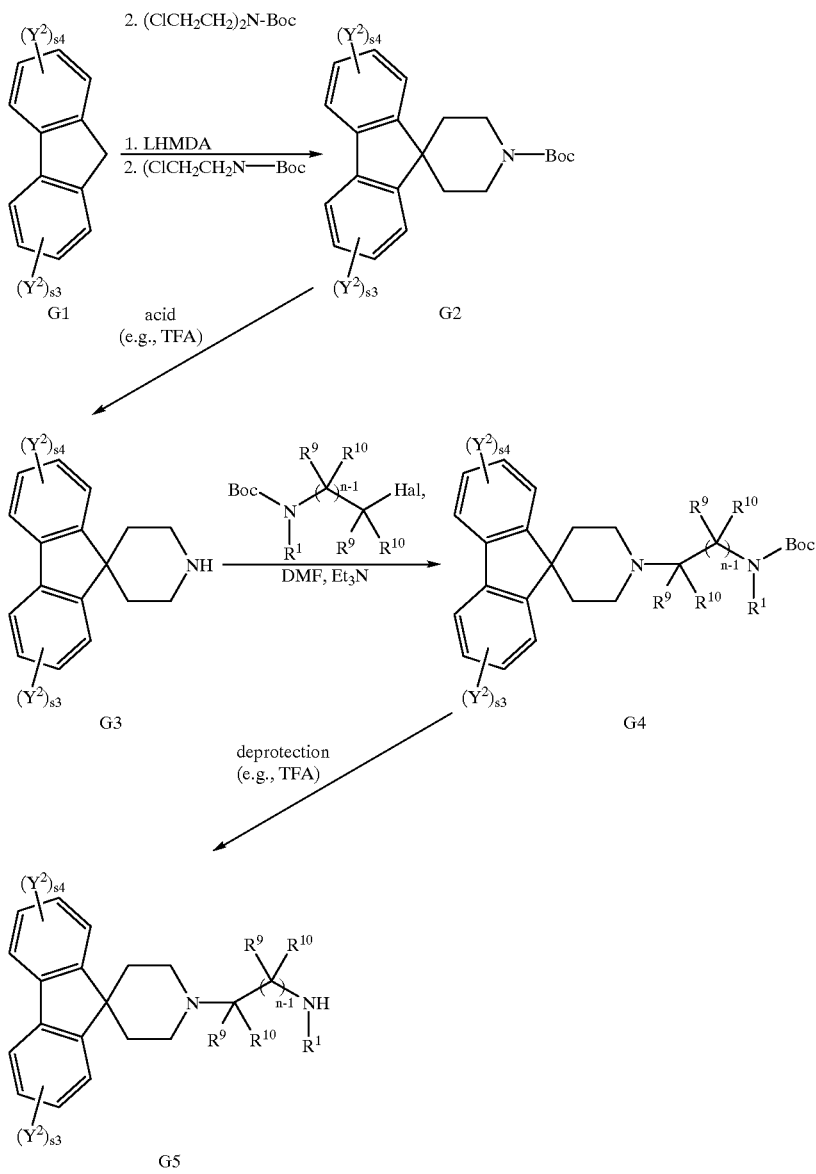
Scheme 11
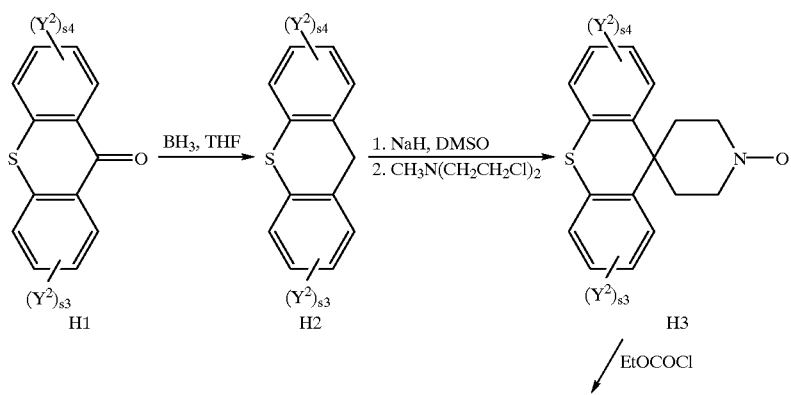

-continued
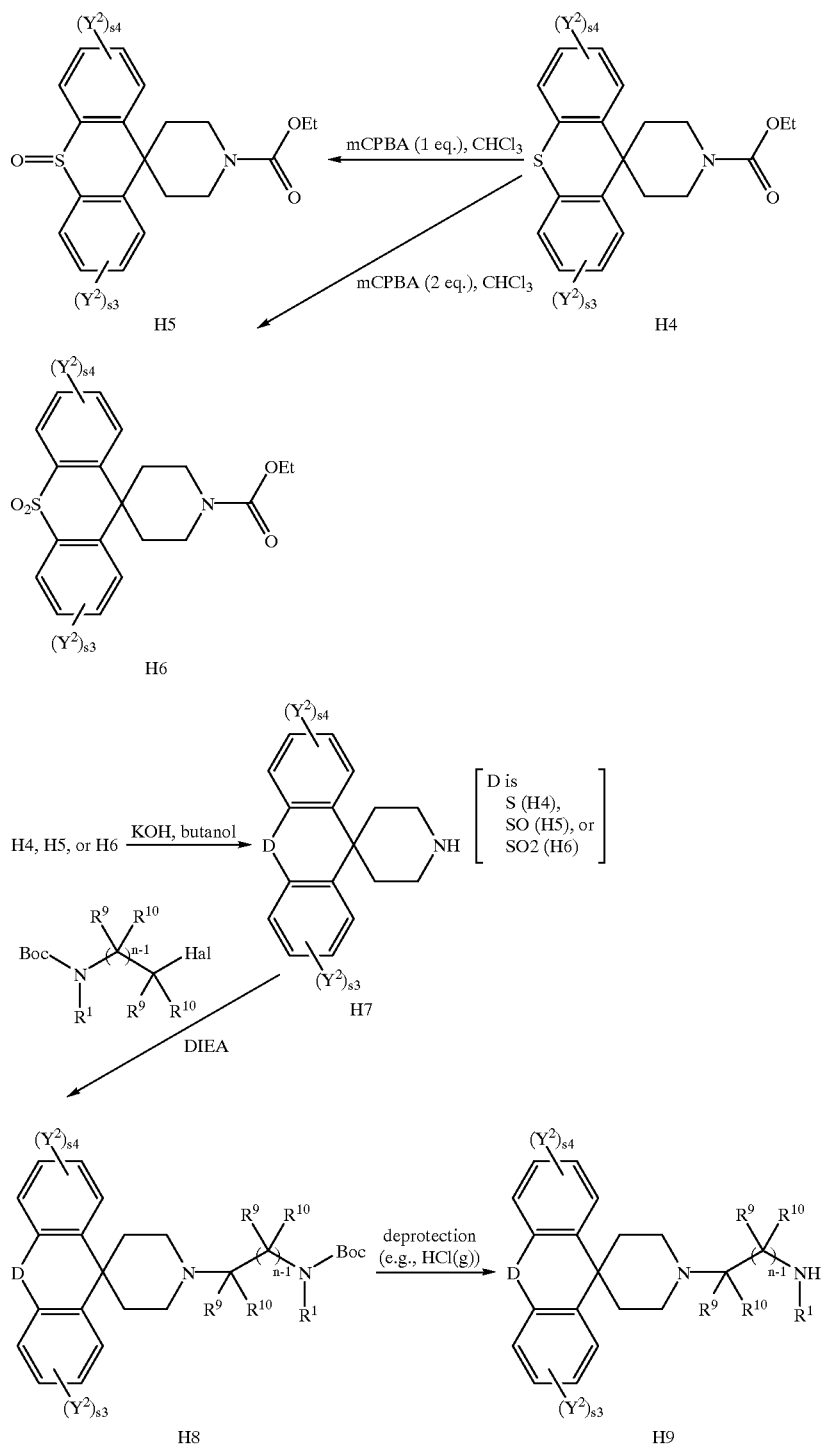

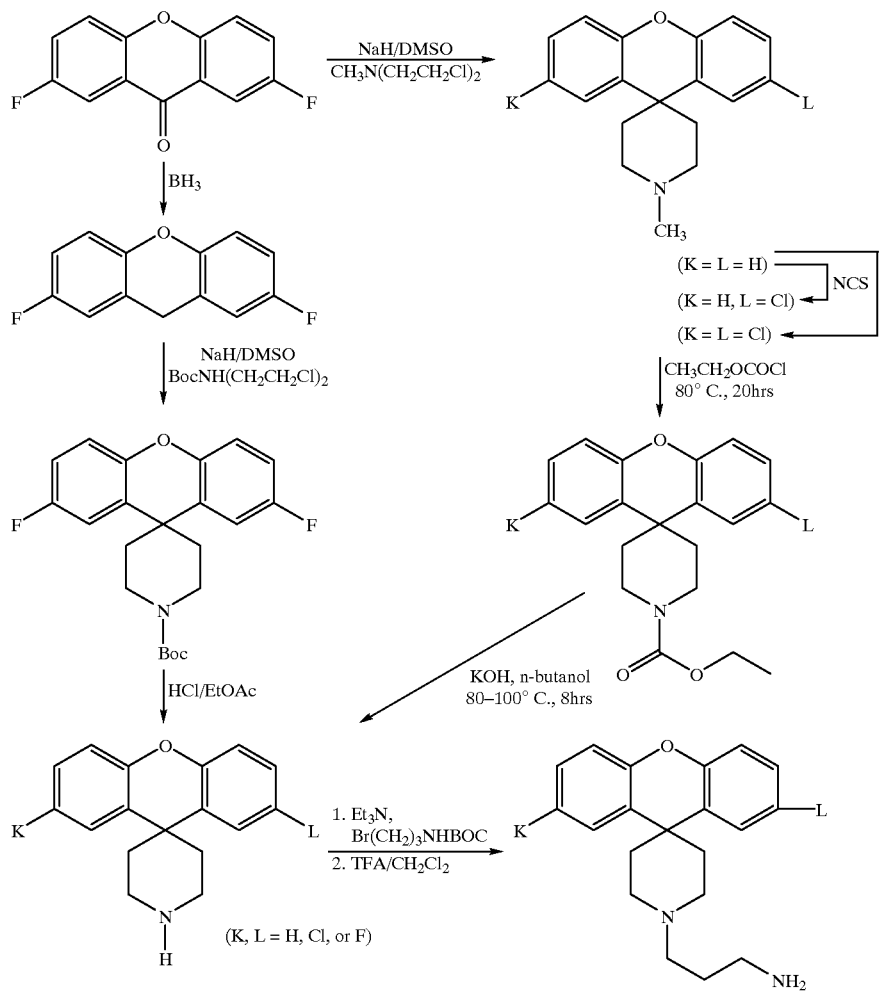
Scheme 12
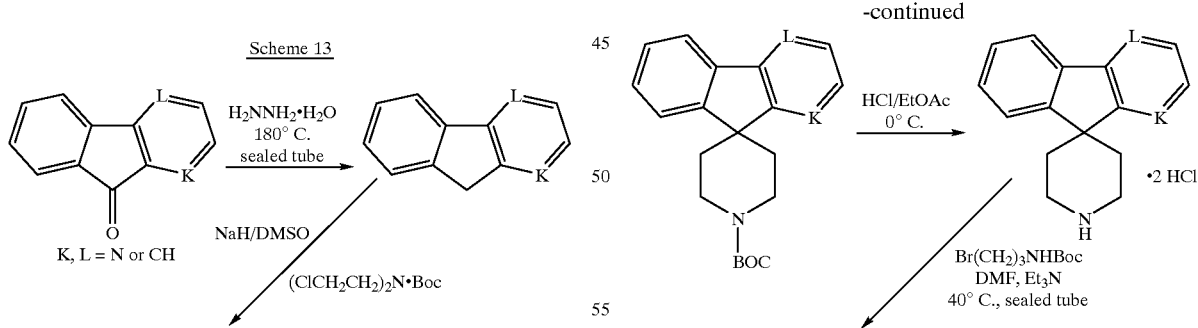
Scheme 13

-continued
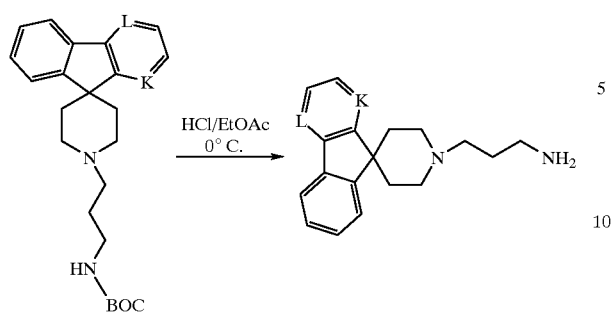
Scheme 14
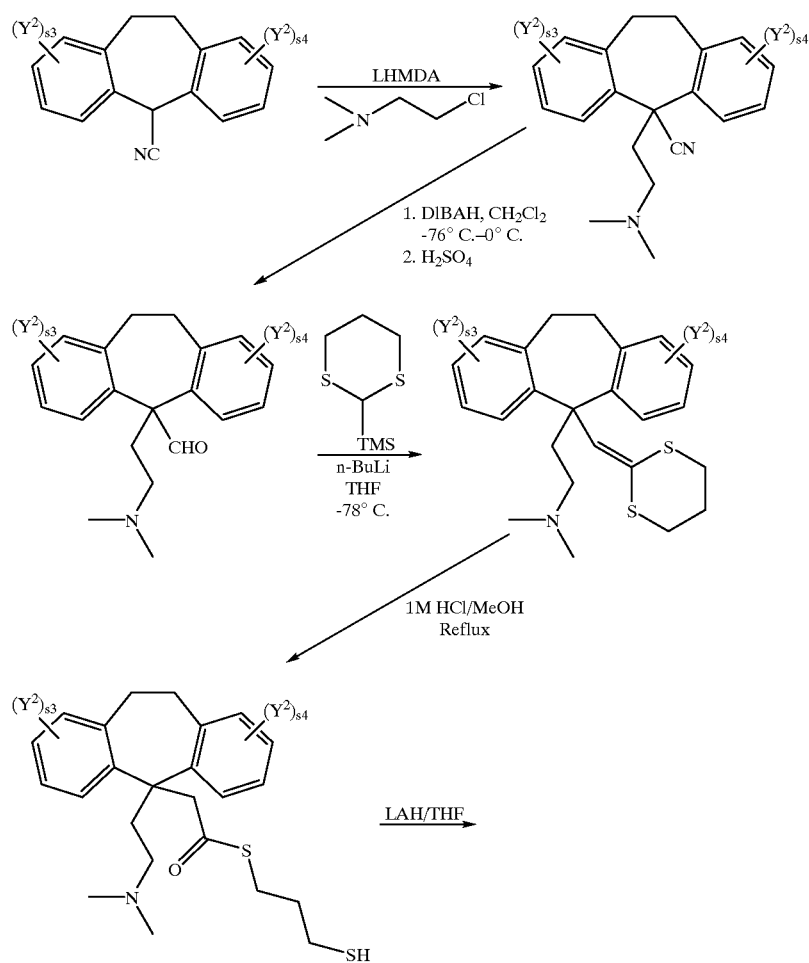

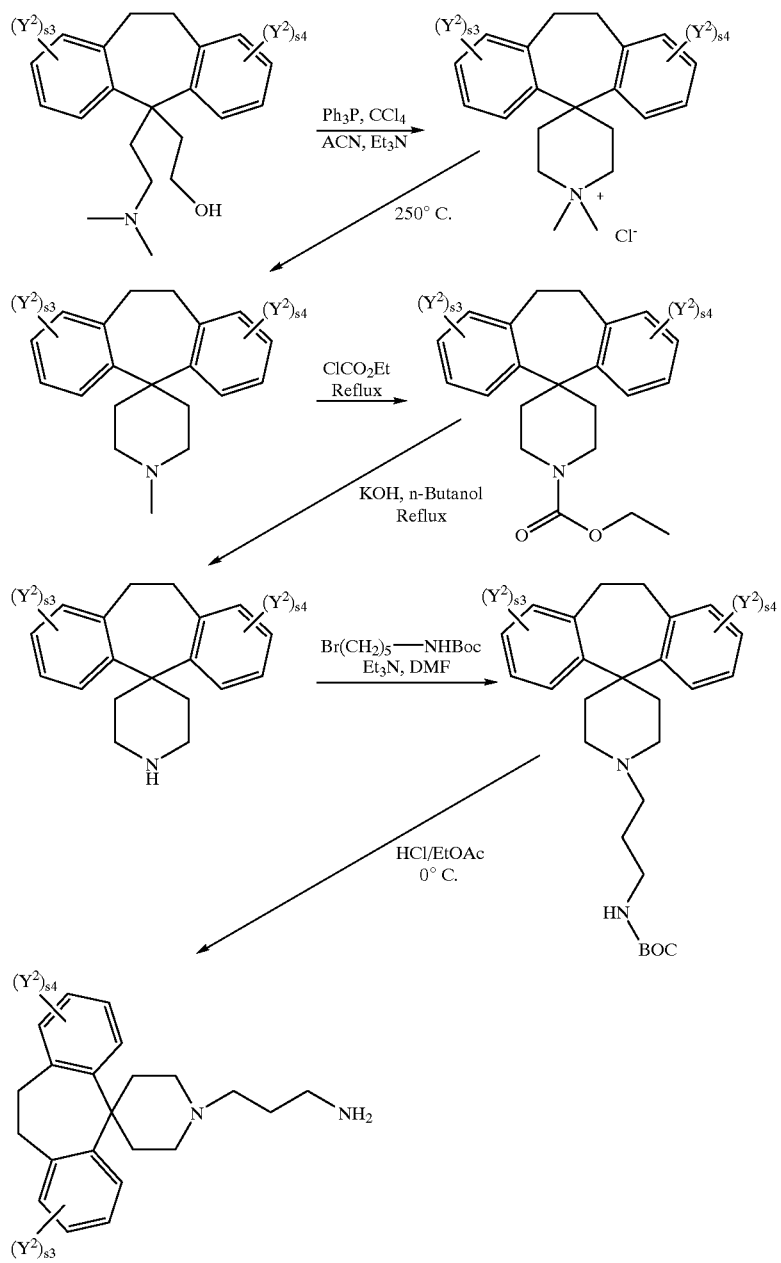

Many spirobicyclic nucleophiles of formula AH wherein A is formula (a10) can be prepared by the methods set forth in Schemes 15–19 below. Scheme 15 shows the preparation of spiroindanyl- and spiroindenyl-piperidines, wherein indene L1 is reacted with a strong base (e.g., LHMDA, LDA, or sodium or potassium hydride) and then with N-Boc-bis-(2-chloroethyl)amine to form the Boc-protected spiroindene piperidine L2, which is treated with acid (e.g., TFA in $CH_2Cl_2$ or HCl in cold EtOAc) to obtain spiro[1H-indeno-1,4'-piperidine] L3. Reduction of L2 ($H_2$ and palladium on carbon catalyst) followed by nitrogen deprotection (or, alternatively, reduction of L3) affords the spiro[indano-1,4'-piperidine] L4. For further description of this chemistry, see J. Med. Chem. 1992, 35: 2033–2039 and 3919–3927.

In the same manner as set forth in the discussion of Scheme 10 (the preparation of spirofluorene-based nucleophiles), other N-Boc-bis-(haloalkyl)amines can be used in place of N-Boc-bis(2-chloroethyl)amine to provide a wide range of spiroindene and spiroindane azacycloalkanes suitable for preparing compounds of the invention.

Scheme 16 provides a method for forming spiro[indano-1,4'-piperidin]-2-ones, wherein Boc-protected spiroindene piperidine L5 is treated with a peroxy acid to obtain epoxide intermediate L6, which forms the corresponding spiroindan-2-one L7 upon treatment with a Lewis acid. Nitrogen deprotection by treatment with an acid such as TFA provides L8. Alternatively, L7 can be alkylated on the indanone ring by reaction with alkyl halide and then nitrogen deprotected to afford L9.

Scheme 17 shows a method for forming spiro[isobenzofuran-1(3H),4'-piperidines] and spiro[isobenzofuran-1 (3H),4'-piperidin]-3-ones. N-phenylbenzamide L10 is lithiated with n-butyllithium and then reacted with N-Boc-piperidone to afford N-Boc-spiro[isobenzofuran-1(3H),4'-piperidin]-3-one L11, which can be treated with acid to form the deprotected analog L12. Alternatively, L11 can be reduced with borane and then deprotected to provide spiro[isobenzofuran-1(3H),4'-piperidine] L13. Further description of this chemistry can be found in *J. Org. Chem.* 1975, 40: 1427–1433.

Scheme 18 shows a method for forming spiro[3H-indole-3,4'-piperidin]-2(1H)-ones, in which 3H-indol-2(1H)-one L14 is treated with a strong base (e.g., LHMDA, LDA, or sodium or potassium hydride) and then with N-Boc-bis-(2-chloroethyl)amine to form the Boc-protected spiroindolyl piperidine L15, which is treated with acid (e.g., TFA in $CH_2Cl_2$ or HCl in cold EtOAc) to obtain L16. Further description of this chemistry can be found in *Org. Prep. Proced. Int.* 1995, 27: 691–694. [Note: This reference teaches that the first step of Scheme 18 works with a benzyl-protected reagent, but not with a Boc-protected reagent. Boc-protected reagents have been found herein to work satisfactorily with a suitable choice of strong base.] As noted above in discussing Schemes 10 and 15, other N-Boc-bis-(haloalkyl)amines can be used in place of N-Boc-bis(2-chloroethyl)amine in this scheme to provide a variety of analogs of L16.

Scheme 19 shows a method for forming spiro[4H-3,1-benzoxazine-4,4'-piperidine]-2(1H)-ones. Halo-substituted aniline L17 is treated with di-t-butylcarbonate to obtain L18, which is lithiated with t-butyllithium and reacted with a Boc'ed piperidone to obtain Boc-protected halobenzoxazinone L19, which can be deprotected by treatment with an acid to form L21, or can be N-alkylated on the benzoxazine ring by treatment with an alkyl halide and then deprotected to form L22. Alternatively, L19 can be dehalogneated by treatment with $H_2$/Pd to obtain L20, which can then be nitrogen-deprotected to afford L23, or can be N-alkylated and deprotected to form L24. Further description of this chemistry can be found in *J. Med. Chem.* 1983, 26: 657–661, *Chem. Pharm. Bull.* 1985, 33: 1129–1139, and U.S. Pat. No. 4,349,549.

Methods for preparing a variety of 1,2-dihydro-spiro[3H-indole-3,4'-piperidines] are disclosed in U.S. Pat. No. 5,536,716. For example, the preparations of 1,2-dihydro-1-methanesulfonylspiro[3H-indole-3,4'-piperidine] and spiro[3H-indole-3,4'-piperidine] are respectively described in Example 18, Step A and in Example 21, Step A of US 716.

SCHEME 15

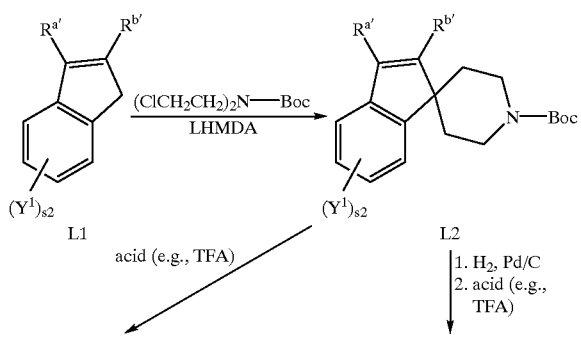

-continued

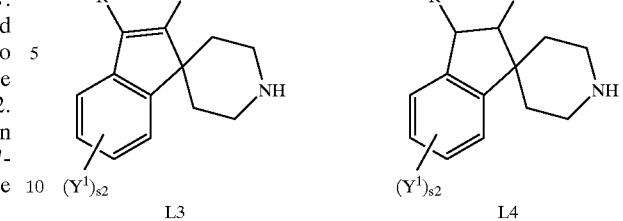

SCHEME 16

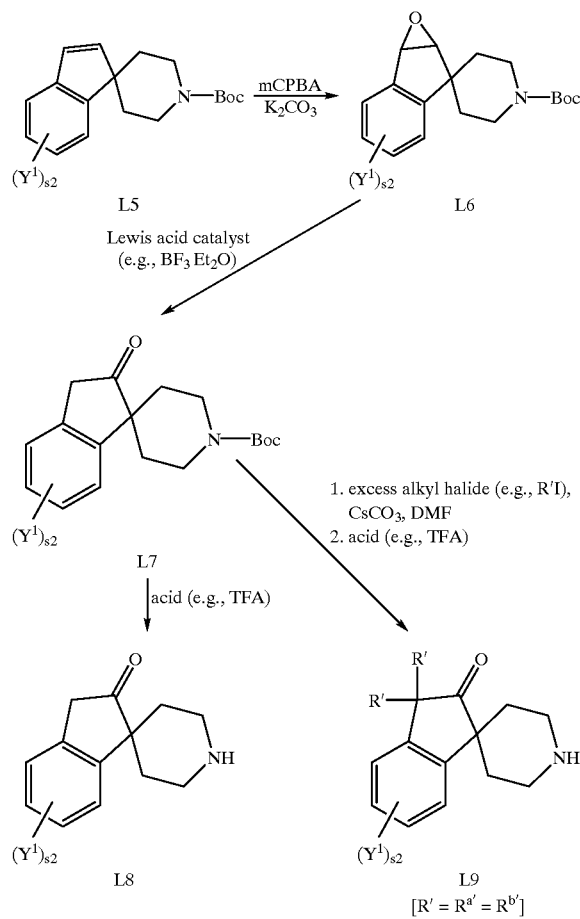

SCHEME 17

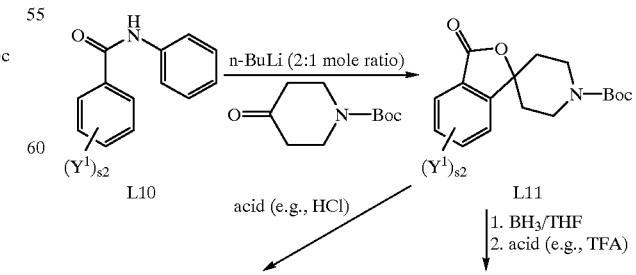

-continued
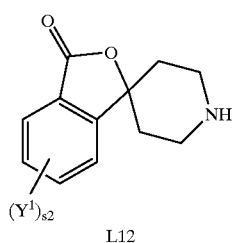
L12
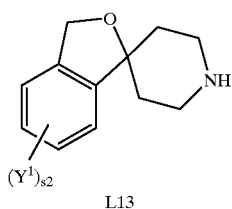
L13
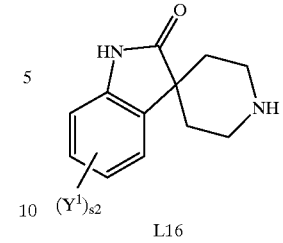
L16
SCHEME 18
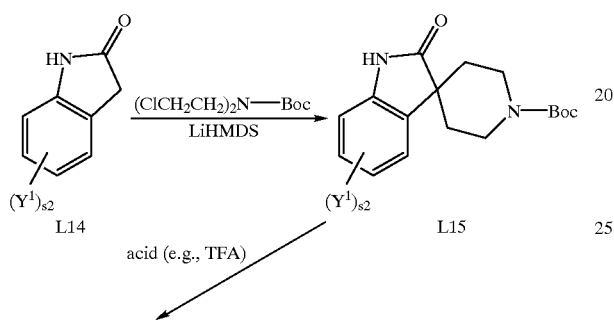
SCHEME 19
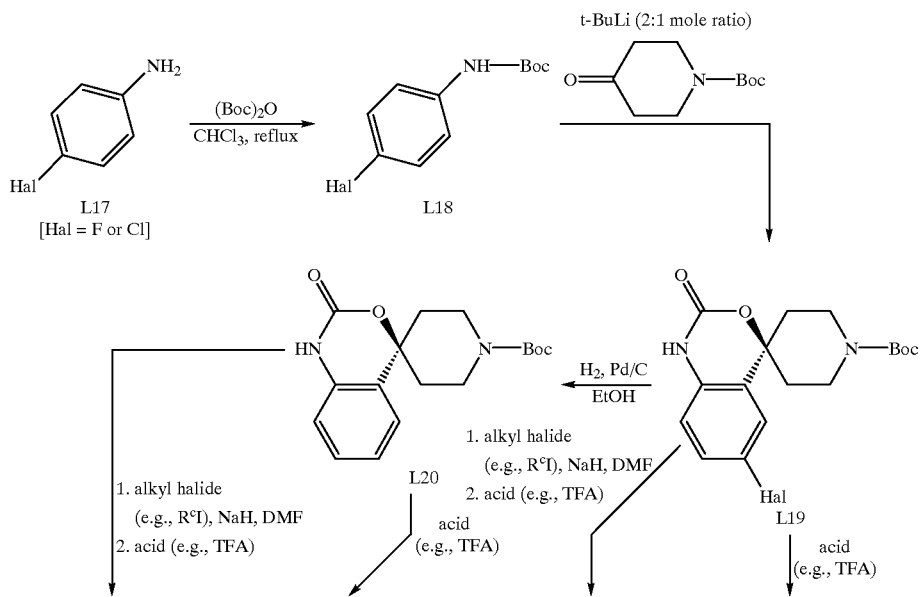

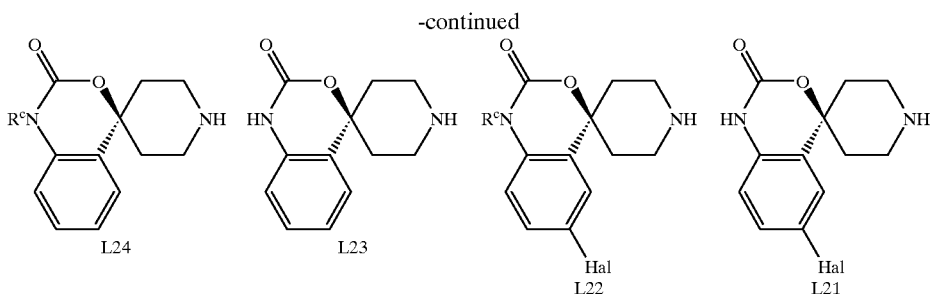

L24, L23, L22 (Hal), L21 (Hal)

The following s further describe and illustrate the invention and its practice and are not to be construed as limiting the scope or spirit of the invention. Stereoisomers were separated and isolated in many of the Examples, but their absolute configurations were not determined.

EXAMPLE 1

(6R)- and (6S)-1-[3-[4-(4-Fluorophenyl)piperidin-1-yl]propylamino-carbonyl]-6-(3,4-difluorophenyl)-3,3-dimethylpiperidin-2-one hydrochloride

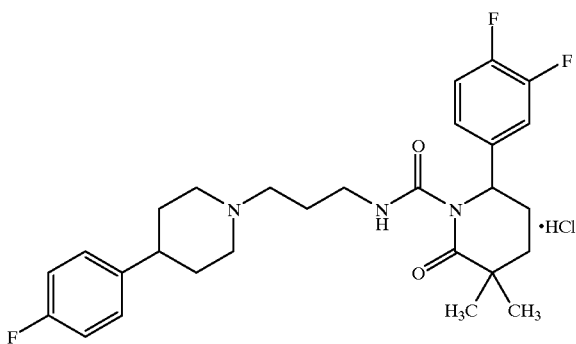

Step 1: Dimethyl-2,2-dimethylglutarate 2,2-Dimethylglutaric anhydride (15.04 g, 105.8 mmol) was dissolved in 300 mL of anhydrous methanol. Concentrated sulfuric acid (10 drops) was then added to the solution, and the resulting reaction mixture was stirred at 50° C. for 166 hours. The reaction mixture was concentrated in vacuo. The residue was dissolved in diethyl ether, filtered through a pad of silica gel, and the filtrate was evaporated to dryness to give the title compound as a clear colorless oil.

Step 2: Methyl-4-carboxy-2,2-dimethylbutyrate

Dimethyl-2,2-dimethylglutarate (18.26 g, 97.0 mmol) and potassium carbonate (27.14 g, 196.4 mmol) were dissolved in 280 mL of 3:2:2 methanol:tetrahydrofuran:water. The reaction mixture was stirred at ambient temperature for 73 hours, and then concentrated in vacuo. The resulting residue was taken up in water. The aqueous phase was extracted twice with ethyl acetate, and the organic phase was discarded. The aqueous phase was then acidified with a 1.0M aqueous solution of hydrochloric acid, and extracted three times with ethyl acetate. The ethyl acetate layer was washed once with brine, dried over sodium sulfate, filtered, and the filtrate was evaporated to dryness to give the title compound as an oil.

Step 3: 5-Methoxycarbonyl-4,4-dimethylbutyryl Chloride

Methyl-4-carboxy-2,2-dimethylbutyrate (12.02 g, 69.0 mmol) and thionyl chloride (11 mL, 151 mmol) were combined and stirred at ambient temperature for 19 hours. The mixture was then heated at 45° C. for 30 minutes. The reaction mixture was diluted with toluene and concentrated in vacuo twice to give the title compound as a liquid.

Step 4: 5-Methoxycarbonyl-4,4-dimethylbutyric acid-N-methyl-N-methoxyamide

5-Methoxycarbonyl-4,4-dimethylbutyryl chloride (12.28 g, 63.7 mmol) and N,O-dimethylhydroxylamine hydrochloride (9.65 g, 98.9 mmol) were combined in 200 mL of dichloromethane, and cooled to 0° C. Pyridine (16 mL, 198 mmol) was added to the mixture, and the reaction mixture was stirred at 0° C. for 2 hours. The mixture was then stirred at ambient temperature for 1.5 hours, and concentrated in vacuo. The resulting residue was partitioned between brine and a 1:1 mixture of dichloromethane : diethyl ether. The phases were separated, and the organic phase was dried over sodium sulfate, filtered, and evaporated to dryness to give the title compound as an oil.

Step 5: Methyl-5-(3,4-difluorophenyl)-2,2-dimethyl-5-oxopentanoate

Magnesium turnings (2.51 g, 103.2 mmol) were immersed in 15 mL of anhydrous tetrahydrofuran. A solution of 1-bromo-3,4-difluorobenzene (20 g, 103.6 mmol) in tetrahydrofuran (150 mL) was added dropwise to the magnesium suspension with stirring over a period of 30 minutes. The exothermic reaction was cooled in an ice bath when necessary. After complete addition, the reaction mixture was stirred for 1 hour. The resulting solution was then cannulated into a solution of 5-methoxycarbonyl-4,4-dimethylbutyric acid-N-methyl-N-methoxyamide (13.13 g, 60.4 mmol) in tetrahydrofuran (50 mL) which had previously been chilled to 0° C. The reaction mixture was stirred at 0° C. for 2.5 hours, and then poured into a 95:5 solution of ethanol:concentrated hydrochloric acid at 0° C. The resulting mixture was partitioned between water and a 1:1 mixture of dichloromethane:diethyl ether. The phases were separated. The organic phase was washed once with brine, dried over sodium sulfate, filtered, and the filtrate was evaporated to dryness. The resulting residue was purified by "flash" chromatography (90:10 hexanes:ethyl acetate). The product fractions were evaporated to dryness, and then reconcentrated once from dichloromethane to give the title compound as an oil.

Step 6: 6-(3,4-Difluorophenyl)-3,3-dimethylpiperidin-2-one

Ammonium acetate (36.62 g, 475.1 mmol) was dissolved in 200 mL of methanol. To this solution was added methyl-5-(3,4-difluorophenyl)-2,2-dimethyl-5-oxopentanoate (12.76 g, 47.2 mmol) and sodium cyanoborohydride (2.96 g, 47.1 mmol). This reaction mixture was stirred at ambient temperature for 24 hours. Another portion of sodium cyanoborohydride (1.50 g, 23.9 mmol) was added, and the mixture was stirred at ambient temperature for another 66 hours. The reaction mixture was concentrated in vacuo, and the residue was partitioned between dichloromethane and saturated sodium carbonate. A 1.0M solution of aqueous sodium hydroxide was added to the aqueous phase to achieve a pH of 10. The phases were then separated, and the aqueous phase was extracted three more times with dichloromethane. The combined organic phases were then washed once with brine, dried over sodium sulfate, filtered, and the filtrate was evaporated to dryness. This residue was purified by "flash" chromatography (98:2 dichloromethane:methanol). The product fractions were evaporated to dryness to give the title compound as a solid.

Step 7: 6-(3,4-Difluorophenyl)-3,3-dimethyl-1-(4-nitrophenyloxycarbonyl)piperidin-2-one Potassium hydride/mineral oil suspension (35%, 1.05 g, 9.16 mmol) was suspended in 10 mL of anhydrous tetrahydrofuran, and cooled to 0° C. A solution of 6-(3,4-difluorophenyl)-3,3-dimethylpiperidin-2-one (2.22 g, 9.28 mmol) in tetrahydrofuran (150 mL) was added to the hydride suspension via syringe. The resulting mixture was warmed to ambient temperature and stirred for 1 hour. The solution was then transferred via syringe to a solution of 4-nitrophenylchloroformate (1.86 g, 9.23 mmol) in tetrahydrofuran (75 mL) which had been chilled previously to 0° C. The mixture was stirred at 0° C. for 1 hour, and then warmed to ambient temperature where it was stirred for an additional 2 hours. The reaction mixture was evaporated to dryness, dissolved in dichloromethane, and filtered. The filtrate containing the product was purified by "flash" chromatography (97:3 dichloromethane:diethyl ether). The product fractions were evaporated to dryness to give the title compound as an oil.

Step 8: (6R)- and (6S)-1-[3-[4-(4-Fluorophenyl)piperidin-1-yl]propylaminocarbonyl]-6-(3,4-difluorophenyl)-3,3-dimethylpiperidin-2-one Hydrochlorides 6-(3,4-difluorophenyl)-3,3-dimethyl-1-(4-nitrophenyloxycarbonyl)piperidin-2-one (1.28 g, 3.17 mmol), 3-[4-(4-fluorophenyl)-piperidin-1-yl]propylamine dihydrochloride (1.12 g, 3.62 mmol) and triethylamine (1.77mL, 12.7 mmol) were dissolved in 30 mL of dichloromethane. The reaction mixture was stirred at ambient temperature for 18 hours, and then evaporated to dryness. The residue was dissolved in dichloromethane and washed eleven times with saturated sodium bicarbonate. The organic phase was then washed twice with a 1.0M aqueous solution of sodium hydroxide and once with brine. The organic phase was dried over sodium sulfate, filtered, and the filtrate was evaporated to dryness. The resulting residue was purified by "flash" chromatography (97:3:0.3 dichloromethane:methanol:ammonium hydroxide). The product fractions were evaporated to dryness to give the title compound as an oil. The racemic mixture was then purified by preparative HPLC (Chiralpak AD, 65:35 hexane:2-propanol which contained 0.1% DEA). The separate product fractions were evaporated to dryness to give the individual enantiomers of the title compound. The enantiomers were each treated with HCl-saturated ethyl acetate, evaporated to dryness, and reconcentrated three times from diethyl ether to give the title compounds as white solids.

Enantiomer A:

m.p.=199–200° C.; NMR: consistent with structure; HPLC: 93.1% pure; FAB MS: M+H @ m/e=502.4; Analysis calc'd for C28H34F3N3O2.HCl.0.15 Et2O. 0.50 H2O: C, 61.54; H, 6.77; N, 7.53. Found: C, 61.53; H, 6.47; N, 7.53.

Enantiomer B:

m.p.=199–200° C. NMR: consistent with structure; HPLC: 100% pure; FAB MS: M+H @ m/e=502.4; Analysis calc'd for C28H34F3N3O2.HCl: C, 62.50; H, 6.56; N, 7.81. Found: C, 62.50; H, 6.46; N, 7.66.

EXAMPLE 2

(6R)- and (6S)-1-[3-[4-(4-Fluorophenyl)piperidin-1-yl]propylamino-carbonyl]-6-(3,4-difluorophenyl)-4,4-dimethylpiperidin-2-one hydrochloride

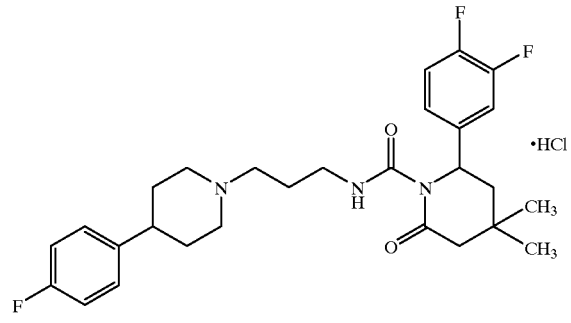

Step 1: 3,3-Dimethylglutaric Anhydride 3,3-Dimethylglutaric acid (18.70 g, 116.8 mmol) was dissolved in acetyl chloride (25 mL, 352 mmol), and refluxed for 2 hours. The reaction mixture was evaporated to dryness, and the residue was dissolved in diethyl ether. The ether solution was concentrated on a steam bath, and then cooled to 0° C. for 1 hour. The precipitate was filtered to give the title compound.

Step 2:

3,3-Dimethylglutaric anhydride (11.08 g, 77.9 mmol) was dissolved in methanol (20 mL), and refluxed for 5.5 hours. The reaction mixture was then evaporated to dryness to give the title compound as a liquid.

Steps 3–8: (6R)- and (6S)-1-[3-[4-(4-Fluorophenyl)piperidin-1-yl]propylaminocarbonyl]-6-(3,4-difluorophenyl)-4,4-dimethylpiperidin-2-one Hydrochlorides The procedures of Example 1, steps 3–8 were carried out using methyl-4-carboxy-3,3-dimethylbutyrate in place of methyl-4-carboxy-2,2-dimethylbutyrate in step 3. The racemic final product was purified by preparative chiralpak AD HPLC (50:50 hexane:2-propanol which contained 0.1% DEA). The separate product fractions were evaporated to dryness to give the individual enantiomers of the title compound. The enantiomers were each treated with HCl-saturated ethyl acetate, evaporated to dryness, and reconcentrated three times from diethyl ether to give the title compounds as solids.

Enantiomer A:

m.p.=61–65° C.; NMR: consistent with structure; HPLC: 99.5% pure; FAB MS: M+H @ m/e =502.2; Analysis calc'd for C28H34F3N3O2.HCl.0.15 Et2O. 1.35 H2O: C, 59.89; H, 6.89; N, 7.33. Found: C, 59.90; H, 6.55; N, 7.33.

Enantiomer B:

m.p.=57–60° C.; NMR: consistent with structure; HPLC: 99.7% pure; FAB MS: M+H @ m/e=502.28; Analysis calc'd for C28H34F3N3O2.HCl.0.15 Et2O. 1.80 H2O: C, 59.06; H, 6.95; N, 7.23. Found: C, 59.06; H, 6.72; N, 7.14.

EXAMPLE 3

(4R,6R)-, (4S,6R)-, (4R,6S)-, and (4S,6S)-1-[3-[4-(4-Fluorophenyl) piperidin-1-yl] propylaminocarbonyl]-6-(3,4-difluorophenyl)-4-methylpiperidin-2-one Hydrochloride

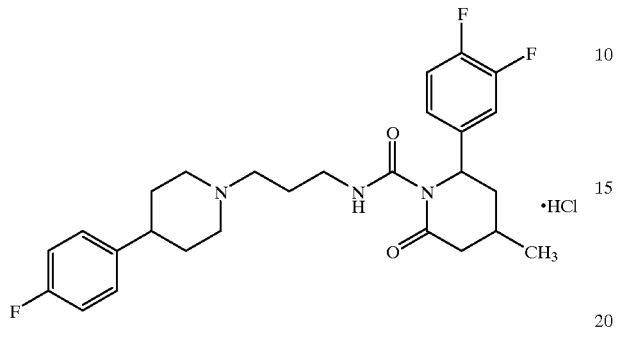

Step 1: Methyl-4-carboxy-3-methylbutyrate

The procedure of Example 2, step 2 was carried out using 3-methylglutaric anhydride in place of 3,3-dimethylglutaric anhydride.

Steps 2–7: (4R,6R)-, (4S,6R)-, (4R,6S)-, and (4S,6S)-1-[3-[4-Fluorophenyl)piperidin-1-yl]propylaminocarbonyl]-6-(3,4-difluorophenyl)-4-methylpiperidin-2-one Hydrochlorides The procedures of Example 1, steps 3–8 were carried out using methyl-4-carboxy-3-methylbutyrate in place of methyl-4-carboxy-2,2-dimethylbutyrate in step 3. The racemic diastereomers were separated by preparative HPLC ($H_2O$:MeCN gradient containing 0.1% TFA). The product fractions of each racemic diastereomer were evaporated to dryness. The first racemic diastereomer was purified by preparative chiralpak AD HPLC (30:70 hexane:2-propanol which contained 0.1% DEA). The second racemic diastereomer was purified by preparative chiralpak AD HPLC (20:80 hexane:2-propanol which contained 0.1% DEA). The product fractions were evaporated to dryness. Each isomer residue was treated with HCl-saturated ethyl acetate, evaporated to dryness, and reconcentrated three times from diethyl ether to give the title compounds as solids.

Isomer A:

m.p.=57–60° C.; NMR: consistent with structure; HPLC: 99.5% pure; FAB MS: M+H @ m/e=488.3; Analysis calc'd for C27H32F3N3O2.HCl.0.05 H2O.0.50 HCl: C, 59.70; H, 6.24; N, 7.74. Found: C, 59.72; H, 6.09; N, 7.34.

Isomer B:

m.p.=57–60° C.; NMR: consistent with structure; HPLC: 85.7% pure; FAB MS: M+H @ me=488.2; Analysis calc'd for C27H32F3N3O2.HCl.0.35 Et2O.0.70 HCl: C, 59.27; H, 6.52; N, 7.30. Found: C, 59.28; H, 6.31; N, 6.97.

Isomer C:

m.p.=57–60° C.; NMR: consistent with structure; HPLC: 88.1% pure; FAB MS: M+H @ m/e=488.2; Analysis calc'd for C27H32F3N3O2. HCl.0.20 Et2O.0.55 HCl: C, 59.74; H, 6.41; N, 7.52. Found: C, 59.68; H, 6.03; N, 7.15.

Isomer D:

m.p.=57–60° C.; NMR: consistent with structure; HPLC: 92.4% pure; FAB MS: M+H @ m/e=488.2; Analysis calc'd for C27H32F3N3O2.HCl.0.15 Et2O.0.95 H2O: C, 60.02; H, 6.64; N, 7.61. Found: C, 60.03; H, 6.25; N, 7.40.

EXAMPLE 4

(6RS)-, 6(R)-, and 6(S)-1-[3-[4-(4-Fluorophenyl) piperidin-1-yl]-propylaminocarbonyl]-6-(3,4-difluorophenyl)piperidin-2-one Hydrochloride

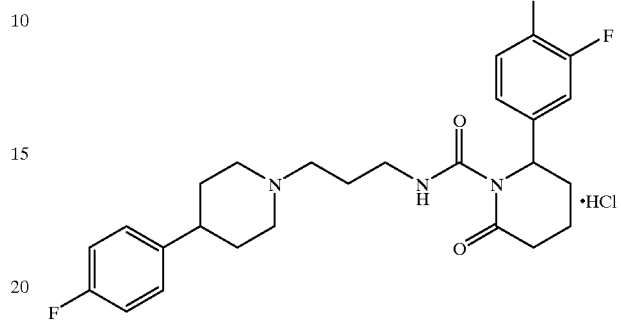

The procedures of Example 1, steps 4–8 were carried out using 5-methoxycarbonylbutyryl chloride in place of 5-methoxycarbonyl-4,4-dimethylbutyryl chloride in step 4. The racemic product (L-834,534) was purified by preparative chiralcel OJ HPLC (70:30 hexane:ethanol which contained 0.1% DEA). The product fractions were evaporated to dryness. Each isomer residue was treated with HCl-saturated ethyl acetate, evaporated to dryness, and reconcentrated three times from diethyl ether to give the title compound as a solid.

Isomer A:

m.p.=69–75° C.; NMR: consistent with structure; HPLC: 99.4% pure; FAB MS: M+H @ m/e=474.1; Analysis calc'd for C26H30F3N3O2.HCl.0.25 Et2O.0.50 H2O: C, 60.32; H, 6.47; N, 7.82. Found: C, 60.33; H, 6.23; N, 7.68.

Isomer B:

m.p.=69–72° C.; NMR: consistent with structure; HPLC: 100% pure; FAB MS: M+H @ m/e=474.2; Analysis calc'd for C26H30F3N3O2.HCl.0.20 Et2O. 0.50 H2O: C, 60.29; H, 6.42; N, 7.87. Found: C, 60.29; H, 6.04; N, 7.83.

Isomer C:

m.p.=69–75° C.; NMR: consistent with structure; HPLC: 99.7% pure; FAB MS: M+H @ m/e=474.2; Analysis calc'd for C26H30F3N3O2.HCl.0.15 Et2O.0.45 H2O: C, 60.36; H, 6.36; N, 7.94. Found: C, 60.35; H, 6.30; N, 7.87.

EXAMPLE 5

(6RS)-, 6(R)- and 6(S)-1-[3-[4-(2-Cyanophenyl)-4-cyanopiperidin-1-yl]-propylaminocarbonyl]-6-(3,4-difluorophenyl)piperidin-2-one Hydrochloride

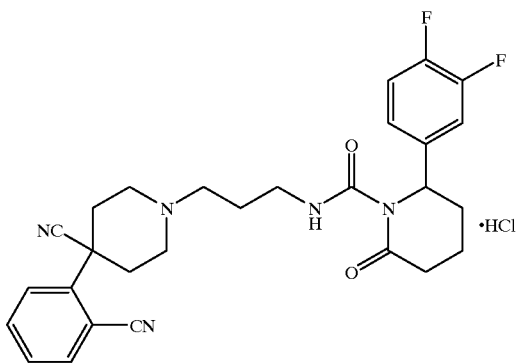

The procedures of Example 4 were carried out using 3-[4-(2-cyanophenyl)-4-cyanopiperidin-1-yl]propylamine in place of 3-[4-(4-fluorophenyl)piperidin-1-yl]propylamine dihydrochloride. The racernic product (L-834,834) was purified by preparative chiralpak AD HPLC (55:45 hexane:2-propanol which contained 0.1% DEA). The product fractions were evaporated to dryness. Each isomer residue was treated with HCl-saturated ethyl acetate, evaporated to dryness, and reconcentrated three times from diethyl ether to give the title compound as a solid.

Isomer A:
m.p.=182–184° C.; NMR: consistent with structure; HPLC: 100% pure; FAB MS: M+H @ m/e=506; Analysis calc'd for $C_{28}H29F2N5O2.HCl.0.45$ Et2O.0.40 HCl: C, 60.66; H, 5.96; N, 11.87. Found: C, 60.74; H, 5.57; N, 11.80.

Isomer B:
m.p.=91–100° C.; NMR: consistent with structure; HPLC: 97.5% pure; FAB MS: M+H @ m/e=506.4; Analysis calc'd for C28H29F2N5O2.HCl.0.15 Et2O.1.25 H2O: C, 59.67; H, 5.95; N, 12.17. Found: C, 59.65; H, 5.74; N, 12.16.

Isomer C:
m.p.=130–135° C.; NMR: consistent with structure; HPLC: 100% pure; FAB MS: M+H @ m/e=506; Analysis calc'd for C28H29F2N5O2.HCl.0.55 Et2O.0.45 H2O: C, 61.38; H, 6.21; N, 11.85. Found: C, 61.41; H, 5.90; N, 11.86.

EXAMPLE 6

6(R)- and 6(S)-1-[3-[4-(4-Fluorophenyl)-4-cyanopiperidin-1-yl]propylaminocarbonyl]-6-(3,4-difluorophenyl)piperidin-2-one Hydrochloride

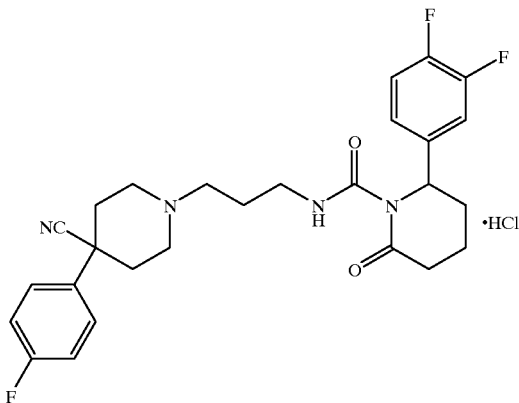

The procedures of Example 4 were carried out using 3-[4-(4-fluorophenyl)-4-cyanopiperidin-1-yl]propylamine in place of 3-[4-(4-fluorophenyl)piperidin-1-yl]propylamine dihydrochloride. The racemic product was purified by preparative chiralpak AD HPLC (35:65 hexane:2-propanol which contained 0.1% DEA). The product fractions were evaporated to dryness. Each isomer residue was treated with HCl-saturated ethyl acetate, evaporated to dryness, and reconcentrated three times from diethyl ether to give the title compounds as solids.

Enatiomer A:
m.p.=190–193° C.; NMR: consistent with structure; HPLC: 98.4% pure; FAB MS: M+H @ m/e=499.2; Analysis calc'd for C27H29F3N4O2.HCl.0.05 Et2O.0.30 H2O: C, 60.04; H, 5.76; N, 10.30. Found: C, 60.05; H, 5.86; N, 10.57.

Enantiomer B:
m.p.=190–193° C.; NMR: consistent with structure; HPLC: 100% pure; FAB MS: M+H @ m/e=499.2; Analysis calc'd for C27H29F3N4O2.HCl.0.15 Et2O.0.55 H2O: C, 59.61; H, 5.91; N, 10.08. Found: C, 59.61; H, 5.57; N, 10.09.

EXAMPLE 7

6(R)- and 6(S)-1-[3-[Spiro-indane-(1,4')-piperidin-1-yl]propyl-aminocarbonyl]-6-(3,4-difluorophenyl)piperidin-2-one Hydrochloride

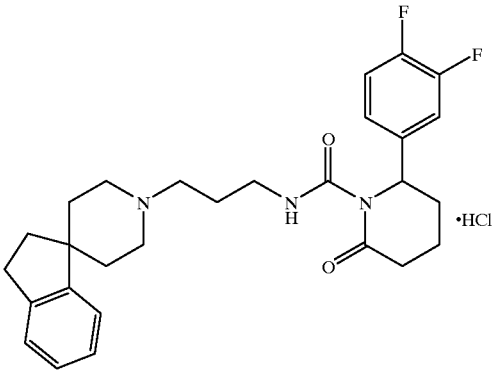

The procedures of Example 4 were carried out using 3-[spiro-indane-(1,4')-piperidin-1-yl] propylamine in place of 3-[4-(4-fluorophenyl)piperidin-1-yl]propylamine dihydrochloride. The racemic product was purified by preparative chiralpak AD HPLC (55:45 hexane:2-propanol which contained 0.1% DEA). The product fractions were evaporated to dryness. Each isomer residue was treated with HCl-saturated ethyl acetate, evaporated to dryness, and reconcentrated three times from diethyl ether to give the title compounds as solids.

Enantiomer A:
m.p.=145–147° C.; NMR: consistent with structure; HPLC: 99.2% pure; FAB MS: M+H @ m/e=482.2; Analysis calc'd for C28H33F2N3O2.HCl.0.75 H2O: C, 63.26; H, 6.73; N, 7.91. Found: C, 63.25; H, 6.54; N, 7.73.

Enantiomer B:
m.p.=140–142° C.; NMR: consistent with structure; HPLC: 100% pure; FAB MS: M+H @ m/e=482.2; Analysis calc'd for C28H33F2N3O2.HCl.0.25 Et2O.0.75 H2O: C, 64.16; H, 6.91; N, 7.74. Found: C, 64.17; H, 6.56; N, 7.74.

EXAMPLE 8

6(R)- and 6(S)-1-[3-[4-(2-Pyridyl)piperidin-1-yl]
propylaminocarbonyl]-6-(3,4-difluorophenyl)
piperidin-2-one Dihydrochloride

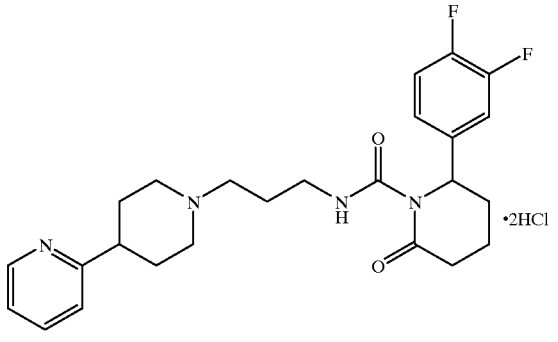

The procedures of Example 4 were carried out using 3-[4-(2-pyridyl)piperidin-1-yl]-propylamine in place of 3-[4-(4-fluorophenyl)piperidin-1-yl]propylamine dihydrochloride. The racemic product was purified by preparative chiralpak AD HPLC (70:30 hexane:2-propanol which contained 0.1% DEA). The product fractions were evaporated to dryness. Each isomer residue was treated with HCl-saturated ethyl acetate, evaporated to dryness, and reconcentrated three times from diethyl ether to give the title compounds as solids.

Enantiomer A:
m.p.=135–139° C.; NMR: consistent with structure; HPLC: 97.6% pure; FAB MS: M+H @ m/e=457.3; Analysis calc'd for C25H30F2N4O2.2HCl.2.25 H2O: C, 52.68; H, 6.45; N, 9.83. Found: C, 52.64; H, 6.06; N, 9.46.

Enantiomer B:
m.p.=135–139° C.; NMR: consistent with structure; HPLC: 99.2% pure; FAB MS: M+H @ m/e=457.3; Analysis calc'd for C25H30F2N4O2.2HCl.0.25 Et2O.1.20 H2O: C, 52.77; H, 6.08; N, 9.47. Found: C, 52.80; H, 6.06; N, 9.36.

EXAMPLE 9

6(R)- and 6(S)-1-[3-[4-(2-cyano-4-fluorophenyl)
piperidin-1-yl]propylaminocarbonyl]-6-(3,4-
difluorophenyl)piperidin-2-one hydrochloride

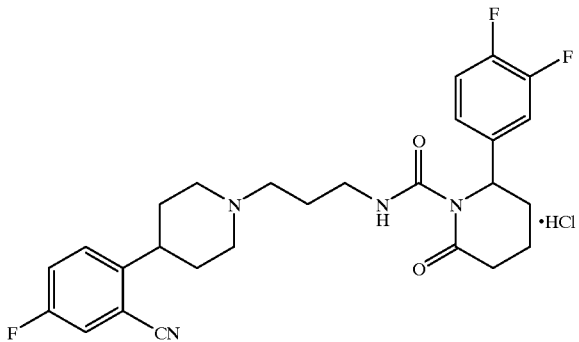

The procedures of Example 4 were carried out using 3-[4-(2-cyano-4-fluorophenyl)piperidin-1-yl]propylamine in place of 3-[4-(4-fluorophenyl)piperidin-1-yl]propylamine dihydrochloride. The racemic product was purified by preparative chiralpak AD HPLC (40:60 hexane:2-propanol which contained 0.1% DEA). The product fractions were evaporated to dryness. Each isomer residue was treated with HCl-saturated ethyl acetate, evaporated to dryness, and reconcentrated three times from diethyl ether to give the title compounds as solids.

Enantiomer A:
m.p.=155–160° C.; NMR: consistent with structure; HPLC: 97.6% pure; FAB MS: M+H @ m/e=499.3; Analysis calc'd for C27H29F3N4)2.HCl.0.30 Et2O.1.40 H2O: C, 58.15; H, 6.20; N, 9.62. Found: C, 58.17; H, 5.80; N, 9.55.

Enantiomer B:
m.p.=155–160° C.; NMR: consistent with structure; HPLC: 100% pure; FAB MS: M+H @ m/e=499.2; Analysis calc'd for C27H29F3N4O2.HCl.0.15 Et2O.1.15 H2O: C, 58.48; H, 6.01; N, 9.88. Found: C, 58.47; H, 5.71; N, 9.68.

EXAMPLE 10

6(R)- and 6(S)-1-[[3(R)-1-[Trans-4-(2-pyridyl)
cyclohexyl]pyrrolidin-3-yl]-aminocarbonyl]-6-(3,4-
difluorophenyl)piperidin-2-one Dihydrochloride

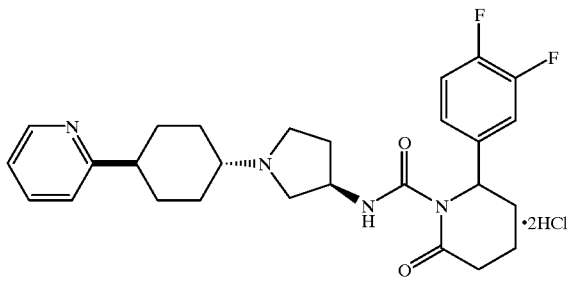

The procedures of Example 4 were carried out using 3(R)-amino-1-[trans-4-(2-pyridyl)cyclohexyl]pyrrolidine in place of 3-[4-(4-fluorophenyl)piperidin-1-yl]propylamine dihydrochloride. The diastereomers were separated by preparative chiralpak AD HPLC (20:80 hexane:ethanol which contained 0.1% DEA). The product fractions were evaporated to dryness. Each isomer residue was treated with HCl-saturated ethyl acetate, evaporated to dryness, and reconcentrated three times from diethyl ether to give the title compounds as solids.

Enantiomer A:
m.p.=100–120° C.; NMR: consistent with structure; HPLC: 100% pure; FAB MS: M+H @ m/e=483.4; Analysis calc'd for C27H32F2N4O2.2HCl.0.40 Et2O.0.95 H2O: C, 55.42; H, 6.33; N, 9.04. Found: C, 55.41; H, 6.09; N, 9.04.

Enantiomer B:
m.p.=90–100° C.; NMR: consistent with structure; HPLC: 100% pure; FAB MS: M+H @ m/e=483.2; Analysis calc'd for C27H32F2N4O2.2HCl.0.75 Et2O.1.50 H2O: C, 54.12; H, 6.51; N, 8.42. Found: C, 54.17; H, 6.51; N, 8.45.

EXAMPLE 11

1-[3-[4-(4-Fluorophenyl)piperidin-1-yl]
propylaminocarbonyl]-6-phenylpiperidin-2-one
Hydrochloride

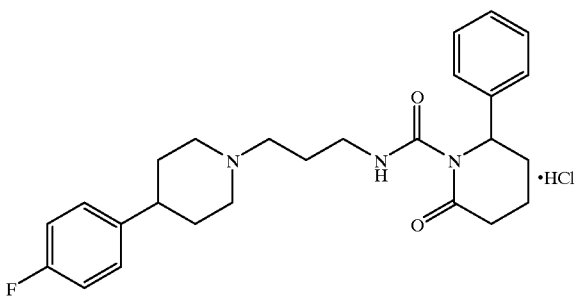

Step 1: 5-Oximino-5-phenylpentanoic Acid 4-benzoylbutyric acid (4.26 g, 22.2 mmol), a 5 mL solution of aqueous hydroxylamine hydrochloride (1.80 g, 25.9 mmol), and a 2.0M solution of aqueous sodium hydroxide (14 mL, 28.0 mmol) were combined in 15 mL of absolute ethanol. The mixture was refluxed at 120° C. for 1 hour, then evaporated in vacuo to remove ethanol. A few drops of a 2.0M solution of aqueous hydrochloric acid were added to the solution to achieve a pH of 6. Then more water was added, and the slurry was filtered to isolate the title compound as a solid.

Step 2: 5-Amino-5-phenylpentanoic Acid 5-oximino-5-phenylpentanoic acid (4.60 g, 22.2 mmol) was dissolved in 150 mL of absolute ethanol. The resulting solution was added to an ethanol suspension of palladium on activated carbon (445 mg). The reaction mixture was hydrogenated at ambient temperature and 50 psi with shaking for 6.5 hours. The resulting solution was treated with 4 mL of a 2.0M solution of aqueous hydrochloric acid and 40 mL of water, filtered over celite to remove the palladium catalyst, and the filtrate was then evaporated to remove ethanol. 2.0M aqueous sodium hydroxide was added to achieve a pH of 7. The aqueous phase was concentrated in vacuo to give the title compound as a mixture with sodium chloride.

Step 3: 6-Phenylpiperidin-2-one 5-amino-5-phenylpentanoic acid was heated neat at 165° C. for 24 hours. The resulting residue was partitioned between dichloromethane and water. The phases were separated and the organic phase was extracted twice with water, dried over sodium sulfate, filtered, and evaporated to dryness. The resulting brown solid was purified by "flash" chromatography (97:3 dichloromethane:methanol). The product fractions were evaporated to dryness to give the title compound as a solid.

Step 4: 1-[3-[4-(4-Fluorophenyl)piperidin-1-yl]propylaminocarbonyl]-6-phenylpiperidin-2-one Hydrochloride A solution 6-phenylpiperidin-2-one (132 mg, 0.753 mmol) in tetrahydrofuran (3 mL) was added to a suspension of 95% sodium hydride (40 mg, 1.67 mmol) in tetrahydrofuran (3 mL). The mixture was stirred at ambient temperature for 30 minutes. The resulting solution was transferred via syringe to a solution of 4-nitrophenylchloroformate (152 mg, 0.754 mmol) in tetrahydrofuran (3 mL) which had previously been chilled to −78° C. The mixture was stirred at −78° C. for 2 hours, then evaporated to dryness. The residue was dissolved in 6 mL of dichloromethane and treated with a solution of 1-(3-aminopropyl)-4-(4-fluorophenyl)piperidine (220 mg, 0.931 mmol) in dichloromethane (4 mL) and triethylamine (209 mL, 1.50 mmol). The yellow reaction mixture was stirred at ambient temperature for 18 hours, and then evaporated to dryness. The resulting solid was purified by "flash" chromatography (98:2 dichloromethane : methanol), and the product fractions were evaporated to dryness. The resulting oil was dissolved in dichloromethane and washed six times with saturated sodium bicarbonate and once with brine. The organic phase was then dried over sodium sulfate, filtered, and the filtrate was evaporated to an oil. This residue was treated with HCl-saturated ethyl acetate, evaporated to dryness, and reconcentrated from diethyl ether twice to give the title compound as a solid.

m.p.=59–65° C.; NMR: consistent with structure; HPLC: 92.6% pure; FAB MS: M+H @ m/e=438.1; Analysis calc'd for C26H32FN3O2.HCl.0.30 H2O.0.30 HCl: C, 64.41; H, 7.21; N, 8.29. Found: C, 64.42; H, 6.97; N, 8.26.

EXAMPLE 12

1-[4-[4-(2-Keto-1-benzimidazolinyl)piperidin-1-yl]
butylaminocarbonyl]-6-phenylpiperidin-2-one
Hydrochloride

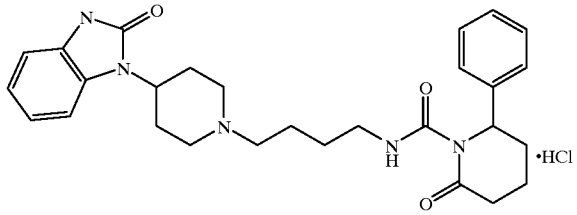

Step 1: 4-(2-Keto-1-benzimidazolinyl)piperidine Butylphthalimide 4-(2-keto-1-benzimidazolinyl)piperidine (1.04 g, 4.79 mmol), N-(4-bromobutyl)-phthalimide (1.59 g, 5.64 mmol) and triethylamine (986 mL, 7.07 mmol) were combined in 10 mL of N,N-dimethylformamide. The reaction mixture was stirred at 50° C. for 18 hours, and then concentrated in vacuo. The residue was partitioned between dichloromethane and saturated sodium bicarbonate. The phases were separated and the organic phase was dried over sodium sulfate, filtered, and evaporated to dryness in vacuo. The resulting solid was purified by "flash" chromatography (95:5:0.5 of dichloromethane:methanol:ammonium hydroxide). The product fractions were evaporated to dryness and reconcentrated twice from diethyl ether to give the title compound as a solid.

Step 2: 4-(2-Keto-1-benzimidazolinyl)piperidine Butylamine 4-(2-keto-1-benzimidazolinyl)piperidine butylphthalimide (1.42 g, 3.39 mmol) was dissolved in 30 mL of methanol. To this solution was added anhydrous hydrazine (426 mL, 13.57 mmol) and the reaction mixture was stirred at ambient temperature for 18 hours. The resulting precipitate was filtered and discarded. The filtrate was evaporated to dryness, and the residue was dissolved in dichloromethane and filtered again. The filtrate was evaporated to dryness to give the title compound as a solid.

Step 3: 1-[4-[4-(2-Keto-1-benzimidazolinyl)piperidin-1-yl]butylaminocarbonyl]-6-phenylpiperidin-2-one Hydrochloride Sodium hydride in mineral oil (60mg of a 60% suspension, 1.50 mmol) was suspended in 3 mL of tetrahydrofuran. To this suspension was added a solution of 6-phenylpiperidin-2-one (134 mg, 0.765 mmol) in tetrahydrofuran (2 mL). The resulting solution was stirred at ambient temperature for 30 minutes, then transferred via syringe to a solution of chorotrimethylsilane (500 mL, 3.94 mmol) in tetrahydrofuran (3 mL) which had already been chilled to −78° C. The reaction mixture was stirred at −78° C. for 2 hours, and then evaporated to dryness. The resulting residue was dissolved in 2 mL of tetrahydrofuran and added to a 3 mL solution of 4-nitrophenylchloroformate (154 mg, 0.764 mmol) in tetrahydrofuran which had already been chilled to 0° C. The reaction mixture was stirred at 0° C. for 30 minutes and then at ambient temperature for 30 minutes. The mixture was evaporated to dryness, and half of the resulting residue (160 mg, 0.470 mmol) was dissolved in 5 mL of dichloromethane. To this solution was added 4-(2-keto-1-benzimidazolinyl)-piperidine butylamine (139 mg, 0.482 mmol) and triethylamine (139 mL, 0.997 mmol). The yellow reaction mixture was stirred at ambient temperature for 18 hours, and then evaporated to dryness. The resulting residue was purified by "flash" chromatography (98:2 dichloromethane:methanol). The product fractions were evaporated to an oil which was treated with HCl-saturated ethyl acetate, evaporated to dryness, and reconcentrated from diethyl ether twice to give the title compound as a solid.

m.p.=137–150° C.; NMR: consistent with structure; HPLC: 98.9% pure; FAB MS: M+H @ m/e=490.4; Analysis calc'd for C28H35N5O3.HCl.1.00 H2O.0.30 Et2O: C, 61.92; H, 7.30; N, 12.37. Found: C, 61.94; H, 7.10; N, 12.36.

EXAMPLE 13

1-[3-(4-Cyano-4-phenylpiperidin-1-yl)propylaminocarbonyl]-6-phenylpiperidin-2-one Hydrochloride

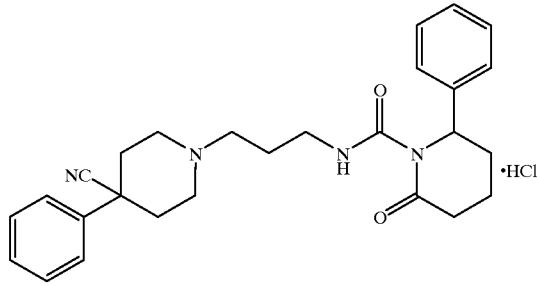

Sodium hydride in mineral oil (60%, 65 mg, 1.63 mmol) was suspended in 3 mL of tetrahydrofuran. To this suspension was added 3 mL of a solution of 6-phenylpiperidin-2-one (235 mg, 1.34 mmol) and the mixture was stirred at ambient temperature for 30 minutes. The resulting solution was transferred via syringe to solution of 4-nitrophenylchloroformate (269 mg, 1.33 mmol) in tetrahydrofuran (4 mL) which had already been chilled to −78° C. The reaction mixture was stirred at −78° C. for 2 hours and then at ambient temperature for 30 minutes. The reaction mixture was then evaporated to dryness. One third of the resulting residue (150 mg, 0.441 mmol) was dissolved in 5 mL of dichloromethane. 4-cyano-4-phenylpiperidine propylamine (113 mg, 0.464 mmol) and triethylamine (139 mL, 0.997 mmol) were added to this solution, and the resulting yellow mixture was stirred at ambient temperature for 18 hours, and then evaporated to dryness. The resulting residue was purified by "flash" chromatography (97:3:0.3 dichloromethane:methanol:ammonium hydroxide). The product fractions were evaporated to give a yellow oil. The residue was purified by "flash" chromatography (1:1 ethyl acetate:hexanes). The product fractions were evaporated to dryness. The residue was then treated with HCl-saturated ethyl acetate, evaporated to dryness, and reconcentrated from diethyl ether twice to give the title compound as a solid.

m.p.=65–70° C.; NMR: consistent with structure; HPLC: 100% pure; FAB MS: M+H @ m/e=445.2; Analysis calc'd for C27H32N4O2.HCl.0.35 Et2O. 0.75 HCl: C, 63.83; H, 7.03; N, 10.49. Found: C, 63.96; H, 6.79; N, 10.48.

EXAMPLE 14

(4R)- and (4S)-4-(3,4-Difluorophenyl)-3-[(4'-(4-fluorophenyl) piperidin-1'-yl)propyl]aminocarbonyltetrahydro-pyrimidin-2-one Hydrochloride

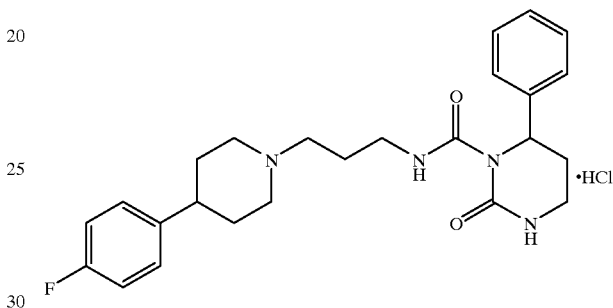

Step 1: 3-Amino-3-(3,4-difluorophenyl)propionic Acid 3,4-Difluorobenzaldehyde (7.76 mL, 70.3 mmol), malonic acid (7.28 g, 70.3 mmol), and ammonium acetate (10.79 g, 140 mmol) were combined in absolute ethanol (30 mL) and refluxed under nitrogen for 6 hours. The mixture was cooled and stirred at ambient temperature overnight. A white solid precipitated which was collected by filtration to yield the title compound.

Step 2: 3-t-Butoxycarbonylamino-3-(3,4-difluorophenyl)propionic Acid

To a slurry of 3-amino-3-(3,4-difluorophenyl)propionic acid (4.2 g, 20 mmol) and di-t-butyldicarbonate (4.56 g, 20 mmol) in 50 mL of THF/water (2:1) was added triethylamine (4.17 mL, 30 mmol) dropwise. The slurry became clear within 5 minutes, and was stirred for an additional 3 hours. The reaction solution was evaporated to dryness and the resulting residue was partitioned between ethyl acetate and 1M HCl. The phases were separated and the organic phase was washed with 1M HCl and brine. The organic layer was dried over sodium sulfate, filtered, and evaporated to dryness. The residue was reconcentrated from hexane, then triturated with hexane and filtered to give the title compound as a solid.

Step 3: 3-t-Butoxycarbonylamino-3-(3,4-difluorophenyl) propionic Acid (R)-(α-methylbenzylamide 3-t-butoxycarbonylamino-3-(3,4-difluorophenyl)propionic acid (5.5 g, 18.3 mmol), (R)-(+)-α-methylbenzylamine (2.95 mL, 22.9 mmol), EDC (4.4 g, 22.9 mmol), and HBT (3.1 g, 22.9 mmol) were combined in DMF (35 mL) under nitrogen. The mixture was adjusted to pH ca. 9 (moistened E. Merck colorpHast indicator) by addition of triethylamine (5.1 mL) and stirred at ambient temperature for 16 hours. The mixture was evaporated to dryness and the residue partitioned between ethyl acetate and saturated sodium bicarconate. The organic layer was washed with saturated sodium bicarbonate and with brine, dried over sodium sulfate, filtered, and evaporated to dryness. The resulting oil was purified by "flash" chromatography (98:2 of methylene chloride:methanol). The product fractions were evaporated to dryness and the residue was reconcentrated from ethyl ether to yield the title compound as a solid.

Step 4: 3-Amino-3-(3,4-Difluorophenyl)propionic Acid (R)-α-methylbenzylamide 3-t-Butoxycarbonylamino-3-(3,4-difluorophenyl) propionic acid (R)-α-methylbenzylamide (6.5 g, 16.1 mmol) was dissolved in 40 mL of ethyl acetate and cooled in an ice bath. The solution was treated with 50 mL of saturated HCl/ethyl acetate solution and allowed to stir for 40 minutes. Nitrogen was bubbled through the reaction solution for 45 minutes, and the mixture was then evaporated to dryness. The resulting residue was reconcentrated from methanol and ethyl ether, and filtered from ethyl ether to yield the title compound as a solid.

Step 5: 3-Amino-3-(3,4-difluorophenyl)-N-((R)-α-methylbenzyl)-Propropylamine

3-Amino-3-(3,4-difluorophenyl)propionic acid (R)-α-methylbenzylamide (4.28 g, 12.6 mmol) was dissolved in THF (190 mL) under nitrogen and treated with 1M borane-THF complex (84 mL, 84 mmol). The reaction solution was heated to reflux for 5 hours and then quenched by slow addition of methanol. Once gas evolution had ceased, 10M HCl (25 mL) was added and the mixture was allowed to stir for 1 hour. The reaction solution was evaporated to dryness. The resulting residue was partitioned between methylene chloride and saturated sodium carbonate. The aqueous phase was separated and extracted with methylene chloride (3X). The combined organic layers were dried over sodium sulfate, filtered, and evaporated to dryness to yield the title compound as an oil.

Step 6: 4-(3,4-Difluorophenyl)-1-((R)-α-methylbenzyl)tetrahydro-pyrimidin-2-One

3-Amino-3-(3,4-difluorophenyl)-N-((R)-α-methylbenzyl)propropylamine (4.08 g, 14.1 mmol) was dissolved in methylene chloride (50 mL) under nitrogen and treated with 1,1-carbonyldiimidazole (4.6 g, 28.4 mmol) in methylene chloride (40 mL) dropwise, over 40 minutes. The reaction was stirred at ambient temperature for 16 hours. The resulting solution was washed with saturated sodium bicarbonate and brine, dried over sodium sulfate, filtered, and evaporated to dryness. The resulting diastereomers were purified and separated by "flash" chromatography (75:25 of ethyl acetate:hexane, followed by 85:15 and ethyl acetate). The product fractions were evaporated to dryness and the residues individually reconcentrated from ethyl ether to yield the corresponding diastereomers as solids.

Step 7: 4-(3,4-Difluorophenyl)-1-((R)-(α-methylbenzyl)-3-[(4-nitrophenyloxy) carbonyl]tetrahydropyrimidin-2-one Potassium bis(trimethylsllyl)amide (0.5M in toluene, 2.9 mL, 1.45 mmol) or potassium hydride (35% in mineral oil, 1.45 mmol) was combined with THF (2 mL) and cooled in an ice bath while under a nitrogen atmosphere. Once cool, the appropriate diastereomer of 4-(3,4-difluorophenyl)-1-((R)-(α-methylbenzyl)-tetrahydropyrimidin-2-one (445 mg, 1.41 mmol) in THF (2 mL) was added dropwise. The mixture was stirred in the cold for 15 minutes and then warmed to ambient temperature for 1 hour. The resulting cloudy reaction mixture was added to a cold solution of 4-nitrophenyl chloroformate (365 mg, 1.81 mmol) in THF (2 mL), dropwise, while under a nitrogen atmosphere. The mixture was stirred in the cold for 15 minutes and then warmed to ambient temperature for 1 hour. The reaction was evaporated to dryness and the resulting residue purified by "flash" chromatography (97:3 of methylene chloride : ethyl ether). The product fractions were evaporated to dryness and the residue was reconcentrated from ethyl ether to yield the title compound as a foam.

Step 8: (4R)- and (4S)-4-(3,4-Difluorophenyl)-1-((R)-α-methylbenzyl)-3-[(4'-(4-fluorophenyl) piperidin-1'-yl) propyl]aminocarbonyltetrahydro-pyrinmidin-2-one Hydrochloride

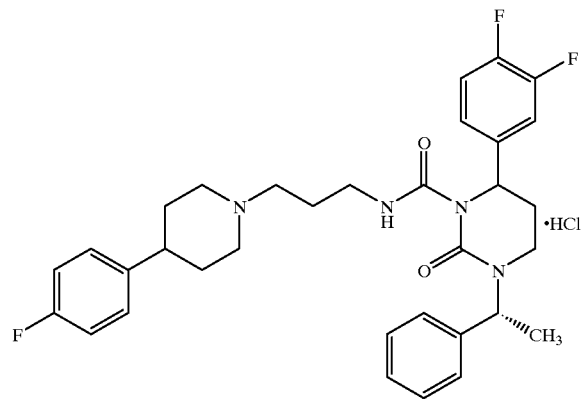

3-(4'-(4-Fluorophenyl)piperidin-1'-yl)propylamine (366 mg, 1.18 mmol), 4-(3,4-difluorophenyl)-1-((R)-(α-methylbenzyl)-3-[(4-nitrophenyloxy) carbonyl]tetrahydro-pyrimidin-2-one (568 mg, 1.18 mmol), and triethylamine (493 uL, 3.54 mmol) were combined in 7 mL of THF. The yellow mixture was stirred at ambient temperature for 18 hours and then evaporated to dryness. The resulting oil was purified by "flash" chromatography (98:2 of methylene chloride:methanol followed by 97:3 and 95:5). The product fractions were evaporated to dryness and the resulting residue was treated with HCl/ethyl acetate. The mixture was evaporated to dryness and the residue reconcentrated from ethyl ether, then triturated with ethyl ether and filtered to give the title compound.

Diastereomer A:
m.p.=97–122° C. (foam); NNMR: consistent with structure; HPLC: 97.58% pure; FAB MS: M+H @ m/e=579; Analysis calc'd for C33H37F3N4O2.HCl.0.45 H2O.0.10 Et2O: C, 63.61; H, 6.38; N, 8.88. Found: C, 63.59; H, 6.35; N, 8.69.

Diastereomer B:
m.p.=215–218° C. (foam); NMR: consistent with structure; HPLC: 98.33% pure; FAB MS: M+H @ m/e=579; Analysis calc'd for C33H37F3N4O2.HCl: C, 64.44; H, 6.23; N, 9.11. Found: C, 64.27; H, 6.05; N, 8.99.

Step 9: (4R)- and (4S)-4-(3,4-Difluorophenyl)-3-[(4'-(4-fluorophenyl)-piperidin-1'-yl)propyl] aminocarbonyltetrahydropyrimidin-2-one Hydrochlorides 4-(3,4-Difluorophenyl)-1-((R)-α-methylbenzyl)-3-[(4'-(4-fluorophenyl) piperidin-1'-yl)propyl] aminocarbonyltetrahydropyrimidin-2-one hydrochloride (81mg, 0.13 mmol) was dissolved in 5 mL of TFA and refluxed for 24–48 hours. The reaction mixture was evaporated to dryness and the resulting residue purified on a Waters Delta Prep 4000 (C18 column, 60 min. run, 45 ml/min., 95:5 to 5:95 of acetonitrile:water (0.1% TFA)). The product fractions were evaporated to dryness and the residue was partitioned between ethyl acetate and saturated sodium bicarbonate. The phases were separated and the water layer was extracted with ethyl acetate (2X). The combined organic layers were washed with brine, dried over sodium sulfate, filtered, and the filtrate evaporated to dryness. The resulting residue was treated with HCl/ethyl acetate and concentrated, and the residue was reconcentrated from ethyl ether to yield the title compound as solid.

Enantiomer A:

m.p.=91–121° C. (foam); NMR: consistent with structure; HPLC: 98.66% pure; FAB MS: M+H @ m/e=475; Analysis calc'd for C25H29F3N4O2.HCl.0.55 H2O.0.10 Et2O: C, 57.74; H, 6.12; N, 10.61. Found: C, 57.72; H, 6.07; N, 10.38.

Enantiomer B:

m.p.=99–138° C. (foam); NMR: consistent with structure; HPLC: 100% pure; FAB MS: M+H @ m/e=475; Analysis calc'd for C25H29F3N4O2.HCl.0.65 H2O.0.05 Et2O: C, 57.49; H, 6.09; N, 10.64. Found: C, 57.48; H, 6.05; N, 10.46.

EXAMPLE 15

The compounds in Table 1 were prepared in the same manner as the title compounds of Step 8 of Example 14, by substituting the appropriate amine for 3-(4'-(4-fluorophenyl) piperidin-1'-yl) propylamine.

EXAMPLE 16

The compounds in Table 2 were prepared in the same manner as the title compounds of Step 9 of Example 14, by using the appropriate (R)-(α-methylbenzyl protected tetrahydro-pyrimidin-2-one in place of 4-(3,4-difluorophenyl)-1-((R)-α-methylbenzyl)-3-[(4'-(4-fluorophenyl) piperidin-1'-yl)propyl]aminocarbonyltetrahydropyrimidin-2-one.

TABLE 1
COMPOUNDS OF EXAMPLE 15
| Amine | Compound | Analysis Data |
|---|---|---|
| 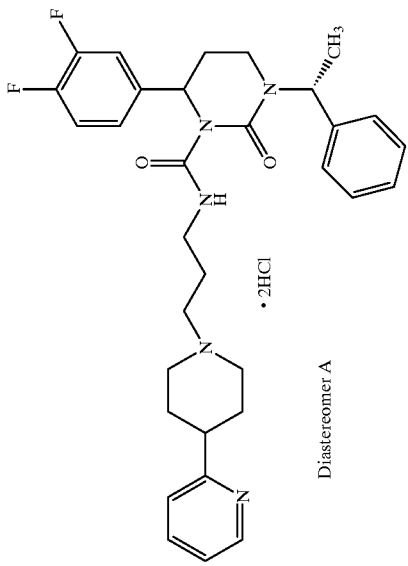 | 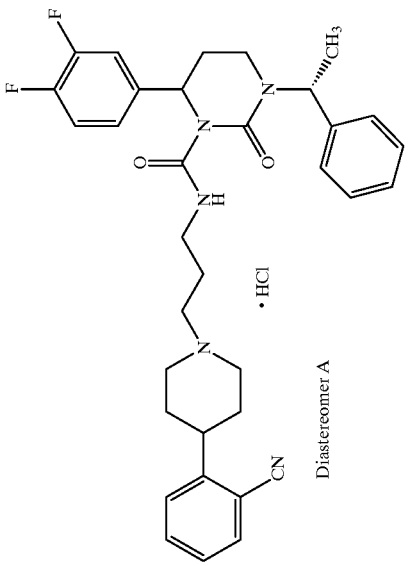<br>Diastereomer A | m.p. = 120–162° C.<br>NMR: consistent with structure<br>HPLC: 99.80% pure<br>FAB MS: M + H @ m/e = 562<br>Analysis calc'd for C32H37F2N5O2.2HCl.1.05 H2O.0.05 Et2O:<br>C, 58.84; H, 6.38; N, 10.66.<br>Found: C, 58.82; H, 6.28; N, 10.63. |
| 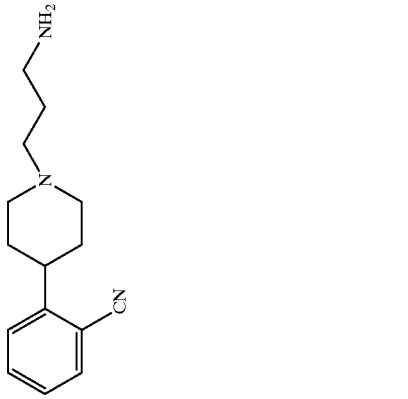 | 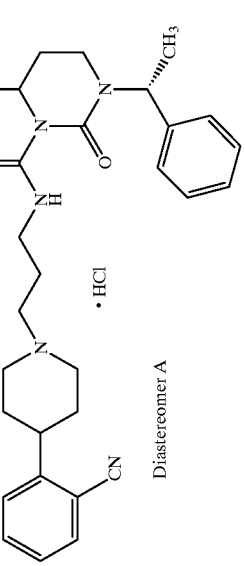<br>Diastereomer A | NMR: consistent with structure<br>HPLC: 99.51% pure<br>FAB MS: M + H @ m/e = 586.3<br>Analysis calc'd for C34H37F2N5O2.HCl.1.15 H2O.0.10 Et2O:<br>C, 63.53; H, 6.40; N, 10.77.<br>Found: C, 63.54; H, 6.30; N, 10.42. |

TABLE 1-continued

COMPOUNDS OF EXAMPLE 15

| Amine | Compound | Analysis Data |
|---|---|---|
| 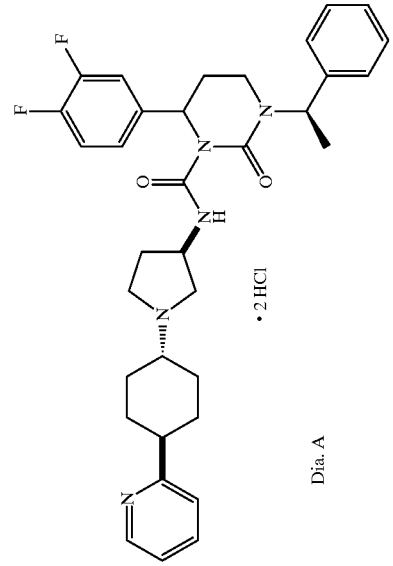 | 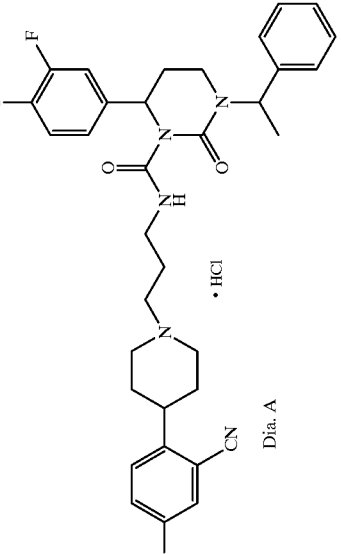 Dia. A | NMR: consistent with structure<br>HPLC: 98.55% pure<br>FAB MS: M + H @ m/e = 588.4<br>Analysis calc'd for<br>C34H39F2N5O2.2HCl.1.40 H2O.0.10 Et2O:<br>C, 59.59; H, 6.51; N, 10.10.<br>Found: C, 59.54; H, 6.59; N, 10.00. |
| 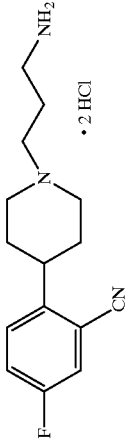 | (structure with Dia. A) | m.p. = 87–108° C. (foam)<br>NMR: consistent with structure<br>HPLC: 97.22% pure<br>FAB MS: M + H @ m/e = 604<br>Analysis calc'd for<br>C34H36F3N5O2.HCl.0.95 H2O:<br>C, 62.13; H, 5.97; N, 10.66.<br>Found: C, 62.09; H, 6.13; N, 10.69. |

TABLE 1-continued

COMPOUNDS OF EXAMPLE 15

| Amine | Compound | Analysis Data |
|---|---|---|
| (structure: 3-amino-pyrrolidine linked to cyclohexyl-2-OMe-4-F-phenyl, ·2 HCl) | (structure: Dia. A, ·HCl) | m.p. = 112–124° C. (foam) NMR: consistent with structure HPLC: 96.25% pure FAB MS: M + H @ m/e = 635 Analysis calc'd for C36H41F3N4O3.HCl.1.0 H2O.0.40 TFA: C, 60.15; H, 6.09; N, 7.63. Found: C, 60.05; H, 6.09; N, 7.72. |

TABLE 2

COMPOUNDS OF EXAMPLE 16

| Starting Material | Compound | Analysis Data |
|---|---|---|
| (structure: 3,4-difluorophenyl dihydropyrimidinone with N-(1-phenylethyl) group and propyl-piperidine-4-(2-chlorophenyl)-4-CN side chain) | (structure: 3,4-difluorophenyl dihydropyrimidinone with NH and propyl-piperidine-4-(2-chlorophenyl)-4-CN side chain) · HCl, Racemic | m.p. = 140–175° C. (foam)<br>NMR: consistent with structure<br>HPLC: 97.60% pure<br>FAB MS: M + H @ m/e = 516.1<br>Analysis calc'd for C26H28ClF2N5O2.HCl.0.35 H2O:<br>C, 55.88; H, 5.36; N, 12.53.<br>Found: C, 55.85; H, 5.32; N, 12.38. |
| (structure: 3,4-difluorophenyl dihydropyrimidinone with N-(1-phenylethyl) group and propyl-piperidine-4-(2-pyridyl) side chain) Diastereomer A | (structure: 3,4-difluorophenyl dihydropyrimidinone with NH and propyl-piperidine-4-(2-pyridyl) side chain) · 2HCl, Enantiomer A | m.p. = 146–180° C. (foam)<br>NMR: consistent with structure<br>HPLC: 99.58% pure<br>FAB MS: M + H @ m/e = 458.3<br>Analysis calc'd for C24H29F2N5O2.2HCl.0.85 H2O:<br>C, 52.81; H, 6.04; N, 12.83.<br>Found: C, 52.84; H, 5.98; N, 12.47. |

TABLE 2-continued

COMPOUNDS OF EXAMPLE 16

| Starting Material | Compound | Analysis Data |
|---|---|---|
| (structure: 3,4-difluorophenyl piperidinone with propyl linker to 4-(2-cyanophenyl)piperidine) Diastereomer A ·HCl | (structure: Enantiomer A) ·HCl | m.p. = 120–150° C. (foam)<br>NMR: consistent with structure<br>HPLC: 99.63% pure<br>FAB MS: M + H @ m/e = 482<br>Analysis calc'd for C26H29F2N5O2·HCl·1.15 H2O:<br>C, 57.96; H, 6.04; N, 13.00.<br>Found: C, 57.97; H, 6.05; N, 13.29. |
| (structure with additional phenyl-CH3 group) Dia. A ·HCl | (structure: Enant. A) ·HCl | NMR: consistent with structure<br>HPLC: 98.05% pure<br>FAB MS: M + H @ m/e = 507.3<br>Analysis calc'd for C27H28F2N6O2·HCl·0.95 H2O:<br>C, 57.89; H, 5.56; N, 15.00.<br>Found: C, 57.86; H, 5.40; N, 14.72. |

TABLE 2-continued

COMPOUNDS OF EXAMPLE 16

| Starting Material | Compound | Analysis Data |
|---|---|---|
| Dia. A (3,4-difluorophenyl pyrimidinone with pyrrolidinyl-cyclohexyl-pyridine, ·2 HCl) | Enant. A (3,4-difluorophenyl pyrimidinone with pyrrolidinyl-cyclohexyl-pyridine, ·2 HCl) | NMR: consistent with structure<br>HPLC: 94.00% pure<br>FAB MS: M + H @ m/e = 484.4<br>Analysis calc'd for C26H31F2N5O2.2HCl.1.20 H2O.0.10 Et2O:<br>C, 54.15; H, 6.27; N, 11.96.<br>Found: C, 54.19; H, 6.26; N, 11.63. |
| Dia. A (3,4-difluorophenyl pyrimidinone with piperidinyl-cyanofluorophenyl, ·HCl) | Enant. A (3,4-difluorophenyl pyrimidinone with piperidinyl-cyanofluorophenyl, ·HCl) | m.p. = 102–134° C. (foam)<br>NMR: consistent with structure<br>HPLC: 98.84% pure<br>FAB MS: M + H @ m/e = 500<br>Analysis calc'd for C26H28F3N5O2.HCl.1.40 H2O:<br>C, 55.64; H, 5.71; N, 12.48.<br>Found: C, 55.68; H, 5.77; N, 12.35. |

EXAMPLE 17

4-(3,4-Difluorophenyl)-1-methyl-3-[(4'-(4-fluorophenyl)piperidin-1'-yl)propyl]aaminocarbonyltetrahydropyrimidin-2-one Hydrochloride

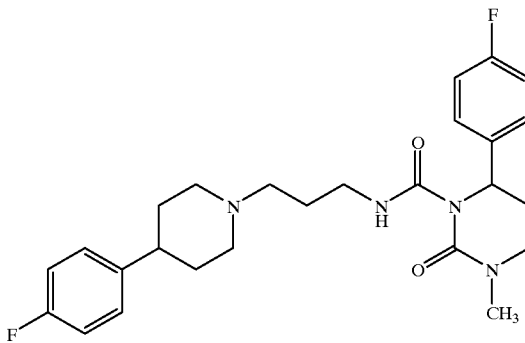

This compound was prepared using the procedures of Example 14, Steps 1–8, substituting methylamine for (R)-(+)-(α-methylbenzylamine in Step 3. The isomers were not separated in Step 6.

m.p.=205–209° C.; NMR: consistent with structure; HPLC: 100% pure; FAB MS: M+H @ m/e=489.2; Analysis calc'd for C26H31F3N4O2.HCl.0.40 H2O: C, 58.67; H, 6.21; N, 10.53. Found: C, 58.70; H, 6.00; N, 10.51.

EXAMPLE 18

(4R)- and (4S)-4-(3,4-Difluorophenyl)-5,5-dimethyl-3-[(4'-(4-fluorophenyl)-piperidin-1'-yl)propyl]aminocarbonyltetrahydropyrimidin-2-one Hydrochloride

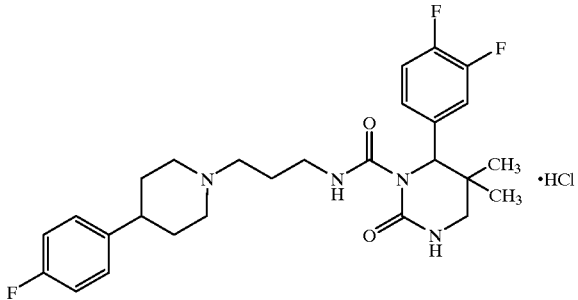

Step 1: (4R)- and (4S)-4-(3,4-Difluorophenyl)-5,5-dimethyl-1-((R)-(α-methylbenzyl)tetrahydro-pyrimidin-2-one 3,4-Difluorobenzaldehyde (1 mL, 9.06 mmol), isobutyraldehyde (830 µL, 9.14 mmol), and R-(+)-1-phenylethylurea (1.5 g, 9.13) were combined in formic acid (3 mL) and refluxed for 16 hours. The reaction mixture was evaporated to dryness. The resulting diastereomers were purified and separated by "flash" chromatography (90:10 of ethyl acetate:hexane). The product fractions were evaporated to dryness and the residues were reconcentrated from ethyl ether to yield the individual diastereomers of the title compound as foams.

Step 2: (4R)- and (4S)-4-(3,4-Difluorophenyl)-5,5-dimethyl-1-((R)-α-methylbenzyl)-3-[(4'-(4-fluorophenyl) piperidin-1'-yl)propyl]aminocarbonyltetrahydropyrimidin-2-one Hydrochlorides The title compounds were prepared using the procedures of Example 14, Steps 7 and 8. The appropriate diastereomer of 4-(3,4-difluorophenyl)-5,5-dimethyl-1-((R)-α-methylbenzyl)tetrahydropyrimidin-2-one was substituted for the appropriate diastereomer of 4-(3,4-difluorophenyl)-1-((R)-(α-methylbenzyl)tetrahydropyrimidin-2-one in step 7. The title compounds were obtained as solids.

Diastereomer A:

m.p.=118–135° C. (foam); NMR: consistent with structure; HPLC: 99.18% pure; FAB MS: M+H @ m/e=607.3; Analysis calc'd for C35H41F3N4O2.HCl.1.0 H2O: C, 63.57; H, 6.71; N, 8.47. Found: C, 63.57; H, 6.72; N, 8.47.

Diastereomer B:

m.p.=232–234° C. (foam); NMR: consistent with structure; HPLC: 99.02% pure; FAB MS: M+H @ m/e=607.3; Analysis calc'd for C35H41F3N4O2.HCl.0.15 H2O: C, 65.08; H, 6.60; N, 8.68. Found: C, 65.06; H, 6.51; N, 8.70.

Step 3: (4R)- and (4S)-4-(3,4-Difluorophenyl)-5,5-dimethyl-3-[(4'-(4-fluorophenyl)piperidin-1'-1)propyl]aminocarbonyltetrahydropyrimidin-2-one Hydrochlorides The title compounds were prepared using the procedure of Example 14, step 9, substituting 4-(3,4-difluorophenyl)-5,5-dimethyl-1-((R)-α-methylbenzyl)-3-[(4'-(4-fluorophenyl)piperidin-1'-yl)propyl]amino-carbonyltetrahydropyrimidin-2-one hydrochloride for 4-(3,4-difluorophenyl)-1-((R)-α-methylbenzyl)-3-[(4'-(4-fluorophenyl) piperidin-1'-yl) propyl]-aminocarbonyltetrahydropyrimidin-2-one hydrochloride.

Enantiomer A:

m.p.=110–153° C. (foam); NMR: consistent with structure; HPLC: 97.58% pure; FAB MS: M+H @ m/e=503.2; Analysis calc'd for C27H33F3N4O2.HCl.1.15 H2O.0.05 Et2O: C, 57.98; H, 6.58; N, 9.94. Found: C, 57.97; H, 6.46; N, 9.69.

Enantiomer B:

m.p.=116–158° C. (foam); NMR: consistent with structure; HPLC: 97.58% pure; FAB MS: M+H @ m/e=503.2; Analysis calc'd for C27H33F3N4O2.HCl.1.55 H2O.0.05 Et2O: C, 57.24; H, 6.64; N, 9.82. Found: C, 57.24; H, 6.45; N, 9.70.

EXAMPLE 19

(4R)- and (4S)-4-(3,4-Difluorophenyl)-5,5-dimethyl-1-benzyl-3-[(4'-(4-fluorophenyl) piperidin-1'-yl)propyl]aminocarbonyltetrahydropyrimidin-2-one Hydrochloride

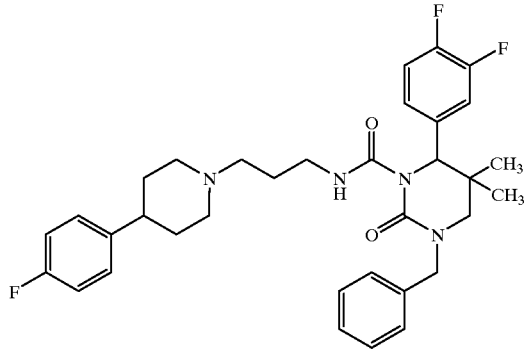

This compound was prepared using the procedures of Example 18, Steps 1 and 2, substituting benzylurea for R-(+)-1-phenylethylurea in Step 1.

m.p.=91–122° C. (foam); NMR: consistent with structure; HPLC: 99.48% pure; FAB MS: M+H @ m/e=593.2; Analysis calc'd for C34H39F3N4)2.HCl.0.90 H2O.0.20 Et2O: C, 63.31; H, 6.69; N, 8.49. Found: C, 63.26; H, 6.80; N, 8.47.

EXAMPLE 20

(4'R)- and (4'S)-Spirocyclohexane-[1,5']-{4-(3,4-difluorophenyl)-3-[(4'-(4-fluorophenyl) piperidin-1'-yl)propyl]aminocarbonyl}tetrahydropyrimidin-2-one Hydrochloride

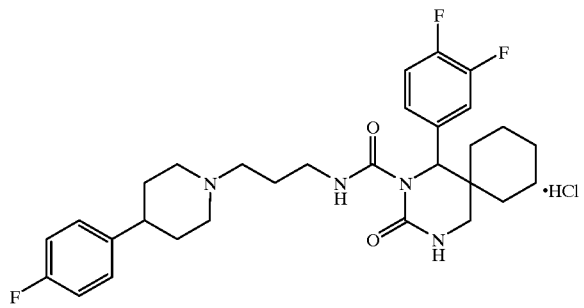

The title compounds were prepared using the procedures of Example 18, Steps 1–3, substituting cyclohexanecarboxaldehyde for isobutyraldehyde in Step 1. The compounds were isolated as solids.

Isomer A:
m.p.=94–118° C. (foam); NMR: consistent with structure; HPLC: 97.0% pure; FAB MS: M+H @ m/e=543.4; Analysis calc'd for C30H37F3N4O2.1.45 HCl.0.45 H2O: C, 59.69; H, 6.57; N, 9.28. Found: C, 59.68; H, 6.39; N, 9.01.

Isomer B:
m.p.=90–112° C. (foam). NMR: consistent with structure; HPLC: 100% pure (contains 12% of Isomer A); FAB MS: M+H @ m/e=543.3; Analysis calc'd for C30H37F3N4O2.HCl.0.55 H2O: C, 61.17; H, 6.69; N, 9.51. Found: C, 61.17; H, 6.93; N, 9.32.

EXAMPLE 21

(4R,5S)-, (4S,5S)-, (4R,5R)-, and (4S,5R)-5-Cyclopropyl-4-(3,4-difluorophenyl [(4'-(4-fluorophenyl)piperidin-1'-yl) propyl]aminocarbonyl-tetrahydropyrimidin-2-one Hydrochloride

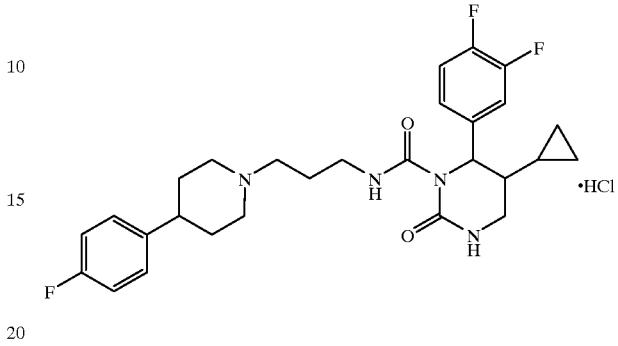

Step 1: 2-Cyclopropyl-3-(3,4-difluorophenyl)-3-hydroxypropionic Acid

To a stirred solution of lithium diisopropylamide (2.0M in hexanes, 46.4 mL, 92.8 mmol) in 20 mL of THF at −40° C. under a nitrogen atmosphere was added cyclopropylacetic acid (4.65g in 20 mL of THF, 46.4 mmol), dropwise. The mixture was stirred in the cold for 15 minutes and warmed to ambient temperature. After 1 hour, the reaction slurry was cooled in an ice bath and 3,4-difluorobenzaldehyde (5.2 mL, 47.1 mmol) in 10 mL of THF was added dropwise. The mixture was warmed to ambient temperature and allowed to stir for 2 hours. The mixture was poured into 200 mL of cold water and the layers separated. The organic layer was washed with water (3X), and the combined aqueous layers were washed with ethyl ether (2X), and then acidified with 3N hydrochloric acid. The water layer was extracted with ethyl ether (3X) and the combined ether layers were dried over sodium sulfate, filtered, and evaporated to dryness to yield the title compound as an oil.

Step 2: 2-Cyclopropyl-3-(3,4-difluorophenyl)-3-hydroxypropionic Acid N-((R)-α-methylbenzyl)amide This compound was prepared using the procedure of Example 14, step 3, substituting 2-cyclopropyl-3-(3,4-difluorophenyl)-3-hydroxypropionic acid for 3-t-butoxycarbonylamino-3-(3,4-difluorophenyl)propionic acid. The individual; diastereomers were separated during flash chromatography (97.5:2.5 methylene chloride:ethyl ether) and each was carried through the following steps.

Step 3: 3-Azido-2-cyclopropyl-3-(3,4-difluorophenyl) propionic Acid N-((R)-α-methylbenzyl)amide The appropriate diastereomer of 2-cyclopropyl-3-(3,4-difluorophenyl)-3-hydroxypropionic acid N-((R)-(α-methylbenzyl)amide (1.1 g, 3.18 mmol), triphenylphosphine (1.7 g, 6.48 mmol), and diphenyl-phosphoryl azide (1.37 mL, 6.36 mmol) were combined in THF (30 mL) and cooled to −78° C. under nitrogen. Diethyl azodicarboxylate (1.2 mL, 7.63 mmol) was added and the mixture was stirred 1 hour at −78, 1 hour at 0° C. and 16 hours at ambient temperature. The reaction mixture was washed with saturated sodium bicarbonate and brine, dried the over sodium sulfate, filtered, and evaporated to dryness. The resulting oil was purified and separated by "flash" chromatography (98:2 of methylene chloride:ethyl ether). The product fractions were evaporated to dryness and the residue was reconcentrated from ethyl ether to yield the title compound as an oil.

Step 4: 3-Amino-2-cyclopropyl-3-(3,4-difluorophenyl)-N-((R)-α-methylbenzyl)-propropylamine The title compound was prepared using the procedure Example 14, step 5, substituting the appropriate diastereomer of 3-azido-2-cyclopropyl-3-(3,4-difluorophenyl) propionic acid N-((R)-α-methylbenzyl)amide for 3-amino-3-(3,4-difluorophenyl)propionic acid N-((R)-(α-methylbenzyl)amide. The title compound was isolated as an oil.

Step 5: 5–Cyclopropyl-4-(3,4-difluorophenyl)-1-((R)-(α-methylbenzyl)tetrahydropyrimidin-2-one The title compound was prepared using the procedure Example 14, Step 6, substituting 3-amino-2-cyclopropyl-3-(3,4-difluorophenyl)-N-((R)-(α-methylbenzyl)-propropylamine for 3-amino-3-(3,4-difluorophenyl)-N-((R)-α-methylbenzyl)-propropylamine. The isomers (cis/trans) were separated using a Waters Delta Prep 4000 (C8 column, 60min. run, 45 mL/min., 95:5 to 5:95 of acetonitrile:water (0.1% TFA)). The individual isomers were each carried through the following steps.

Step 6: (4R,5S)-, (4S,5S)-, (4R,5R)-, and (4S,5R)-5-Cyclopropyl-4-(3,4-difluorophenyl)-3-[(4'-(4-fluorophenyl) piperidin-1'-yl) propyl]aminocarbonyltetrahydropyrimidin-2-one Hydrochlorides The title compounds were prepared using the procedures of Example 14, Steps 7, 8 and 9. The appropriate isomer of 5-cyclopropyl-4-(3,4-difluorophenyl)-1-((R)-α-methylbenzyl)tetrahydropyrimidin-2-one was substituted for the appropriate diastereomer of 4-(3,4-difluorophenyl)-1-((R)-(α-methylbenzyl)tetrahydropyrimidin-2-one in Step 7. The resulting products were carried onto Steps 8 and 9 to yield the title compounds as solids.

Isomer A (trans):

m.p.=68–112° C. (foam); NMR: consistent with structure; HPLC: 99.76% pure; FAB MS: M+H @ m/e=515.4; Analysis calc'd for C28H33F3N4O2.HCl.1.85 H2O: C, 57.54; H, 6.50; N, 9.59. Found: C, 57.47; H, 6.76; N, 9.23.

Isomer B (cis):

m.p.=118–136° C. (foam); NMR: consistent with structure; HPLC: 98.38% pure; FAB MS: M+H @ m/e=515.2; Analysis calc'd for C28H33F3N4O2.HCl.0.70 H2O.0.10 Et2O: C, 59.73; H, 6.42; N, 9.81. Found: C, 59.68; H, 6.39; N, 9.47.

Isomer C (trans):

m.p.=93–120° C. (foam); NMR: consistent with structure; HPLC: 98.44% pure; FAB MS: M+H @ m/e=515.4; Analysis calc'd for C28H33F3N4O2.HCl.1.25 H2O.0.45 HCl: C, 57.00; H, 6.31; N, 9.50. Found: C, 57.09; H, 6.34; N, 9.11.

Isomer D (cis):

m.p.=102–131° C. (foam); NMR: consistent with structure; HPLC: 98.99% pure; FAB MS: M+H @ m/e=515.2; Analysis calc'd for C28H33F3N4O2.HCl.1.15 H2O.0.45 HCl: C, 57.17; H, 6.30; N, 9.53. Found: C, 57.25; H, 6.36; N, 9.14.

EXAMPLE 22

(4R,5S)-, (4S,5S)-, (4R,5R)-, and (4S,5R)-5-Methyl--4-(3,4-difluorophenyl)-3-[(4'-(4-fluorophenyl)piperidin-1'-yl) propyl]aminocarbonyl-tetrahydropyrimidin-2-one Hydrochloride

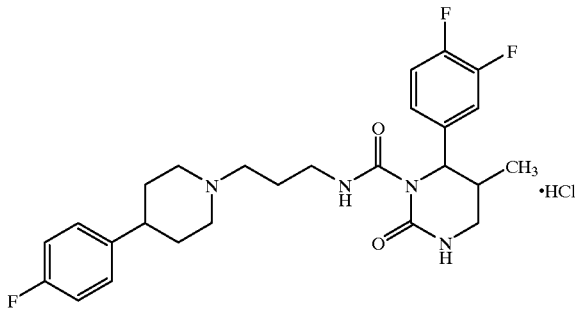

The title compounds were prepared using the procedures of Example 21, Steps 1–6, substituting propionic acid for cyclopropylacetic acid in Step 1. The title compounds were obtained as solids.

Isomer A m.p.=89–113° C. (foam); NMR: consistent with structure; HIPLC: 99.3% pure; FAB MS: M+H @ m/e=489.3; Analysis calc'd for C26H31F3N4O2.HCl.0.65 H2O: C, 58.18; H, 6.25; N, 10.44. Found: C, 58.15; H, 6.22; N, 10.09.

Isomer B:

m.p.=80–105° C. (foam); NMR: consistent with structure; HPLC: 91.28% pure; FAB MS: M+H @ m/e=489.3; Analysis calc'd for C26H31F3N4O2.HCl.0.85 H2O.0.30 Et2O: C, 58.07; H, 6.58; N, 9.96. Found: C, 58.04; H, 6.19; N, 9.64

Isomer C:

m.p.=87–98° C. (foam); NMR: consistent with structure; HPLC: 100% pure; FAB MS: M+H @ m/e=489.3; Analysis calc'd for $C_{26}H31F3N4O2.HCl.1.00$ H2O.0.25 Et2O: C, 57.74; H, 6.55; N, 9.98. Found: C, 57.77; H, 6.23; N, 9.81.

EXAMPLE 23

As a specific embodiment of an oral composition, 100 mg of Isomer D of Example 21 is formulated with sufficient finely divided lactose to provide a total amount of 580 to 590 mg to fill a size O hard gel capsule.

EXAMPLE 24

Screening assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 μl) contained 50 mM Tris-HCl pH. 7.4, 5 mM EDTA, 150 mM NaCl, 100 pM [$^{125}$ I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 25

Selective Binding Assays

Membranes prepared from stably transfected human alpha 1d and alpha 1b cell lines (ATCC CRL 11138 and CRL 11139, respectively) were used to identify compounds that selectively bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

All of the compounds of the present invention prepared in Examples 1–22 were found to have alpha 1a Ki values of less than about 295 nM, as determined via the screening assay described in Example 25. Except for Enatiomer B of Examples 7, 8 and 10 respectively, Example 13, and Example 15, Table 1, entry 4, the compounds of Examples 1–22 were found to have alpha 1a Ki values of less than about 20 nM. All of the compounds of Examples 1–22 exhibited selectivity for the alpha 1a receptor with respect to both the alpha 1b and alpha 1d receptors.

The compounds of the following Examples were found to be at least about 10-fold more selective in binding to alpha 1a receptors versus binding to the alpha 1b and alpha 1d receptors:

Example 1,
Example 2 (Enantiomer A),
Example 3 (Isomers A and C),
Examples 4 and 5,
Example 6 (Enantiomer A),
Example 7 (Enantiomer A),
Examples 8 and 9,
Example 10 (Enantiomer A),
Example 14 (Step 8, Diastereomer A and Step 9, Enantiomer A),
Example 15 (Table 1, entries 1, 2 and 5),
Example 16 (Table 2, all entries),
Example 17,
Example 18 (Step 2, Diastereomer A and Step 3, Enantiomers A and B),
Example 19,
Example 20 (Isomer B),
Example 21 (Isomers A, C and D), and
Example 22 (Isomers B and C)

EXAMPLE 26

Counterscreen: Histamine-1 Selectivity

The binding affinity (Ki in nM) of the compounds of the present invention for histamine H1 receptors can determined via the binding assay described in Chang et al., *J. Neurochem.* (1979), 32: 1653, or as described in U.S. Pat. No. 5,403,847, or suitable modifications thereof known to those skilled in the art. The assay can be used to eliminate agents which specifically affect binding to hH1 receptors.

EXAMPLE 27

EXEMPLARY COUNTERSCREENS

1. Assay Title: Dopamine D2, D3, D4 In Vitro Screen

Objective of the Assay:
The objective of this assay is to eliminate agents which specifically affect binding of [3H] spiperone to cells expressing human dopamine receptors D2, D3 or D4.

Method:
Modified from VanTol et al., *Nature* (1991), 350: 610–613.

Frozen pellets containing specific dopamine receptor subtypes stably expressed in clonal cell lines are lysed in 2 ml lysing buffer (10 mM Tris-HC/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 µg membranes in a total volume of 500 µl containing 0.2 nM [3H]-spiperone. Non-specific binding is defined using 10 µM apomorphine. The assay is terminated after a 2 hour incubation at room temperature by rapid filtration over GF/B filters presoaked in 0.3% PEI, using 50 mM Tris-HCl pH 7.4.

2. Assay Title: Serotonin 5HT1a

Objective of the Assay
The objective of this assay is to eliminate agents which specifically affect binding to cloned human 5HT1a receptor Method:
Modified from Schelegel and Peroutka, *Biochemical Pharmacology* (1986), 35: 1943–1949.

Mammalian cells expressing cloned human 5HT1a receptors are lysed in ice-cold 5 mM Tris-HCI, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl2 and 1 mg/ml ascorbate. Non-specific binding is defined using 10 µM propranolol. The assay is terminated after a 1 hour incubation at room temperature by rapid filtration over GF/Cfilters

EXAMPLE 28

EXEMPLARY FUNCTIONAL ASSAYS

In order to confirm the specificity of compounds for the human alpha 1a adrenergic receptor and to define the biological activity of the compounds, the following functional tests may be performed:

1. In vitro Rat, Dog and Human Prostate and Dog Urethra

Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; CaCl$_2$, 2.5 mM; KH$_2$PO$_4$, 1.2 mM; MgSO$_4$, 1.2 mM; NaHCO$_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/ 95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 μM (for rat), 10 μM (for dog) and 20 μM (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. $pA_2$ (-log Kb) values were obtained from Schild plot when three or more concentrations were tested. When less than three concentrations of antagonist are tested, $K_b$ values are calculated according to the following formula $$K_b = \frac{[B]}{x-1},$$

where x is the ratio of $EC_{50}$ of agonist in the presence and absence of antagonist and [B] is the antagonist concentration.

2. Measurement of Intra-Urethral Pressure in Anesthetized Dogs

PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of formula:

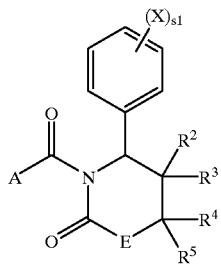

wherein A is

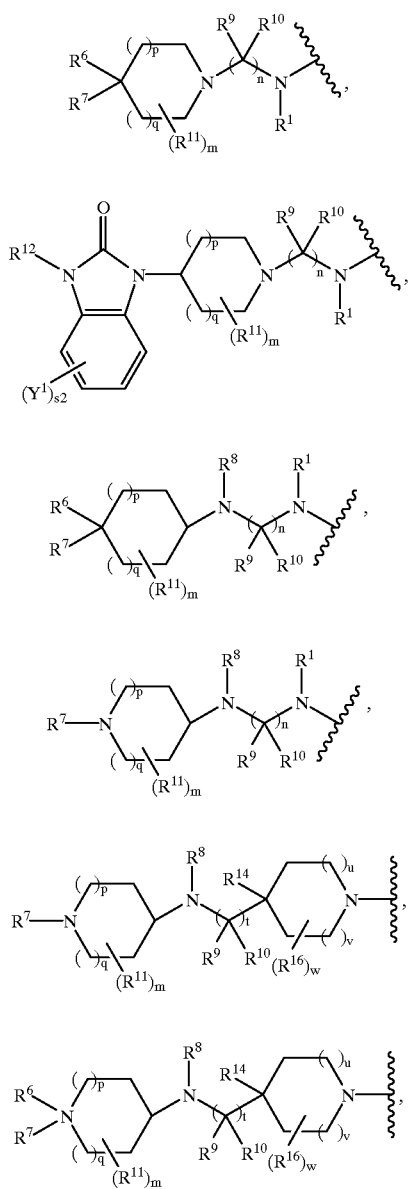

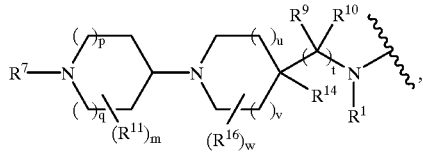

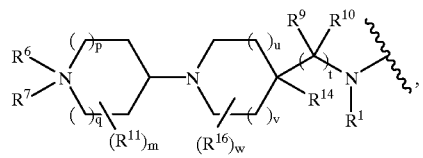

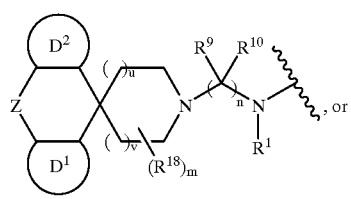

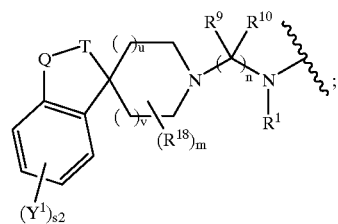

E is $CR^aR^b$ or $NR^c$;

$R^1$ is hydrogen, $C_1-C_6$ alkyl, fluorinated $C_1-C_6$ alkyl, $C_3-C_8$ cycloalkyl, fluorinated $C_3-C_8$ cycloalkyl, $C_4-C_{20}$ alkylcycloalkyl, or $C_4-C_{20}$ cycloalkylalkyl;

$R^2$, $R^3$, $R^4$ and $R^5$ are as follows:

(i) $R^2$ and $R^3$ are each independently selected from hydrogen, cyano, $C_1-C_6$ alkyl, fluorinated $C_1-C_6$ alkyl, $C_3-C_8$ cycloalkyl, fluorinated $C_3-C_8$ cycloalkyl, $C_4-C_{20}$ alkylcycloalkyl, $C_4-C_{20}$ cycloalkylalkyl, fluorinated $C_4-C_{20}$ alkylcycloalkyl, fluorinated $C_4-C_{20}$ cycloalkylalkyl, $(CH_2)_{0-4}CO_2R^d$, $(CH2)_{0-4}OR^d$, and $(CH_2)_{0-4}CON(R^d)_2$; and $R^4$ and $R^5$ are each independently selected from hydrogen, $C_1-C_6$ alkyl, fluorinated $C_1-C_6$ alkyl, $C_3-C_8$ cycloalkyl, fluorinated $C_3-C_8$ cycloalkyl, $C_4-C_{20}$ alkylcycloalkyl, $C_4-C_{20}$ cycloalkylalkyl, and $(CH_2)_{0-4}OR^d$;

(ii) $R^2$ and $R^3$ together with the carbon atom to which they are attached form $C_4-C_6$ cycloalkyl or substituted $C_4-C_6$ cycloalkyl, wherein the each of the substituents on substituted cycloalkyl is hydrogen, halogen, cyano, $C_1-C_6$ alkyl, fluorinated $C_1-C_6$ alkyl, $C_1-C_6$ alkoxy, fluorinated $C_1-C_6$ alkoxy, $CO_2R^d$, $C_2-C_8$ alkoxyalkyl, or fluorinated $C_2-C_8$ alkoxyalkyl; and $R^4$ and $R^5$ are as defined in (i); or (iii) $R^2$ and $R^4$ together with the carbon atoms to which each is attached form $C_4-C_6$ cycloalkyl or substituted $C_4-C_6$ cycloalkyl, wherein the each of the substituents on the substituted cycloalkyl is hydrogen, halogen, cyano, $C_1-C_6$ alkyl, fluorinated $C_1-C_6$ alkyl, $C_1-C_6$ alkoxy, fluorinated $C_1-C_6$ alkoxy, $CO_2R^d$, $C_2-C_8$ alkoxyalkyl, or fluorinated $C_2-C_8$ alkoxyalkyl; and $R^3$ and $R^5$ are as defined in (i);

$R^6$ is hydrogen, cyano, hydroxy, $CO_2R^e$, $CON(R^e)_2$, aryl, or substituted aryl;

$R^7$ is aryl, substituted aryl, heterocyclic, or substituted heterocyclic;

$R^8$ is hydrogen or $C_1$–$C_4$ alkyl;

$R^9$ and $R^{10}$ are each independently selected from hydrogen, $C_1$–$C_6$ alkyl, and $C_3$–$C_8$ cycloalkyl;

each $R^{11}$ is a substituent connected to a ring atom other than $CR^6R^7$ or N and is independently hydrogen or $C_1$–$C_4$ alkyl;

$R^{12}$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, or $C_4$–$C_{20}$ cycloalkylalkyl;

$R^{14}$ is hydrogen or $OR^e$;

each $R^{16}$ is a substituent connected to a ring atom other than N or the carbon to which $R^{14}$ is attached and is independently hydrogen or $C_1$–$C_4$ alkyl;

each $R^{18}$ is a substituent connected to a ring atom other than N or spiro subsituted carbon and is independently hydrogen or $C_1$–$C_4$ alkyl;

$D^1$ is a benzene ring, or a substituted benzene, wherein each of the substituents on the substituted benzene is independently halogen, cyano, $C_1$–$C_8$ alkyl, $C_3$–$C_8$ cycloalkyl, fluorinated $C_1$–$C_8$ alkyl, fluorinated $C_3$–$C_8$ cycloalkyl, $C_1$–$C_6$ alkoxy, fluorinated $C_1$–$C_6$ alkoxy, $C_2$–$C_8$ alkoxyalkyl, or fluorinated $C_2$–$C_8$ alkoxyalkyl;

$D^2$ independently has the same definition as set forth for $D^1$;

Q is absent, $[C(R^{a'}R^{b'})]_{1-4}$, $O[C(R^{a'}R^{b'})]_{1-2}$, $[C(R^{a'}R^{b'})]_{1-2}O$, $C(R^{a'})=C(R^{b'})$, $C(R^{a'}R^{b'})=C(R^{a'})=C(R^{b'})$, or $C(R^{a'})=C(R^{b'})$—$C(R^{a'}R^{b'})$;

T is absent, C(=O), C(=O)O, $N(SO_2R^{c'})C(R^{a'}R^{b'})$, $N(R^{c'})C=O$, or $N(R^{c'})C(=O)O$, provided that (i) when T is absent, Q is $[C(R^{a'}R^{b'})]_{2-4}$, $O[C(R^{a'}R^{b'})]_{1-2}$, $[C(R^{a'}R^{b'})]_{1-2}O$, $C(R^{a'})=C(R^{b'})$, $C(R^{a'}R^{b'})$—$C(R^{a'})=C(R^{b'})$, or $C(R^{a'})=C(R^{b'})$—$C(R^{a'}R^{b'})$; (ii) when T is C(=O) or C(=O)O, Q is $C(R^{a'}R^{b'})$ or $C(R^{a'}R^{b'})C(R^{a'}R^{b'})$; and (iii) when T is $N(SO_2R^{c'})C(R^{a'}R^{b'})$, $N(R^{c'})C=O$, or $N(R^{c'})C(=O)O$, Q is absent or $C(R^{a'}R^{b'})$;

each X is independently hydrogen, halogen, cyano, $C_1$–$C_6$ alkyl, fluorinated $C_1$–$C_6$ alkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

each $Y^1$ is independently hydrogen, halogen, cyano, $C_1$–$C_6$ alkyl, fluorinated $C_1$–$C_6$ alkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

Z is absent, O, S, SO, $SO_2$, $NR^h$, C=O, $NR^hC(=O)$, $C(=O)NR^h$, $NR^hSO_2$, $SO_2NR^h$, $C(R^fR^g)$, $C(R^fR^g)C(R^fR^g)$, $C(R^f)=C(R^g)$, $C(R^fR^g)S$, $SC(R^fR^g)$, $C(R^fR^g)SO$, $SOC(R^fR^g)$, $C(R^fR^g)NR^h$, $NR^hC(R^fR^g)$, $C(R^fR^g)C(=O)$, or $C(=O)C(R^fR^g)$;

$R^a$ and $R^b$ are each independently selected from hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl and $C_4$–$C_{20}$ cycloalkylalkyl;

$R^c$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, $C_4$–$C_{20}$ cycloalkylalkyl, or $CHR^{k1}R^{k2}$;

$R^{a'}$, $R^{b'}$ and $R^{c'}$ are each independently selected from hydrogen, $C_1$–$C_4$ alkyl, and fluorinated $C_1$–$C_4$ alkyl;

$R^d$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, or $C_4$–$C_{20}$ cycloalkylalkyl;

$R^e$ is hydrogen, $C_1$–$C_6$ alkyl, $C_3$–$C_6$ cycloalkyl, or fluorinated $C_1$–$C_6$ alkyl;

$R^f$ and $R^g$ are each independently selected from hydrogen, $C_1$–$C_6$ alkyl, $C_3$–$C_6$ cycloalkyl, fluorinated $C_1$–$C_6$ alkyl, phenyl, and substituted phenyl, wherein each of the substituents on substituted phenyl is independently halo, $C_1$–$C_6$ alkyl, fluorinated $C_1$–$C_6$ alkyl, $C_1$–$C_6$ alkoxy, fluorinated $C_1$–C alkoxy, $(CH_2)_{0-4}CO_2R^d$, $C_2$–$C_8$ alkoxyalkyl, or fluorinated $C_2$–$C_8$ alkoxyalkyl;

$R^h$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $C_4$–$C_{20}$ alkylcycloalkyl, or $C_4$–$C_{20}$ cycloalkylalkyl;

$R^{k1}$ is hydrogen or $C_1$–$C_6$ alkyl;

$R^{k2}$ is phenyl or substituted phenyl, wherein each of the substituents on substituted phenyl is halogen, cyano, $C_1$–$C_6$ alkyl, fluorinated $C_1$–$C_6$ alkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

m is an integer from 0 to 4;

n is an integer from 2 to 6;

p and q are 1;

u and v are independently 0 or 1;

s1 is an integer from 0 to 5;

s2 is an integer from 0 to 4;

t is an integer from 0 to 3, provided that when t is zero, $R^{14}$ is hydrogen;

w is an integer from 0 to 4; and provided that when A is of formula (a1), then $R^1$ is hydrogen;

$R^2$ and $R^3$ are each independently selected from hydrogen, methyl, ethyl, and cyclopropyl; or $R^2$ and $R^3$ together with the carbon atom to which they are attached form $C_4$–$C_6$ cycloalkyl;

$R^4$ and $R^5$ are each independently selected from hydrogen, methyl, and ethyl;

$R^6$ is hydrogen or cyano;

$R^7$ is phenyl, substituted phenyl, or pyridyl; wherein each of the substituents on substituted phenyl is independently halogen or cyano;

$R^9$ and $R^{10}$ are both hydrogen;

each X is independently hydrogen or fluorine;

$R^a$ and $R^b$ are each independently selected from hydrogen, methyl, and ethyl;

$R^c$ is hydrogen, methyl, ethyl, benzyl, or α-methylbenzyl;

m is zero;

n is 3; and s1 is an integer from 0 to 2;

or a pharmaceutically acceptable salt thereof.

2. The compound according to claim 1, wherein $R^6$ is hydrogen, cyano, hydroxy, $CO_2R^e$, $CON(R^e)_2$, phenyl, or substituted phenyl; wherein each of the substituents on substituted phenyl is independently halo, cyano, hydroxy, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

$R^7$ is phenyl, substituted phenyl, naphthyl, or substituted naphthyl, wherein each of the substituents on substituted phenyl or substituted naphthyl is independently halo, cyano, hydroxy, $C_1$–$C_6$ alkyl, fluorinated $C_1$–$C_6$ alkyl, $C_3$–$C_8$ cycloalkyl, fluorinated $C_3$–$C_8$ cycloalkyl, $C_1-C_6$ alkoxy, fluorinated $C_1-C_6$ alkoxy, $(CH_2)_{0-4}$ $CO_2R^d$, $C_2-C_8$ alkoxyalkyl, or fluorinated $C_2-C_8$ alkoxyalkyl; or pyridyl, pyrazinyl, thienyl, or furanyl; or substituted pyridyl, pyrazinyl, thienyl, or furanyl, wherein each of the substituents on substituted pyridyl, pyrazinyl, thienyl, or furanyl is independently halogen, cyano, $N(R^d)_2$, $(CH_2)_{0-4}C(=O)N(R^d)_2$, $(CH_2)_{0-4}SO_2N(R^d)_2$, $(CH_2)_{0-4}SO_2R^d$, phenyl, $C_1-C_6$ alkyl, fluorinated $C_1-C_6$ alkyl, $C_3-C_8$ cycloalkyl, fluorinated $C_3-C_8$ cycloalkyl, $C_1-C_6$ alkoxy, fluorinated $C_1-C_6$ alkoxy, $(CH_2)_{0-4}CO_2R^d$, $C_2-C_8$ alkoxyalkyl, or fluorinated $C_2-C_8$ alkoxyalkyl;

one of $R^9$ and $R^{10}$ is hydrogen, and the other of $R^9$ and $R^{10}$ is hydrogen or $C_1-C_6$ alkyl;

provided that when A is of formula (a1), then $R^1$ is hydrogen;

$R^2$ and $R^3$ are each independently selected from hydrogen, methyl, ethyl, and cyclopropyl; or $R^2$ and $R^3$ together with the carbon atom to which they are attached form $C_4-C_6$ cycloalkyl;

$R^4$ and $R^5$ are each independently selected from hydrogen, methyl, and ethyl;

$R^6$ is hydrogen or cyano;

$R^7$ is phenyl, substituted phenyl, or pyridyl; wherein each of the substituents on substituted phenyl is independently halogen or cyano;

$R^9$ and $R^{10}$ are both hydrogen;

each X is independently hydrogen or fluorine;

$R^a$ and $R^b$ are each independently selected from hydrogen, methyl, and ethyl;

$R^c$ is hydrogen, methyl, ethyl, benzyl, or α-methylbenzyl;

m is zero;

n is 3;

s1 is an integer from 0 to 2;

or a pharmaceutically acceptable salt thereof.

3. The compound according to claim 2, wherein $R^1$ is hydrogen, $C_1-C_4$ alkyl, or fluorinated $C_1-C_4$ alkyl;

$R^6$ is hydrogen, cyano, hydroxy, $CO_2R^e$, $CON(R^e)_2$, phenyl, or mono- or di- or tri-substituted phenyl;

$R^7$ is phenyl, mono- or di- or tri-substituted phenyl, pyridyl, pyrazinyl, substituted pyridyl, or substituted pyrazinyl;

$R^9$ and $R^{10}$ are both hydrogen;

$R^{14}$ is hydrogen;

m and w are each zero; and provided that when A is of formula (a1), then $R^1$ is hydrogen;

$R^2$ and $R^3$ are each independently selected from hydrogen, methyl, ethyl, and cyclopropyl; or $R^2$ and $R^3$ together with the carbon atom to which they are attached form $C_4-C_6$ cycloalkyl;

$R^4$ and $R^5$ are each independently selected from hydrogen, methyl, and ethyl;

$R^6$ is hydrogen or cyano;

$R^7$ is phenyl, substituted phenyl, or pyridyl; wherein each of the substituents on substituted phenyl is independently halogen or cyano;

each X is independently hydrogen or fluorine;

$R^a$ and $R^b$ are each independently selected from hydrogen, methyl, and ethyl;

$R^c$ is hydrogen, methyl, ethyl, benzyl, or (x-methylbenzyl;

n is 3;

s1 is an integer from 0 to 2;

or a pharmaceutically acceptable salt thereof.

4. The compound according to claim 3, wherein the compound is of formula

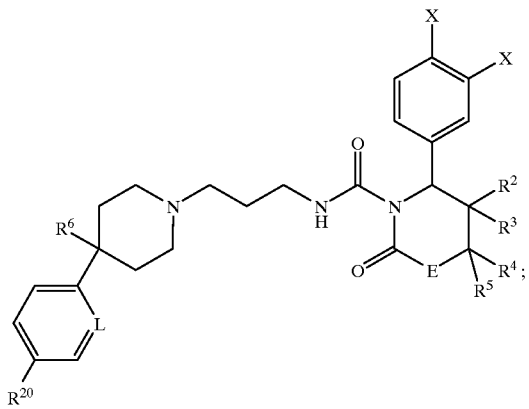

wherein E is $CR^aR^b$ or $NR^c$;

L is N or $CR^{20}$;

$R^2$ and $R^3$ are each independently selected from hydrogen, methyl, and cyclopropyl; or $R^2$ and $R^3$ together with the carbon atom to which they are attached form cyclohexyl;

$R^4$ and $R^5$ are each independently selected from hydrogen and methyl;

$R^6$ is hydrogen or cyano;

each $R^{20}$ is independently hydrogen, halogen, or cyano;

each X is independently hydrogen or fluorine;

$R^a$ and $R^b$ are each independently selected from hydrogen and methyl; and $R^c$ is hydrogen, methyl, ethyl, benzyl, or α-methylbenzyl;

or a pharmaceutically acceptable salt thereof.

5. The compound according to claim 4, wherein E is $CR^aR^b$; or a pharmaceutically acceptable salt thereof.

6. The compound according to claim 5, wherein the compound is selected from the group consisting of:

(6R)-1-[3-[4-(4-fluorophenyl)piperidin-1-yl] propylamino-carbonyl]-6-(3,4-difluorophenyl)-3,3-dimethylpiperidin-2-one;

(6S)-1-[3-[4-(4-fluorophenyl)piperidin-1-yl] propylamino-carbonyl]-6-(3,4-difluorophenyl)-3,3-dimethylpiperidin-2-one;

(6R)-1-[3-[4-(4-fluorophenyl)piperidin-1-yl] propylamino-carbonyl]-6-(3,4-difluorophenyl)-4,4-dimethylpiperidin-2-one;

(6S)-1-[3-[4-(4-fluorophenyl)piperidin-1-yl] propylamino-carbonyl]-6-(3,4-difluorophenyl)-4,4-dimethylpiperidin-2-one;

(4R,6R)-1-[3-[4-(4-fluorophenyl)piperidin-1-yl] propylaminocarbonyl]-6-(3,4-difluorophenyl)-4-methylpiperidin-2-one;

(4S,6R)-1-[3-[4-(4-fluorophenyl)piperidin-1-yl] propylaminocarbonyl]-6-(3,4-difluorophenyl)-4-methylpiperidin-2-one;

(4R,6S)-1-[3-[4-(4-fluorophenyl)piperidin-1-yl] propylaminocarbonyl]-6-(3,4-difluorophenyl)-4-methylpiperidin-2-one;

(4S,6S)-1-[3-[4-(4-fluorophenyl)piperidin-1-yl] propylaminocarbonyl]-6-(3,4-difluorophenyl)-4-methylpiperidin-2-one;

6(S)-1-[3-[4-(4-fluorophenyl)piperidin-1-yl]-propylaminocarbonyl]-6-(3,4-difluorophenyl) piperidin-2-one;

(6RS)-1-[3-[4-(4-fluorophenyl)piperidin-1-yl]-propylaminocarbonyl]-6-(3,4-difluorophenyl) piperidin-2-one;

6(R)-1-[3-[4-(4-fluorophenyl)piperidin-1-yl]-propylaminocarbonyl]-6-(3,4-difluorophenyl) piperidin-2-one;

(6RS)-1-[3-[4-(2-cyanophenyl)-4-cyanopiperidin-1-yl]-propylaminocarbonyl]-6-(3,4-difluorophenyl) piperidin-2-one;

6(R)-1-[3-[4-(2-cyanophenyl)-4-cyanopiperidin-1-yl]-propylaminocarbonyl]-6-(3,4-difluorophenyl) piperidin-2-one;

6(S)-1-[3-[4-(2-cyanophenyl)-4-cyanopiperidin-1-yl]-propylaminocarbonyl]-6-(3,4-difluorophenyl) piperidin-2-one;

6(R)-1-[3-[4-(4-fluorophenyl)-4-cyanopiperidin-1-yl] propyl-aminocarbonyl]-6-(3,4-difluorophenyl) piperidin-2-one;

6(S)-1-[3-[4-(4-fluorophenyl)-4-cyanopiperidin-1-yl] propyl-aminocarbonyl]-6-(3,4-difluorophenyl) piperidin-2-one;

6(R)-1-[3-[4-(2-pyridyl)piperidin-1-yl] propylaminocarbonyl]-6-(3,4-difluorophenyl) piperidin-2-one;

6(S)-1-[3-[4-(2-pyridyl)piperidin-1-yl] propylamninocarbonyl]-6-(3,4-difluorophenyl) piperidin-2-one;

6(R)-1-[3-[4-(2-cyano-4-fluorophenyl)piperidin-1-yl] propylaminocarbonyl]-6-(3,4-difluorophenyl) piperidin-2-one;

6(S)-1-[3-[4-(2-cyano-4-fluorophenyl)piperidin-1-yl] propylaminocarbonyl]-6-(3,4-difluorophenyl) piperidin-2-one;

1-[3-[4-(4-fluorophenyl)piperidin-1-yl] propylaminocarbonyl]-6-phenylpiperidin-2-one;

1-[3-(4-cyano-4-phenylpiperidin-1-yl) propylaminocarbonyl]-6-phenylpiperidin-2-one;

and pharmaceutically acceptable salts thereof.

7. The compound according to claim 4, wherein E is $NR^c$; or a pharmaceutically acceptable salt thereof.

8. The compound according to claim 7, wherein the compound is selected from the group consisting of:

(4R)-4-(3,4-difluorophenyl)-3-[(4'-(4-fluorophenyl) piperidin-1'-yl)propyl]aminocarbonyltetrahydro-pyrimidin-2-one;

(4S)-4-(3,4-difluorophenyl)-3-[(4'-(4-fluorophenyl) piperidin-1'-yl)propyl]aminocarbonyltetrahydro-pyrimidin-2-one;

(4R)-4-(3,4-difluorophenyl)-1-((R)-α-methylbenzyl)-3-[(4'-(4-fluorophenyl) piperidin-1'-yl)propyl] aminocarbonyltetrahydro-pyrimidin-2-one;

(4S)-4-(3,4-difluorophenyl)-1-((R)-α-methylbenzyl)-3-[(4'-(4-fluorophenyl) piperidin-1'-yl)propyl] aminocarbonyltetrahydro-pyrimidin-2-one;

4-(3,4-difluorophenyl)-1-((R)-(α-methylbenzyl)-3-[(4'-(2-pyridyl)piperidin-1'-yl)propyl] aminocarbonyltetrahydropyrimidin-2-one;

4-(3,4-difluorophenyl)-1-((R)-(α-methylbenzyl)-3-[(4'-(4-fluoro-2-cyanophenyl) piperidin-1'-yl)propyl] aminocarbonyltetrahydro-pyrimidin-2-one;

4-(3,4-difluorophenyl)-1-((R)-α-methylbenzyl)-3-[(4'-(2-cyanophenyl) piperidin-1'-yl)propyl] aminocarbonyltetrahydro-pyrimidin-2-one;

4-(3,4-difluorophenyl)-3-[(4'-cyano-4'-(2-chlorophenyl) pipelidin-1'-yl)propyl] aminocarbonyltetrahydropyrimidin-2-one;

4-(3,4-difluorophenyl)-3-[(4'-(2-pyridyl)piperidin-1'-yl) propyl]aminocarbonyltetrahydropyrimidin-2-one;

4-(3,4-difluorophenyl)-3-[(4'-(2-cyanophenyl)piperidin-1'-yl)propyl]aminocarbonyltetrahydropyrimidin-2-one;

4-(3,4-difluorophenyl)-3-[(4'-cyano-4'-(2-cyanophenyl) piperidin-1'-yl)propyl] aminocarbonyltetrahydropyrimidin-2-one;

4-(3,4-difluorophenyl)-3-[4'-(2-cyano-4-fluorophenyl) piperidin-1'-yl)propyl] aminocarbonyltetrahydropyrimidin-2-one;

4-(3,4-difluorophenyl)-1-methyl-3-[(4'-(4-fluorophenyl) piperidin-1'-yl)propyl] aminocarbonyltetrahydropyrimidin-2-one;

(4R)-4-(3,4-difluorophenyl)-5,5-dimethyl-1-((R)-α-methylbenzyl)-3-[(4'-(4-fluorophenyl)piperidin-1'-yl) propyl]amino-carbonyltetrahydropyrimidin-2-one;

(4S)-4-(3,4-difluorophenyl)-5,5-dimethyl-1-((R)-α-methylbenzyl)-3-[(4'-(4-fluorophenyl)piperidin-1'-yl) propyl]amino-carbonyltetrahydropyrimidin-2-one;

(4R)-4-(3,4-difluorophenyl)-5,5-dimethyl-3-[(4'-(4-fluorophenyl)-piperidin-1'-yl)propyl] aminocarbonyltetrahydropyrimidin-2-one;

(4R)-4-(3,4-difluorophenyl)-5,5-dimethyl-3-[(4'-(4-fluorophenyl)-piperidin-1'-yl)propyl] aminocarbonyltetrahydropyrimidin-2-one;

(4R)-4-(3,4-difluorophenyl)-5,5-dimethyl-1-benzyl-3-[(4'-(4-fluorophenyl) piperidin-1'-yl)propyl] aminocarbonyltetrahydropyrimidin-2-one;

(4S)-4-(3,4-difluorophenyl)-5,5-dimethyl-1-benzyl-3-[(4'-(4-fluorophenyl) piperidin-1'-yl)propyl] aminocarbonyltetrahydropyrimidin-2-one;

(4'R)-spirocyclohexane-[1,5']-{4-(3,4-difluorophenyl)-3-[(4'-(4-fluorophenyl) piperidin-1'-yl)propyl] aminocarbonyl}-tetrahydropyrimidin-2-one;

(4'S)-spirocyclohexane-[1,5']-{4-(3,4-difluorophenyl)-3-[(4'-(4-fluorophenyl)piperidin-1'-yl)propyl] aminocarbonyl}-tetrahydropyrimidin-2-one;

(4R,5S)-5-cyclopropyl-4-(3,4-difluorophenyl)-3-[(4'-(4-fluorophenyl)-piperidin-1'-yl) propyl]aminocarbonyl-tetrahydropyrimidin-2-one;

(4S,5S)-5-cyclopropyl-4-(3,4-difluorophenyl)-3-[(4'-(4-fluorophenyl)-piperidin-1'-yl) propyl]aminocarbonyl-tetrahydropyrimidin-2-one;

(4R,5R)-5-cyclopropyl-4-(3,4-difluorophenyl)-3-[(4'-(4-fluorophenyl)-piperidin-1'-yl) propyl]aminocarbonyl-tetrahydropyrimidin-2-one;

(4S,5R)-5-cyclopropyl-4-(3,4-difluorophenyl)-3-[(4'-(4-fluorophenyl)-piperidin-1'-yl) propyl]aminocarbonyl-tetrahydropyrimidin-2-one;

(4R,5S)-5-methyl-4-(3,4-difluorophenyl)-3-[(4'-(4-fluorophenyl)piperidin-1'-yl) propyl]aminocarbonyl-tetrahydropyrimidin-2-one;

(4S,5S)-5-methyl-4-(3,4-difluorophenyl)-3-[(4'-(4-fluorophenyl)piperidin-1'-yl) propyl]aminocarbonyl-tetrahydropyrimidin-2-one;

(4R,5R)-5-methyl-4-(3,4-difluorophenyl)-3-[(4'-(4-fluorophenyl)piperidin-1'-yl) propyl]aminocarbonyl-tetrahydropyrimidin-2-one;

(4S,5R)-5-methyl-4-(3,4-difluorophenyl)-3-[(4'-(4-fluorophenyl)piperidin-1'-yl) propyl]aminocarbonyl-tetrahydropyrimidin-2-one;

and pharmaceutically acceptable salts thereof.

9. The compound according to claim 7, wherein the compound is Isomer D of Example 21.

10. The compound according to claim 2, wherein A is of formula

Q is absent, $[C(R^{a\prime}R^{b\prime})]_{1-4}$, $O[C(R^{a\prime}R^{b\prime})]_{1-2}$, $[C(R^{a\prime}R^{b\prime})]_{1-2}O$, or $C(R^{a\prime})=C(R^{b\prime})$; and T is absent, $C(=O)$, $C(=O)O$, $N(SO_2R^{c\prime})C(R^{a\prime}R^{b\prime})$, $N(R^{c\prime})C=O$, or $N(R^{c\prime})C(=O)O$, provided that (i) when T is absent, Q is $[C(R^{a\prime}R^{b\prime})]_{2-4}$, $O[C(R^{a\prime}R^{b\prime})]_{1-2}$, $[C(R^{a\prime}R^{b\prime})]_{1-2}O$, or $C(R^{a\prime})=C(R^{b\prime})$; (ii) when T is $C(=O)$ or $C(=O)O$, Q is $C(R^{a\prime}R^{b\prime})$ or $C(R^{a\prime}R^{b\prime})C(R^{a\prime}R^{b\prime})$; and (iii) when T is $N(SO_2R^{c\prime})C(R^{a\prime}R^{b\prime})$, $N(R^{c\prime})C=O$, or $N(R^{c\prime})C(=O)O$, Q is absent or $C(R^{a\prime}R^{b\prime})$;

or a pharmaceutically acceptable salt thereof.

11. The compound according to claim 10, wherein the compound is of formula wherein $R^1$ is hydrogen, $C_1-C_4$ alkyl, or $(CH_2)_{0-4}CF_3$;

$R^2$ and $R^3$ are each independently selected from hydrogen, cyano, $C_1-C_4$ alkyl, $(CH_2)_{0-4}CF_3$, $C_3-C_6$ cycloalkyl, fluorinated $C_3-C_6$ cycloalkyl, $(CH_2)_{0-4}CO_2R^d$, $(CH_2)_{0-4}OR^d$, and $(CH_2)_{0-4}CON(R^d)_2$;

$R^4$ and $R^5$ are each independently selected from hydrogen, $C_1-C_4$ alkyl, $(CH_2)_{0-4}CF_3$, $C_3-C_6$ cycloalkyl, fluorinated $C_3-C_6$ cycloalkyl, and $(CH_2)_{0-4}OR^d$;

each X is independently hydrogen, halogen, cyano, $C_1-C_4$ alkyl, $(CH_2)_{0-4}CF_3$, $C_1-C_4$ alkoxy, $OCF_3$, $(CH_2)_{0-4}CO_2R^d$, $(CH_2)_{1-4}OCH_3$, or $(CH_2)_{1-4}OCF_3$;

each $Y^1$ is independently hydrogen, halogen, cyano, $C_1-C_4$ alkyl, $(CH_2)_{0-4}CF_3$, $C_1-C_4$ alkoxy, $OCF_3$, $(CH_2)_{0-4}CO_2R^d$, $(CH_2)_{1-4}OCH_3$, or $(CH_2)_{1-4}OCF_3$;

$R^a$ and $R^b$ are each independently selected from hydrogen, $C_1-C_4$ alkyl, $(CH_2)_{0-4}CF_3$, $C_3-C_6$ cycloalkyl, and fluorinated $C_3-C_6$ cycloalkyl;

$R^c$ is hydrogen, $C_1-C_4$ alkyl, $(CH_2)_{0-4}CF_3$, $C_3-C_6$ cycloalkyl, fluorinated $C_3-C_6$ cycloalkyl, or $CHR_{k1}R^{k2}$;

$R^d$ is hydrogen, $C_1-C_4$ alkyl, or $(CH_2)_{0-4}CF_3$;

$R^{k1}$ is hydrogen or $C_1-C_4$ alkyl;

$R^{k2}$ is phenyl or substituted phenyl, wherein each of the substituents on substituted phenyl is halogen, cyano, $C_1-C_4$ alkyl, fluorinated $C_1-C_4$ alkyl, $C_1-C_4$ alkoxy, $OCF_3$, $(CH_2)_{0-4}CO_2R^d$, $(CH_2)_{1-4}OCH_3$, or $(CH_2)_{1-4}OCF_3$;

$R^{a\prime}$ and $R^{b\prime}$ are each independently selected from hydrogen, $C_1-C_4$ alkyl, and $(CH_2)_{0-4}CF_3$;

"a" represents a single bond or a double bond between the carbon atom to which $R^a$ is attached and the carbon atom to which $R^{b\prime}$ is attached;

n is an integer from 3 to 5;

s1 is an integer from 0 to 4; and s2 is an integer from 0 to 3;

or a pharmaceutically acceptable salt thereof.

12. The compound according to claim 11, wherein the compound is of formula wherein $R^2$ and $R^3$ are each independently selected from hydrogen, cyano, methyl, ethyl, $CF_3$, $CH_2CF_3$, $C_3-C_6$ cycloalkyl, $CO_2CH_3$, $CH_2CO_2CH_3$, $OCH_3$, $CH_2OCH_3$, $CONH_2$, and $CH_2CONH_2$;

$R^4$ and $R^5$ are each independently selected from hydrogen, methyl, ethyl, $CF_3$, $CH_2CF_3$, $C_3-C_6$ cycloalkyl, $OCH_3$, $CH_2OCH_3$, $OCF_3$, $CH_2OCF_3$;

each X is independently hydrogen, fluorine, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$;

each $Y^2$ is independently hydrogen, halogen, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$;

s1 is an integer from 0 to 3; and s2 is an integer from 0 to 2;

or a pharmaceutically acceptable salt thereof.

13. The compound according to claim 12, wherein the compound is selected from the group consisting of 6(R)-1-[3-[spiro-indane-(1,4')-piperidin-1-yl]propyl-aminocarbonyl]-6-(3,4-difluorophenyl)piperidin-2-one;

6(S)-1-[3-[spiro-indane-(1,4')-piperidin-1-yl]propyl-aminocarbonyl]-6-(3,4-difluorophenyl)piperidin-2-one;

and pharmaceutically acceptable salts thereof.

14. The compound according to claim 2, wherein the comound is of formula wherein $R^1$ is hydrogen, $C_1-C_4$ alkyl, or $(CH_2)_{0-4}CF_3$;

R² and R³ are each independently selected from hydrogen, cyano, $C_1$–$C_4$ alkyl, $(CH_2)_{0-4}CF_3$, $C_3$–$C_6$ cycloalkyl, fluorinated $C_3$–$C_6$ cycloalkyl, $(CH_2)_{0-4}CO_2R^d$, $(CH_2)_{0-4}OR^d$, and $(CH_2)_{0-4}CON(R^d)_2$;

R⁴ and R⁵ are each independently selected from hydrogen, $C_1$–$C_4$ alkyl, $(CH_2)_{0-4}CF_3$, $C_3$–$C_6$ cycloalkyl, fluorinated $C_3$–$C_6$ cycloalkyl, and $(CH_2)_{0-4}OR^d$;

each X is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

$R^a$ and $R^b$ are each independently selected from hydrogen, $C_1$–$C_4$ alkyl, $(CH_2)_{0-4}CF_3$, $C_3$–$C_6$ cycloalkyl, and fluorinated $C_3$–$C_6$ cycloalkyl;

$R^c$ is hydrogen, $C_1$–$C_4$ alkyl, $(CH_2)_{0-4}CF_3$, $C_3$–$C_6$ cycloalkyl, fluorinated $C_3$–$C_6$ cycloalkyl, or $CHR^{k1}R^{k2}$;

$R^d$ is hydrogen, $C_1$–$C_4$ alkyl, or $(CH_2)_{0-4}CF_3$;

$R^{k1}$ is hydrogen or $C_1$–$C_4$ alkyl;

$R^{k2}$ is phenyl or substituted phenyl, wherein each of the substituents on substituted phenyl is independently halogen, cyano, $C_1$–$C_4$ alkyl, fluorinated $C_1$–$C_4$ alkyl, $C_1$–$C_4$ alkoxy, $OCF_3$, $(CH_2)_{0-4}CO_2R^d$, $(CH_2)_{1-4}OCH_3$, or $(CH_2)_{1-4}OCF_3$; and s1 is an integer from 0 to 4;

or a pharmaceutically acceptable salt thereof.

15. The compound according to claim 14, wherein the compound is of formula

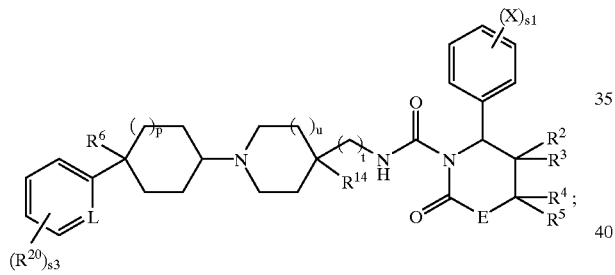

wherein

L is N or $CR^{20}$;

R² and R³ are each independently selected from hydrogen, cyano, methyl, ethyl, $CF_3$, $CH_2CF_3$, $C_3$–$C_6$ cycloalkyl, $CO_2CH_3$, $CH_2CO_2CH_3$, $OCH_3$, $CH_2OCH_3$, $CONH_2$, and $CH_2CONH_2$;

R⁴ and R⁵ are each independently selected from hydrogen, methyl, ethyl, $CF_3$, $CH_2CF_3$, $C_3$–$C_6$ cycloalkyl, $OCH_3$, $CH_2OCH_3$, $OCF_3$, $CH_2OCF_3$;

R⁶ is hydrogen, cyano, hydroxy, $CO_2CH_3$, $CO_2H$, $CONH_2$, phenyl, or substituted phenyl; wherein each of the substituents on substituted phenyl is independently fluorine, chlorine, cyano, hydroxy, methyl, ethyl, $CF_3$, $OCH_3$, $(CH_2)_{1-2}OCH_3$, or $(CH_2)_{1-2}OCF_3$, $C_2OCH_3$, or $CH_2CO_2CH_3$;

$R^{14}$ is hydrogen or hydroxy;

each $R^{20}$ is independently hydrogen, halogen, cyano, methyl, ethyl, $CF_3$, methoxy, ethoxy, $OCF_3$, $C_2OCH_3$, $CH_2CO_2CH_3$, $(CH_2)_{1-4}OCH_3$, or $(CH_2)_{1-4}OCF_3$;

each X is independently hydrogen, fluorine, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$;

s1 is an integer from 0 to 3;

s3 is an integer from 0 to 2; and t is an integer from 0 to 2, provided that when t is 0, $R^{14}$ is hydrogen;

or a pharmaceutically acceptable salt thereof.

16. The compound according to claim 15, wherein E is $CR^aR^b$;

or a pharmaceutically acceptable salt thereof.

17. The compound according to claim 16, wherein the compound is selected from the group consisting of 6(R)-1-[[3(R)-1-[trans-4-(2-pyridyl)cyclohexyl] pyrrolidin-3-yl]-aminocarbonyl]-6-(3,4-difluorophenyl)piperidin-2-one;

6(S)-1-[[3(R)-1-[trans-4-(2-pyridyl)cyclohexyl] pyrrolidin-3-yl]-aminocarbonyl]-6-(3,4-difluorophenyl)piperidin-2-one;

and pharmaceutically acceptable salts thereof.

18. The compound according to claim 15, wherein E is $NR^c$;

or a pharmaceutically acceptable salt thereof.

19. The compound according to claim 18, wherein the compound is selected from the group consisting of 3-[[3(R)-1-[trans-4-(2-pyridyl)cyclohexyl]pyrrolidin-3-yl]-aminocarbonyl]-1-((R)-α-methylbenzyl)-4-(3,4-difluorophenyl)pyrimidin-2-one;

3-[[3(R)-1-[trans-4-(2-pyridyl)cyclohexyl]pyrrolidin-3-yl]-aminocarbonyl]-4-(3,4-difluorophenyl)pyrimidin-2-one;

3-[[3(R)-1-[trans4-(2-methoxy-4-fluorophenyl) cyclohexyl]pyfrolidin-3-yl]-aminocarbonyl]-1-((R)-α-methylbenzyl)-4-(3,4-difluorophenyl)pyrimidin-2-one;

and pharmaceutically acceptable salts thereof.

20. The compound according to claim 2, wherein the compound is of formula:

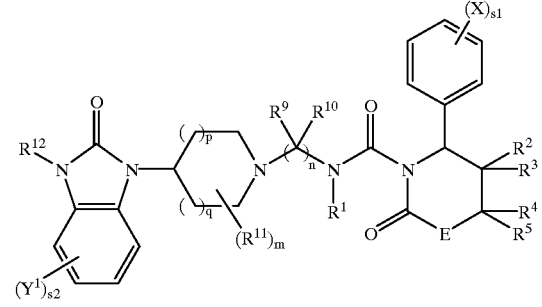

wherein $R^1$ is hydrogen, $C_1$–$C_4$ alkyl, or $(CH2)_{0-4}CF_3$;

R² and R³ are each independently selected from hydrogen, cyano, $C_1$–$C_4$ alkyl, $(CH_2)_{0-4}CF_3$, $C_3$–$C_6$ cycloalkyl, fluorinated $C_3$–$C_6$ cycloalkyl, $(CH2)_{0-4}CO_2R^d$, $(CH_2)_{0-4}R^d$, and $(CH_2)_{0-4}CON(R^d)_2$;

R⁴ and R⁵ are each independently selected from hydrogen, $C_1$–$C_4$ alkyl, $(CH_2)_{0-4}CF_3$, $C_3$–$C_6$ cycloalkyl, fluorinated $C_3$–$C_6$ cycloalkyl, and $(CH_2)_{0-4}OR^d$;

$R^{12}$ is hydrogen, $C_1$–$C_4$ alkyl, $(CH_2)_{0-4}CF_3$, $C_3$–$C_6$ cycloalkyl, or fluorinated $C_3$–$C_6$ cycloalkyl;

each X is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $Y^1$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

$R^a$ and $R^b$ are each independently selected from hydrogen, $C_1$–$C_4$ alkyl, $(CH_2)_{0-4}CF_3$, $C_3$–$C_6$ cycloalkyl, and fluorinated $C_3$–$C_6$ cycloalkyl;

$R^c$ is hydrogen, $C_1$–$C_4$ alkyl, $(CH_2)_{0-4}CF_3$, $C_3$–$C_6$ cycloalkyl, fluorinated $C_3$–$C_6$ cycloalkyl, or $CHR^{k1}R^{k2}$;

$R^d$ is hydrogen, $C_1$–$C_4$ alkyl, or $(CH_2)_{0-4}CF_3$;

$R^{k1}$ is hydrogen or $C_1$–$C_4$ alkyl;

$R^{k2}$ is phenyl or substituted phenyl, wherein each of the substituents on substituted phenyl is independently halogen, cyano, $C_1$–$C_4$ alkyl, fluorinated $C_1$–$C_4$ alkyl, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

n is an integer from 3 to 5;

s1 is an integer from 0 to 4; and s2 is an integer from 0 to 3;

or a pharmaceutically acceptable salt thereof.

21. The compound according to claim 20, wherein the compound is of formula

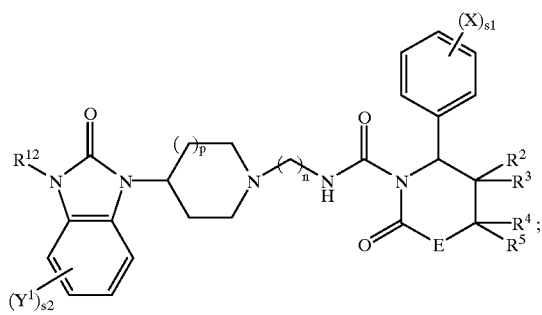

wherein $R^2$ and $R^3$ are each independently selected from hydrogen, cyano, methyl, ethyl, $CF_3$, $CH_2CF_3$, $C_3$–$C_6$ cycloalkyl, $CO_2CH_3$, $CH_2CO_2CH_3$, $OCH_3$, $CH_2OCH_3$, $CONH_2$, and $CH_2CONH_2$;

$R^4$ and $R^5$ are each independently selected from hydrogen, methyl, ethyl, $CF_3$, $CH_2CF_3$, $C_3$–$C_6$ cycloalkyl, $OCH_3$, $CH_2OCH_3$, $OCF_3$, $CH_2OCF_3$;

each X is independently hydrogen, fluorine, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$ each $Y^1$ is independently hydrogen, fluorine, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$;

s1 is an integer from 0 to 3; and s2 is an integer from 0 to 2;

or a pharmaceutically acceptable salt thereof.

22. The compound according to claim 21, wherein E is $CR^aR^b$;

or a pharmaceutically acceptable salt thereof.

23. The compound according to claim 22, wherein the compound is selected from the group consisting of 1-[4-[4-(2-keto-1-benzimidazolinyl)piperidin-1-yl]butylaminocarbonyl]-6-phenylpiperidin-2-one;

and pharmaceutically acceptable salts thereof.

24. A pharmaceutical composition comprising a therapeutically effective amount of the compound according to claim 1 and a pharmaceutically acceptable carrier.

25. A pharmaceutical composition made by combining a therapeutically effective amount of the compound according to claim 1 and a pharmaceutically acceptable carrier.

26. A process for making a pharmaceutical composition comprising combining a therapeutically effective amount of the compound according to claim 1 and a pharmaceutically acceptable carrier.

27. A method of treating benign prostatic hyperplasia in a subject in need thereof which comprises administering a therapeutically effective amount of the composition according to claim 24.

28. A method of relaxing lower urinary tract tissue in a subject in need thereof which comprises administering to the subject a therapeutically effective amount of the compound according to claim 1.

* * * * *